(12) United States Patent
Milbrandt et al.

(10) Patent No.: US 6,284,540 B1
(45) Date of Patent: Sep. 4, 2001

(54) ARTEMIN, A NOVEL NEUROTROPHIC FACTOR

(75) Inventors: Jeffrey D. Milbrandt; Robert H. Baloh, both of St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/220,528

(22) Filed: Dec. 24, 1998

Related U.S. Application Data

(60) Division of application No. 09/218,698, filed on Dec. 22, 1998, and a continuation-in-part of application No. 09/163,283, filed on Sep. 29, 1998.
(60) Provisional application No. 60/108,148, filed on Nov. 12, 1998.

(51) Int. Cl.$^7$ ............................... C12N 5/00; C12N 5/08; C12N 15/63; C12N 15/85; C07H 21/04
(52) U.S. Cl. ...................... 435/455; 435/320.1; 435/325; 435/366; 435/368; 435/383; 435/384; 536/23.5
(58) Field of Search ............................... 530/350; 514/44; 435/4, 320.1, 5, 29; 536/23.5

(56) References Cited

U.S. PATENT DOCUMENTS

| | | | |
|---|---|---|---|
| 5,739,307 | 4/1998 | Johnson, Jr. et al. | 536/23.51 |
| 5,747,655 | 5/1998 | Johnson, Jr. et al. | 530/399 |

FOREIGN PATENT DOCUMENTS

| | | |
|---|---|---|
| WO 00/04050 | 1/2000 | (WO) . |
| WO00/01815 | 1/2000 | (WO) . |

OTHER PUBLICATIONS

Nishino et al., "GFRa3, a Component of the Artemin Receptor is Required for Migration and Survival of the Superior Cervical Ganglion." Neuron, vol. 23: 725–736, Aug. 1999.*
Airaksinen et al., "Review–GDNF Family Neurotrophic Factor Signaling: Four Masters, One Servant?" Molecular and Cellular Neuroscience, vol. 13 :313–325, 1999.*
Saarma et al., "Other Neurotrophic Factors: Glial Cell Line–Derived Neurotrophic Factor (GDNF)." Microscopy Researcha nd Technique, vol. 45: 292–302, 1999.*
Miller et al., "Targeted vectors for gene therapy." FASEB Journal, vol. 9: 190–199, Feb. 1995.*
Blau et al., "Molecular Medicine Gene Therapy—A novel form of drug delivery." The New England Journal of Medicine, vol. 333 (18): 1204–1207, Nov. 1995.*
Crystal R, "Transfer of Genes to Humans: Early Lessons and Obstacles to Success." Science, vol. 270: 404–410, Oct. 1995.*
Verma et al., "Gene Therapy—promises, problems, and prospects." Nature, vol. 389: 239–242, Sep. 1997.*
Ross et al., "Gene Therapy in the United States: A Five Year Status Report." Human Gene Therapy, vol. 7 :1781–1790, Sep. 1996.*
Scheffler et al., "Marrow–mindedness: a perspective on neuropoiesis." TINS, vol. 22 (8): 348–357, 1999.*
Sanberg et al., "Cellular therapeutic approaches for neurodegenerative disorders." Proceedings of the 1998 Miami Bio/Technology winter symposium, Nucleic Acids symposium series No. 38 : 139–142, Feb. 1998.*
Bowie et al., "Deciphering the message in protein sequences: Tolerance to amino acid substitution." Science, vol. 247: 1306–1310, Mar. 1990.*
Ngo et al., "Computational complexity, protein structure prediction, and the Levinthal Paradox." The Protein Folding Problem and Tertiary Structure Prediction :491–495, 1994.*
Frommel et al., "En estimate on the effect of point mutation and natural selection on the rate of amino acid replacement in proteins." Mol. Evol., vol. 21: 233–257, 1985.*
Baloh et al., GFRα3 is an orphan member of the GDNF/neurturin/persephin receptor family, *Proc. Natl. Acad. Sci. USA* 95:5801–5806 (1998).
Jing et al., GFRα–2 and GFRα–3 Are Two New Receptors for Ligands of the GDNF Family, *J. Biol. Chem.* 272:33111–33117 (1997).
National Cancer Institute, Cancer Genome Anatomy Project, *GenBank* AA533512.
National Cancer Institute, Cancer Genome Anatomy Project, *GenBank* AA931637.
Naveilhan et al., Expression and regulation of GFRα3, a glial cell line–derived neurotrophic factor family receptor, *Proc. Natl. Acad. Sci. USA* 95:1295–1300 (1998).
Waterston, *GenBank* AC005038.
Waterston, *GenBank* AC005051.
Widenfalk et al., GFRα–3, a protein related to GFRα–1, is expressed in developing peripheral neurons and ensheathing cells, *Eur. J. Neurosci.* 10:1508–1517 (1998).
Worby et al., Identification and Characterization of GFRα–3, a Novel Co–receptor Belonging to the Glial Cell Line–derived Neurotrophic Receptor Family, *J. Biol. Chem.* 273:3502–3508 (1998).

* cited by examiner

Primary Examiner—Karen M. Hauda
Assistant Examiner—Anne-Marie Baker
(74) Attorney, Agent, or Firm—Howell & Haferkamp, L.C.

(57) ABSTRACT

A novel growth factor, artemin, which belongs to the GDNF/neurturin/persephin family of growth factors, is disclosed. The human and mouse amino sequences have been identified. Human and mouse artemin genomic DNA sequences have been cloned and sequenced and the respective cDNA sequences identified. In addition, methods for treating degenerative conditions using artemin, methods for detecting artemin gene alterations and methods for detecting and monitoring patient levels of artemin are provided.

5 Claims, 39 Drawing Sheets

Figure 1A-1

```
                                                                                                          500                                                          600
R A A R A A G G P G S R A R A A G A R G C R L R S Q L V P V R A L G
TGGGCCACCGCTCCGACGAGCTGCTGGTGCGTTTCCGCTTCTGCAGCGGCTCCTGCGCCGCGCTCCTCCACAGACCTCAGCCTGGCCAGCCTACTGGG
ACCCGGTGGCGAGGCTGCTCGACGAGCCAAAGGCGAAGACGTCGCCGAGGACGTGCGCGAGAGGTGTGCTGGAGTCGGACCGGTCGGATGACCC

L G H R S D E L V R F F C S G S C R R A R S P H D L S L A S L L G
CGCCGGGGCCCCTGCGACCGCCCCGGGCTCCCGGACGCGTCACGCAGCCCTGCTGCCGACCCACGCGTACGAAGCGTCTCCTTCATGACGTCAACAGC
GCGGCCCCGGGGACGCTGGCGGGGCCCGAGGGCCTGCGCAGTGCGTCGGGACGACGGCTGGGTGCGGCGATGCTTCGCCAGAGGAAGTACCTGCAGTTGTCG

A G A L R P P P G S R P V S Q P C C R P T R Y E A V S F M D V N S
ACCTGGAGAACCGTGGAGAGGCTGCTCCGCCACCGCCTCTCCGCCTGCGCCTGCTGGGCTGCTGAGGGCTCGCTCCAGGGCTTTGCAGACTGACCCTTACCGGTGG                                                          696
TGGACCTCTTGGCACCTGGGCGACCTCTCGACGAGGCGGTGGCGGAGAGGCGGGACGCCGACCCCGAGCGAGTTCCGAAACGTCTGACTGGGAATGGCCACC

```
ATGGAACTGGGACTTGCAGAGCCTACTGCAATTGTCCACTGCCTCCGGCCTAGTGGCAGTCAGCCTGGTGGCCAACCCTAGTGTTCTAGCCCTGCTGA    100
TACCTTGACCCTGAACGTCTCGGATGACGTTAACAGGGTGACGGAGGCCCGGATCCAGTCGGTTGGGATCGACAAGATCGGGACGACT

M  E  L  G  L  A  E  P  T  A  I  S  H  C  L  R  P  R  W  Q  S  A  W  W  P  T  L  A  V  L  A  L  L

GCTGCGTCACAGAAGCTTCCCTGGACCCAAATGTCCCGCAGCCCGCTCGGCGACGGTCCCTCACCGGTCTTGGGCGCTCTTGGACGGTCCTGG   200
CGACGCAGTGTCTTCGAAGGGACCTGGGTTACAGGAGGCGCTGCCGCAGGAGTGGCCAGAACCGCCTGGTGCCTGGACGGACC

S  C  V  T  E  A  S  L  D  P  M  S  R  S  P  A  A  R  D  G  P  S  P  V  L  A  P  P  T  D  H  L  P  G

GGGACACACTGCGCATTTGTGCAGCGAAAGAACCCTGGACCCCCGCCTCAGTCTCCTCAGCCCGACTCTCCTCGCCGCTCCTGGTCCCGCCTCCAGTCTCCT   300
CCCTGTGTGACGCGTAAACACGTCGCTTTCTTGGGACGCTGGAGTCAGGAGTCAGGGGGGACCAGGCGGGGGAGGTCAGAGGA

G  H  T  A  H  L  C  S  E  R  T  L  R  P  P  P  Q  S  P  Q  P  A  P  P  P  P  G  P  A  L  Q  S  P

CCCGCTGCGCTCCCGGGGGGACGCGCCCGCCCGTGCCCCGCAGGAGAACCCGCAGGAGCAGCGGACCACAGATGCGCGGCTGCGGCTGCAGCTGG   400
GGGGCGACGCGAGGGCCCCCCTGCGCGGGCACGCCCGCCCCGCACGTTCTACGCGTGTCTACGCGGGAGCGTGCGAGGCGGTCGACC
```

Figure 1C-1

```
P  A  A  L  R  G  A  R  A  A  R  A  G  T  R  S  S  R  A  R  T  T  D  A  R  G  C  R  L  R  S  Q  L
TGCCGGTGAGTGCGCTCGGCGCCTAGGCCACAGCTCCGACGAGCTGATACGTTCCGCTCTGTGCCGAGCACGCTCCCAGCACGATCT
ACGGCCACTCACGCGAGCCGGATCCGGTGTCGAGGCTGCTCGACTATGCAAAGGCTCTGCGAGACGTCGCGAGGGTCGCTGTGTAGA

V  P  V  S  A  L  G  L  G  H  S  S  D  E  L  I  R  F  R  F  C  S  G  S  C  R  R  A  R  S  Q  H  D  L
CAGTCTGGGCCAGCCTACTGGGGCGCTGGAGCCCTACGGTCGCCTCCCGGGTCGCCTGCCGGATCAGCCAGCCCTGTGCCGGCCCACTCGCTATGAGGCCGTC
GTCAGACCGGTCGGATGACCCCGCGACCTCGGGATGCCAGCGGAGGGCCCAGGTAGTCGGTCGGGACGAGCGGGTGAGCGATACTCCGGCAG

S  L  A  S  L  L  G  A  G  A  L  R  S  P  P  G  S  R  P  I  S  Q  P  C  C  R  P  T  R  Y  E  A  V
TCCTTCATGGACGTGAACAGCACCTGGAGGACCGTGGACCACCTCTCCGCCACTGCTGCGGCTGTCTGGGCTGA
AGGAAGTACCTGCACTTGTCGTGGACCTCCTGGCACCTGGTGGAGAGGCGGTGACGACGCCGACAGACCCGACT

```
ATGCCCGGCCTGATCTCAGCCCGAGGACAGCCCCTCCTTGAGGTCCTTCCTCCCTGAGGCTCCACTTGGTC
                                                                      100
TACGGGCCGGACTAGAGTCGGGCTCCGTGGGGAGGAACTCCAGGAAGAAAGAGGGAGACTCCGAGTGAACCAG

M  P  G  L  I  S  A  R  G  Q  P  L  L  E  V  L  P  P  Q  A  H  L  G  A  L  F  L  P  E  A  P  L  G

TCTCCGCGACAGCCTGCCCTGTGGCCACCCTGGCCTCTGCTGAGCAGCGTCGCAGAGGCCCTCCCTGGCTCCGAGGCCCTCCCCC
                                                                                     200
AGAGGCGCGTCGGACGGTGGGACACCGGGCTGGACCGCGAGACGACGTCGCAGCAGCGTCTCCGAGGGACCCGAGGCGTCGGACGGGG

L  S  A  Q  P  A  L  W  P  T  L  A  A  L  A  L  L  S  S  V  A  E  E  A  S  L  G  S  A  P  R  S  P  A  P

CCGCGAAGGCCCCCGCCTGTCCTGGCCGTCCCCGCCACCTGCCGGGGACGCACCGGCCCGCTGGTGCAGTGAAGAGCCCGGCGCCG
                                                                                       300
GGCGCTTCCGGGGGCGGACAGGACCCGGCAGGGGCGCCCCTGCGTGGCCGGGCGACCAGTCACTTCTCGGGCCGCGGGGGGCGGC

R  E  G  P  P  P  V  L  A  S  P  A  G  H  L  P  G  G  R  T  A  R  W  C  S  G  R  A  R  R  P  P  P

CAGCCTTCTCGGCCCGCCTGCACCCCATCTGCTCTTCCCCGCGGGGCCCGGGGCCCGGGCAGCCGGCTCGGG
                                                                      400
GTCGGAAGAGCCGGGCGGACGTGGGGTAGACGAGAAGGGGCGCCGGGGCGGGGGTAGCGGCCGAGCCC
```

```
        GCGGCGCGGGGCTGGGGGGCCCAGCTGGTGCCGGTGCGCGCGCTCGGCCTGG
                                                         100
        CGCCGCGCCCCGACCCCCGCGCTCGGCAGCGCCGTCGACCACGGCCGAGCCGACC
         A  R  A  G  G  P  G  S  R  A  R  A  A  G  A  R  G  C  R  L  R  S  Q  L  V  P  V  R  A  L  G  L

GCCACCGCTCCGACGAGCTGGTGCGCTTTCGCTTCTGCAGCGGCTGCCGCGCTCTCCACACGACCTCAGCCTGGCCAGCCTACTGGGCGC
                                                         200
        CGGTGGCGAGGCTGCTCGACCACGCGAAAGCGCGAGACGTCGCCGACGGCGTGCTGGAGTCGGACCGGTCGGATGACCCGCG
         G  H  R  S  D  E  L  V  R  F  R  F  C  S  G  C  R  R  A  R  S  P  H  D  L  S  L  A  S  L  L  G  A

CGGGGCCCTGCGACCGCCTCTCCGGCCTCAGCCCGTGCTGCCGACCCAGCCCTGCTGCCGGTCTCCCTTCATGGACGTCAACAGCACC
                                                         300
        GCCCCGGGACGCTGGCGGAGAGGCCGGAGTCGGGACTCGGGTGCCGATGTCTTCGCCAGAGGAAGTACCTGCAGTTGTCGTGG
         G  A  L  R  P  P  G  S  R  P  V  S  Q  P  C  C  R  P  T  R  Y  E  A  V  S  F  M  D  V  N  S  T

TGGAGAACCGTGGACCGGCCTCTCCGCCTGCCTGGGGCTGA
                                                351
        ACCTCTTGGCACCTGGCGAGAGGCGGACGCCGACGACCCGACT
         W  R  T  V  D  R  L  S  A  T  A  C  G  L  G
```

|   | 1 | 2 | 3 | 4 | 5 | 6 | 7 | 8 |
|---|---|---|---|---|---|---|---|---|
| A | whole brain | amygdala | caudate nucleus | cerebellum | cerebral cortex | frontal lobe | hippocampus | medulla oblongata |
| B | occipital pole | putamen | substantia nigra | temporal lobe | thalamus | subthalamic nucleus | spinal cord | |
| C | heart | aorta | skeletal muscle | colon | bladder | uterus | prostate | stomach |
| D | testis | ovary | pancreas | pituitary gland | adrenal gland | thyroid gland | salivary gland | mammary gland |
| E | kidney | liver | small intestine | spleen | thymus | peripheral leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast total RNA | yeast tRNA | E. coli rRNA | E. coli DNA | Poly r(A) | human $C_0t$ DNA | human DNA | human DNA |

Figure 5B

```
hGFRα3  MVRPLNPRPLPPVLMLLLPPSPLPLAAGDPLPTESRLM
mGFRα3  MGLSWSPRP--PLMILLLVLSLW-LPLGAGNSLATENRFV hGFRα3  NSCLQARRKCQADPTCSAAYHHLDSCTSSISTPLPSEEPSV
mGFRα3  NSCTQARKKCEANPACKAAYQHLGSCTSSLSRPLPLEESAM hGFRα3  PADCLEAAQQLRNSSLIGCMCHRRMKNQVACLDIYWTVHRA
mGFRα3  SADCLEAAEQLRNSSLIDCRCHRRMKHQATCLDIYWTVHPA hGFRα3  RSLGNYELDVSPYEDTVTSKPWKMNLSKLNMLKPDSDLCLK
mGFRα3  RSLGDYELDVSPYEDTVTSKPWKMNLSKLNMLKPDSDLCLK hGFRα3  FAMLCTLNDKCDRLRKAYGEACSGPHCQRHVCLRQLTFEE
mGFRα3  FAMLCTLHDKCDRLRKAYGEACSGIRCQRHLCLAQLRSFFE hGFRα3  KAAEPHAQGLLLCPCAPNDRGCGERRRNTIAPNCALPPVAP
mGFRα3  KAAESHAQGLLLCPCAPEDAGCGERRRNTIAPSCALPSVTP hGFRα3  NCLELRRLCSDPLCRSRLVDFQTHCHPMDILGTCATEQSR
mGFRα3  NCLDLRSFCRADPLCRSRLMDFQTHCHPMDILGTCATEQSR hGFRα3  CLRAYLGLIGTAMTPNFVSNVNTSVALSCTCRGSGNLQEEC
mGFRα3  CLRAYLGLIGTAMTPNFISKVNTTVALSCTCRGSGNLQDEC hGFRα3  EMLEGFFSHNPCLTEAIAAKMRFHSQLFSQDWPHPTFAVMA
mGFRα3  EQLERSFSQNPCLVEAIAAKMRFHRQLFSQDWADSTFSVVQ hGFRα3  HQNENPAVRPQPWVPSLFSCTLPLILLSLW
mGFRα3  QQNSNPALRLQPRLPLLSFSILPLILQTLW
```

FIGURE 12

ATGGTGCGCCCCCTGAACCCGCGACCGCTGCCGCCCGTAGTCCTGATGTTGCTGCTGCTGCTGCCCGTCGCCGCTGCC
TCTCGCAGCCGGAGACCCCCTTGCCTACCACCACCTGGATTCCTGCAGAAAGCCGACTCATGAACAGCTGTCTCCAGGCCAGGAGGAAGTGCCAGGCTG
ATCCCACCTGCAGTGCTGCTGACTGCCTGGAGGCAGCAGCAACTCAGGAACAGCTCTCTGATAGGCTGCATGTGCCACCGGCGCAT
TCGGTCCCTGCTGCTGACACCAGGTTGCCTGCTTGGACATCTATTGGACCGTTCACCGTGCCCGAGCCTTGGTAACTATGAGCTGGATGTCT
GAAGAACCAGGTTGCCTGCTTGGACATCTATTGGACCGTTCACCGTGCCCGAGCCTTGGTAACTATGAGCTGGATGTCT
CCCCCTATGAAGACACAGTGACCAGCAAACCTGGAAAATGAATCTCAGCAAACATGCTCAAACCAGACTCAGAC
CTCTGCCTCAAGTTTGCCATGCTGTACTCTCAATGACAAGTGTGACCGGCTGCGCAAGGCCTACGGGGAGGCGTCTC
CGGGCCCCACTGTGCCCAGGCCACGTCTGCCCCCAACGACCGGGCTGCGCGGGGAGCCCGAGCCCCACGCGCAGG
GCCTGCTACTGTGCCCATGTGCCCCCAACTGCCCCTGGAGCTGTTCTCCGACCCGCTTTGCAGATCACGCCTGGTGA
CTGCCGCCTGTGGCCCCACTGCCATCCATGGACATCCCCAACTTTGTCAGCAATGTCAACACCAGTGTTGCCTTAAGCTGCCGAGGC
TTTCCAGACCCACTGCCATCCATGGACATCCCCAACTTTGTCAGCAATGTCAACACCAGTGTTGCCTTAAGCTGCCGAGGC
GGCTGATTGGGACTGCCATGACCCCCAACTTTGTCAGCAATGTCAACACCAGTGTTGCCTTAAGCTGCCGAGGC
AGTGGCAACCTGCAGGAGGAGTGTGAAATGCTGGAAGGTTCTTCCCACACCCTACCTTTGCTGTGATGGCACACCAGAATGAAA
TAAGATGCGTTTCACAGCCAACTCTTCTCCCAGGACTGGCCACACCCTACCTTTGCTGTGATGGCACACCAGAATGAAA
ACCCTGCTGTGAGGCCACAGCCCTGGGTGCCCTCTCTTTTCCTGCACGCTTCCCTTGATTCGCTGCTCCTGAGCCTATGG
TAG

ARTEMIN, A NOVEL NEUROTROPHIC FACTOR

RELATED APPLICATIONS

This application, is a divisional of U.S. application Ser. No. 09/218,698 filed Dec. 22, 1998, which claims priority to Provisional Application Serial No. 60/108,148 filed Nov. 12, 1998, and a continuation-in-part of application Ser. No. 09/163,283, filed Sep. 29, 1998.

REFERENCE TO GOVERNMENT GRANT

This invention was made with government support under NIH Grant Number SR01-AG13730-03. The government has certain rights in this invention.

BACKGROUND OF THE INVENTION

(1) Field of the Invention

This invention relates generally to trophic or growth factors and, more particularly, to a new growth factor, artemin, which is a member of the neurturin-persephin-GDNF family of growth factors.

(2) Description of the Related Art

The development and maintenance of tissues in complex organisms requires precise control over the processes of cell proliferation, differentiation, survival and function. A major mechanism whereby these processes are controlled is through the actions of polypeptides known as "growth factors". These structurally diverse molecules act through specific cell surface receptors to produce these actions.

Growth factors termed "neurotrophic factors" promote differentiation, maintain a mature phenotype and provide trophic support, promoting growth and survival of neurons. Neurotrophic factors reside in the nervous system or in innervated tissues. Nerve growth factor (NGF) was the first neurotrophic factor to be identified and characterized (Levi-Montalcini et al., *J. Exp. Zool.* 116:321, 1951). NGF exists as a non-covalently bound homodimer that promotes the survival and growth of sympathetic, neural crest-derived sensory, and basal forebrain cholinergic neurons. In sympathetic neurons this substance produces neurite outgrowth in vitro and increased axonal and dendritic growth in vivo. (See Levi-Montalcini and Booker, *Proc Nat'l Acad Sci* 46:384–391, 1960; Johnson et al. *Science* 210: 916–918, 1980; Crowley et al., *Cell* 76:1001–12, 1994). NGF has effects on cognition and neuronal plasticity, and can promote the survival of neurons that have suffered damage due to a variety of mechanical, chemical, viral, and immunological insults (Snider and Johnson, *Ann Neurol* 26:489–506, 1989; Hefti, *J Neurobiol* 25:1418–35, 1994). NGF also is known to extensively interact with the endocrine system and in immune and inflammatory processes. (Reviewed in Scully and Otten, *Cell Biol Int* 19:459–469, 1995; Otten and Gadient, *Int. J. Dev'l Neurosci* 13:147–151, 1995). For example, NGF promotes the survival of mast cells. (Horigome et al. *J Biol Chem* 269:2695–2707, 1994).

In recent years it has become apparent that growth factors fall into classes, i.e. families or superfamilies based upon the similarities in their amino acid sequences. These families include, for example, the fibroblast growth factor family, the neurotrophin family and the transforming growth factor-beta (TGF-β) family. As an example of family member sequence similarities, TGF-β family members have 7 canonical framework cysteine residues which identify members of this superfamily.

NGF is the prototype of such a family of growth factors. Brain-derived neurotrophic factor (BDNF), the second member of this family to be discovered, was shown to be related to NGF by virtue of the conservation of all six cysteines that form the three internal disulfides of the NGF monomer (Barde, *Prog Growth Factor Res* 2:237–248, 1990 and Liebrock et al. *Nature* 341:149–152, 1989). By utilizing the information provided by BDNF of the highly conserved portions of two factors, additional members (NT-3, NT-4/5) of this neurotrophin family were rapidly found by several groups (Klein, *FASEB J* 8:738–44, 1994).

Recently, a new family of neurotrophic factors has been identified whose members are not structurally related to NGF and other neurotrophins but are structurally similar to TGF-β. As described in U.S. Pat. No. 5,739,307 and copending application Ser. No. 08/931,858, the known members of this subfamily of the TGF-β superfamily include glial cell line-derived neurotrophic factor (GDNF), neurturin (NTN), and persephin (PSP). The placement of GDNF, neurturin and persephin into the same growth factor family, also referred to as the GDNF ligand family, is based on the similarities of their physical structures and biological activities. Human persephin has about 40% sequence identity and about 43% sequence conservation with human GDNF; and about 49% sequence identity and about 50% sequence conservation with human neurturin. Similarly, human neurturin has about 43% sequence identity and about 53% sequence conservation with human GDNF. In addition, these three proteins have seven cysteine residues whose positions are exactly conserved. GDNF, neurturin and persephin each support the survival of dopaminergic midbrain neurons, and spinal and facial motor neurons, in both in vitro survival and in vivo injury paradigms, identifying these ligands as potential therapeutic agents in the treatment of neurodegenerative diseases (Henderson et al., *Science* 266, 1062–1064, 1994; Horger et al., *J Neurosci.* 18, 4929–37 1998; Lin et al., *Science* 260, 1130–1132, 1993; Milbrandt et al., *Neuron* 20, 245–53, 1998; Oppenheim et al., *Nature* 373, 344–346, 1995), reviewed by (Grondin and Gash, *J Neurol.* 245(11 Suppl 3), 35–42, 1998). However, while GDNF and neurturin both support the survival of many peripheral neurons in culture, including sympathetic, parasympathetic, sensory, and enteric neurons (Buj-Bello et al., *Neuron* 15, 821–828, 1995; Ebendal et al., *J Neurosci Res* 40, 276–284, 1995; Heuckeroth et al., *Dev Biol* 200, 116–29, 1998; Kotzbauer et al., *Nature* 384, 467–470, 1996; Trupp et al., *J of Cell Biology* 130, 137–148, 1995), persephin does not share any of these activities on peripheral neurons (Milbrandt et al., supra.

It was recently reported that GDNF and neurturin share receptors and signal transduction pathways (Creedon et al., *Proc. Natl. Acad. Sci. US* 94:7018–7023, 1997; Durbec et al., *Nature* 381:789–793, 1996; Trupp et al., *Nature* 381:785–789, 1996; Baloh et al., *Neuron* 18:793–802, 1997). These proteins act through a multicomponent receptor complex in which a transmembrane signal transducing component, the Ret protein-tyrosine kinase (Ret or Ret PTK), is activated upon the binding of a growth factor of the GDNF/neurturin family with a member of a family of closely related co-receptors named GRFα. A characteristic feature of the GFRco-receptor family, is that its members have no transmembrane attached to the cell surface via a glycosyl-phosphatidylinositol (GPI) linkage (Durbec et al., *Nature* 381:789–793, 1996; Jing et al., *Cell* 85:1113–1124, 1996; Treanor et al., *Nature* 382:80–83, 1996; Trupp et al., *Nature* 381:785–789, 1996; Baloh et al., 1997, supra). The members of the GRFα family include GFRα1 (previously known as GDNFRα, TrnR$_1$ and RetL1), GFRα2 (previously TrnR2, NTNRα and RetL2), GFRα3 (previously TrnR3)

(GRFα Nomenclature Committee, *Neuron* 19(3):485, 1997) and possibly GFRα4, a receptor currently only identified in the chicken (cGFRα4) (Enokido et al., *Current Biology* 8, 1019–1022, 1998).

Results from in vitro experiments by multiple groups together indicate that GRFα 1/RET is the preferred receptor for GDNF, and GFRα2/RET is the preferred receptor for NTN, however cross-talk between the different receptors is possible (Baloh et al., 1997, supra; Jing et al., 1996, supra; Jing et al., *J Biol. Chem.* 272, 33111–33117, 1997; Klein et al., *Nature* 387, 717–721,1997; Sanicola et al., *Proc. Natl. Acad. Sci., USA* 94, 6238–6243,1997; Suvanto et al., *Hum. Molec. Genet.* 6, 1267–1273,1997; Treanor et al., 1996, supra). Recent analysis of GFRα1-deficient mice indicated that GFRα1 is the only physiologically relevant GDNF receptor in kidney organogenesis and enteric nervous system development (Cacalano et al., *Neuron* 21, 53–62,1998; Enomoto et al., *Neuron* 21, 317–324,1998). However, GDNF-deficient mice have greater losses in peripheral ganglia than GRFα1 -deficient mice, suggesting that GDNF can utilize additional other receptors to support survival of peripheral neurons, likely GFRα2/Ret (Cacalano et al., supra; Enomoto et al., supra). Persephin cannot signal through either the GFRα1/RET or GFRα2/RET receptor complexes (Milbrandt et al., supra), but a recent report indicated that persephin binds to cGFRα4 and likely also signals through RET (Enokido et al., supra).

GFRα3 was first identified as an expressed sequence tag (EST) that is omologous to GFRα1 and GFRα2 (Baloh et al., *Proc. Natl. Acad. Sci USA* 95:5801–5806, 1998, supra; Jing et al., 1997, supra; Naveilhan et al., *Proc Natl Acad Sci USA* 5, 1295–300, 1998; Widenfalk et al., *Eur. J. Neurosci.* 10, 1508–1517, 1998; Worby et al., J Biol Chem 273, 3502–3508, 1998). However, analysis in transformed cells indicated that GFRα3 could not form a functional receptor with RET for any of the known GDNF family ligands, GDNF, neurturin or persephin (Baloh et al., 1998, supra;). GFRα3 expression is much more restricted than GFRα1 or GFRα2, with high level expression observed only in developing peripheral nerve and ganglia (Baloh et al., 1998, supra; Naveilhan et al., supra; Widenfalk et al., supra; Worby et al., 1998). Furthermore, one report demonstrated that in sensory neurons of the trigeminal ganglion, GFRα3 is expressed in a population of neurons distinct from GFRα1 and GFRα2, and likely overlaps with RET (Naveilhan et al., supra). Although the structural similarity, expression, and functional data together suggested that GFRα3 can interact with RET, the work reported herein was the first to demonstrate such an interaction and the first to identify a ligand for GFRα3.

It is now generally believed that neurotrophic factors regulate many aspects of neuronal function, including survival and development in fetal life, and structural integrity and plasticity in adulthood. Since both acute nervous system injuries as well as chronic neurodegenerative diseases are characterized by structural damage and, possibly, by disease-induced apoptosis, it is likely that neurotrophic factors play some role in these afflictions. Indeed, a considerable body of evidence suggests that neurotrophic factors may be valuable therapeutic agents for treatment of these neurodegenerative conditions, which are perhaps the most socially and economically destructive diseases now afflicting our society. Nevertheless, because different neurotrophic factors can potentially act preferentially through different receptors and on different neuronal or non-neuronal cell types, there remains a continuing need for the identification of new members of neurotrophic factor families for use in the diagnosis and treatment of a variety of acute and chronic diseases of the nervous system.

SUMMARY OF THE INVENTION

Briefly, therefore, the present invention is directed to the new growth factor, artemin, which promotes cell survival and growth. Like GDNF and neurturin, artemin supports the survival of several peripheral neuron populations, and can also support dopaminergic neurons of the ventral midbrain. However, artemin is the only member of the GDNF family that binds to GFRα and activates the GFRα3/RET receptor complex and, in addition, like GDNF and neurturin, artemin also binds to and activates GFRα1/RET. GFRα3 is described in patent application entitled "GFRα3, A Novel Member of the GDNF Coreceptor Family" filed concurrently with the present application on Dec. 22, 1998 and this GFRα3 application is incorporated herein in its entirety by reference.

The present invention thus provides artemin polypeptides and polynucleotides. Artemin polypeptides within the scope of the present invention include any of the naturally occurring artemin polypeptides, conservatively substituted variants thereof or fragments thereof. The artemin polypeptides promote survival of peripheral and central neurons in culture, preferably in any one of trigeminal ganglion neurons, nodose ganglion neurons, superior cervical ganglion neurons, and tyrosine-hydroxylase-expressing dopaminergic ventral midbrain neurons; more preferably, in any combination of these neurons and, most preferably, in all of these neurons.

Preferred artemin polypeptides include the predicted human mature polypeptides (SEQ ID NOS:3–5, see FIGS. 3A, 3B, and 3C), and the predicted mouse mature polypeptides (SEQ ID NOS:34–36). These mature polypeptides can be generated by cleaving human or mouse pre-pro artemin (SEQ ID NOS: 26 and 29, respectively) or human or mouse pro-artemin (SEQ ID NOS:40 and 41, respectively), which are also within the scope of this invention, at one of the RXXR cleavage sites (see FIGS. 1A, 1B, 1C and 2B). In addition, mature artemin can be generated by cleaving a polypeptide containing an N-terminal non-artemin pre-pro-region a mature artemin. Artemin polypeptides also include fragments from the first canonical cysteine to the seventh canonical cysteine of human or mouse mature artemin (SEQ ID NO:19 and SEQ ID NO:33, respectively).

Artemin is believed to show at least 75% sequence identity among homologous sequences from different mammalian species and, hence, mammalian orthologs of mature artemin are believed to have at least 75% sequence identity with mature human artemin (SEQ ID NOS:3–5) and mature mouse artemin (SEQ ID NOS:34–36). Sequence homology may be as low as 65% in non-mammalian species such as avian species.

Human artemin polypeptide is encoded by the cDNA contained in the clone deposited with the ATCC on Dec. 22, 1998. Thus, human artemin polypeptide can be produced by transforming a host cell with the cDNA of this clone operably linked to expression regulatory elements. Conditions are then provided such that the cell expresses the encoded human artemin polypeptide. Such human artemin polypeptides are within the scope of the present invention.

The present invention also provides compositions comprising an artemin polypeptide and a pharmaceutically acceptable carrier suitable for administering to a cell to provide trophic support and/or to produce differentiation of that cell in vitro or ex vivo or to a cell in a patient. In order to facilitate the growth promoting effect of artemin, a GFRα coreceptor can be administered with artemin. Thus, in another embodiment, the present invention provides compositions which comprise an artemin polypeptide and a GRFα polypeptide such as GFRα3 or GFRα1.

In another embodiment, the present invention includes pan-growth factors and polynucleotides encoding the pan-growth factors. The pan-growth factors comprise a portion of the artemin polypeptide and a portion of at least one other growth factor from the TGF-β superfamily. Preferably, the other growth factor can be neurturin, persephin or GDNF.

The present invention in another embodiment also provides isolated and purified and/or recombinant nucleic acid molecules comprising artemin nucleotide sequences. The artemin nucleotide sequences encode polypeptides consisting of artemin polypeptides, conservatively substituted variants thereof and fragments thereof. Also within the scope of this invention are fragments of artemin nucleotide sequences of at least 15 contiguous nucleotides. The artemin nucleic acid molecules specifically hybridize to mature human artemin nucleotide sequences (SEQ ID NOS:6–8) or their complements (SEQ ID NOS:9–11) or to mature mouse artemin nucleotide sequences (SEQ ID NOS:37–39) or their complements (SEQ ID NOS:60–62).

Preferred polynucleotides of the present invention comprise the human polynucleotides which encode mature human artemin polypeptides (SEQ ID NOS:3–5), in particular, the polynucleotide sequences in SEQ ID NOS: 6–8 as depicted in FIGS. 3A, 3B, and 3C or the corresponding mouse polynucleotides which encode mature mouse artemin polypeptides.(SEQ ID NOS:34–36), in particular, the polynucleotide sequences in SEQ ID NOS:37–39. Also encompassed by the present invention are human and mouse pro-artemin polynucleotides which encode pro-artemin polypeptides (SEQ ID NOS:40 and 41, respectively), in particular, the polynucleotide sequences in SEQ ID NOS:42 and 43, respectively, and human and mouse pre-pro artemin polynucleotides which encode pre-pro artemin polypeptides (SEQ ID NOS:26 and 29, respectively), in particular, the human polynucleotide sequences, SEQ ID NOS:24, SEQ ID NO:30 or SEQ ID NO:44, and the mouse polynucleotide sequence, SEQ ID NO:27. In addition, polynucleotides can encode a polypeptide containing an N-terminal non-artemin pre-pro-region and a mature artemin such that upon expression of the polypeptide in an expression system and cleavage of the N-terminal non-artemin pre-pro region, a mature artemin is produced. Artemin polynucleotides also include portions of the artemin polynucleotide sequence encoding the polypeptide from the first canonical cysteine to the seventh canonical cysteine (SEQ ID NOS:19 and 33).

Sequences that are capable of hybridizing to human or mouse mature artemin polynucleotides can be used in methods for detecting the artemin gene and transcription products thereof, as well as in isolating artemin-encoding polynucleotides from other mammalian and non-mammalian species. Such methods are also within the scope of the present invention.

The present invention also provides antibodies which specifically react with artemin or a fragment thereof and methods for detecting artemin polypeptide in a sample by binding to the antibody.

In another embodiment, the present invention also provides methods for providing trophic support to and/or for producing differentiation of a target cell which comprises treating the cell with an effective amount of an artemin polypeptide. The target cell can be given artemin in vitro, ex vivo or in vivo in a patient suffering from a medical condition which causes degeneration or a loss of normal function of the target cell. In one preferred embodiment, the cell is treated in vivo by administering to the patient an artemin polypeptide or an artemin polynucleotide encoding for expression the artemin polypeptide. The patient can be suffering from disease such as peripheral neuropathy, amyotrophic lateral sclerosis, Alzheimer's disease, Parkinson's disease Huntington's disease, ischemic stroke, acute brain injury, acute spinal chord injury, nervous system tumors such as neuroblastomas, multiple sclerosis, infection, small cell lung carcinoma and enteric diseases such as idiopathic chronic constipation or constipation associated with Parkinson's disease, spinal cord injury or use of opiate pain-killers.

Among the several advantages found to be achieved by the present invention, therefore, may be noted the provision of a new growth factor, artemin, in particular human artemin, which can be used to prevent the atrophy, degeneration or death of certain cells, in particular, neurons in need of trophic support; the provision of polynucleotides encoding artemin for use in gene therapy; the provision of methods for obtaining artemin by recombinant techniques; the provision of methods for providing trophic support to target cells, particularly neurons; the provision of methods for treating disease conditions involving cellular degeneration, and in particular, neuronal degeneration; the provision of methods that can detect and monitor artemin levels in a patient; and the provision of methods that can detect alterations in the artemin gene.

BRIEF DESCRIPTION OF THE DRAWINGS

FIG. 1A illustrates complementary human artemin genomic nucleotide sequences (SEQ ID NOS:1–2) which were assembled as described in the text, with the amino acids (SEQ ID NO: 12) encoded by the reading frame starting at nucleotide number 1 of the top sequence (SEQ ID NO:1), including the three possible RXXR proteolytic processing sites encoded by the three sets of 12 nucleotides starting at positions 220, 292, and 301 of the top sequence.

FIG. 1B illustrates the complementary cDNA sequences (SEQ ID NOS:24 and 25) and the human pre-pro-artemin amino acid sequence (SEQ ID NO:26) which is encoded by the top nucleotide sequence (SEQ ID NO:24).

FIG. 1C illustrates the complementary cDNA sequences (SEQ ID NOS:27 and 28) and the mouse pre-pro-artemin amino acid sequence (SEQ ID NO:29) which is encoded by the top nucleotide sequence (SEQ ID NO:27).

FIG. 1D illustrates the complementary cDNA sequences (SEQ ID NOS:30 and 31) and the human artemin amino acid sequence (SEQ ID NO:32) which is encoded by the top nucleotide sequence (SEQ ID NO:30), starting from the second methionine found in some human artemin cDNA clones which represent alternatively spliced human artemin mRNA;

Figure 2A:
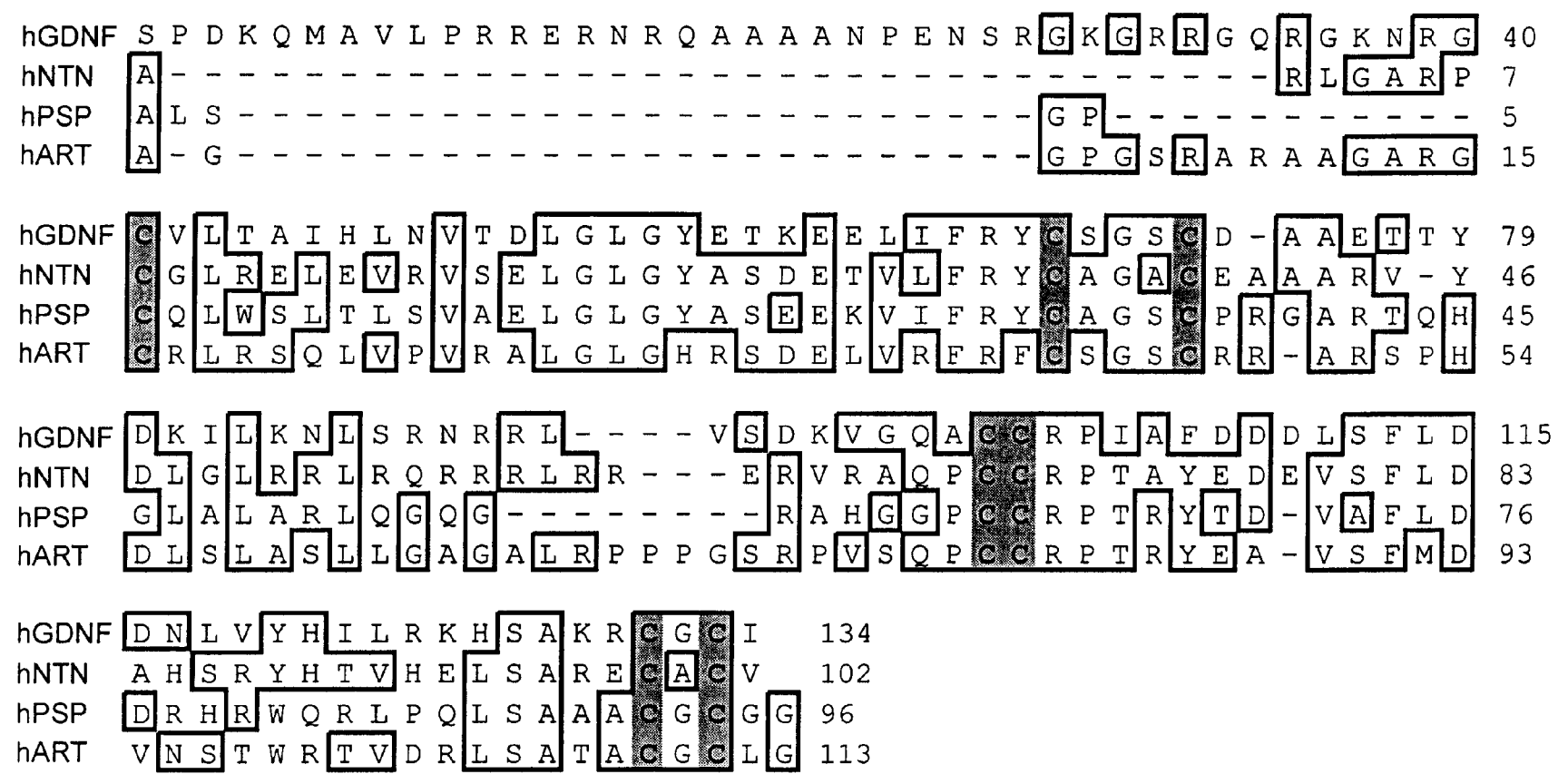

FIG. 2A illustrates an alignment of the amino acid sequences for the predicted mature forms of human GDNF (hGDNF, SEQ ID NO:13), human neurturin (hNTN, SEQ ID NO:14), human persephin (hPSP, SEQ ID NO:15) and human artemin (hART, SEQ ID NO:3) with identical amino acid residues enclosed in boxes and gaps inserted by the alignment program indicated by dashes;

FIG. 3A illustrates the amino acid sequence (SEQ ID NO:3) and the coding sequence (top nucleotide sequence) (SEQ ID NO:6) of a first predicted mature human artemin polypeptide as well as the complement of the coding sequence (bottom nucleotide sequence) (SEQ ID NO:9).

FIG. 3B illustrates the amino acid sequence (SEQ ID NO:4) and the coding sequence (top nucleotide sequence) (SEQ ID NO:7) of a second predicted mature human artemin polypeptide as well as the complement of the coding sequence (bottom nucleotide sequence) (SEQ ID NO: 10).

FIG. 3C illustrates the amino acid sequence (SEQ ID NO:5) and the coding sequence (top nucleotide sequence) (SEQ ID NO:8) of a third predicted mature human artemin polypeptide as well as the complement of the coding sequence (bottom nucleotide sequence) (SEQ ID NO:11).

FIG. 4 illustrates the family member sequence identity in the region between the first and seventh canonical framework cysteine residues aligned beginning with the first canonical framework cysteine for human GDNF (hGDNF, SEQ ID NO:16), human neurturin (hNTN, SEQ ID NO:17), human persephin (hPSP, SEQ ID NO:18) and human artemin (hART, SEQ ID NO:19).

FIGS. 5A and 5B illustrate expression of artemin in human adult and fetal tissues showing in FIG. 5A an RNA spot blot containing poly(A) RNA's isolated from the human tissues shown in FIG. 5B and probed with a fragment of the human artemin cDNA.

FIGS. 7A–7F illustrate that artemin supports the survival of peripheral and central neurons in culture, in which: FIGS. 7A and 7B show histograms of the number of surviving dorsal root ganglion (DRG) neurons cultured from postnatal day 1 (P1) rats in the presence of 50 ng/ml of the indicated factors (FIG. 7A, mean and SEM are shown, n=5–11) or in the presence of the indicated amounts of artemin (FIG. 7B, mean and SEM are shown, n=5); FIG. 7C shows a histogram of number of surviving trigeminal ganglion (TG) neurons cultured from P1 rats in the presence of 50 ng/ml of the indicated growth factor (mean and SEM are shown, n=4); FIG. 7D shows a histogram of the number of surviving nodose ganglion (NG) neurons cultured from P0 rats in the presence of BDNF (100 ng/ml) or the indicated GDNF family ligands (50 ng/ml) (mean and SEM from a representative experiment are shown, n=2); FIG. 7E shows a histogram of the number of surviving superior cervical ganglion (SCG) from P0 rats maintained in the presence of NGF for 5 days and then cultured in the presence of 50 ng/ml of the indicated factors (mean and SEM are shown, n=2–8); and FIG. 7F shows a histogram of the number of tyrosine hydroxylase-expressing (TH+) dopaminergic ventral midbrain neurons from E14 rats (EVM) cultured in the presence of 50 ng/ml of the indicated factors (mean and SEM are shown, n=9–15).

FIG. 12 illustrates the alignment of the amino acid sequences of human and mouse GFRα3 precursor (SEQ ID NOS:63 and 64, respectively), with identical residues enclosed in boxes, the N-terminal signal sequence shaded (amino acids 1–31 in hGFRα3 and 1–28 in mGFRα3), mature GFRα3 (amino acids 32–372 in hGFRα3 and 29–369 in mGFRα3), a shaded C-terminal hydrophobic stretch of residues consistent with a GPI signal peptide shaded (amino acids 373–400 of hGFRα3 and 370–397 of mGFRα3) and putative N-linked glycosylation sites marked by black dots.

FIG. 13 illustrates the human nucleotide sequence encoding GFRα3 precursor (SEQ ID NO:65) which includes the encoding sequence for the N-terminal signal sequence (nucleotides 1–93), the encoding sequence for mature GFRα3 (nucleotides 94–1116) and the encoding sequence for the C-terminal hydrophobic stretch of residues consistent with a GPI signal peptide (nucleotides 1117–1203).

Figure 14A-1:
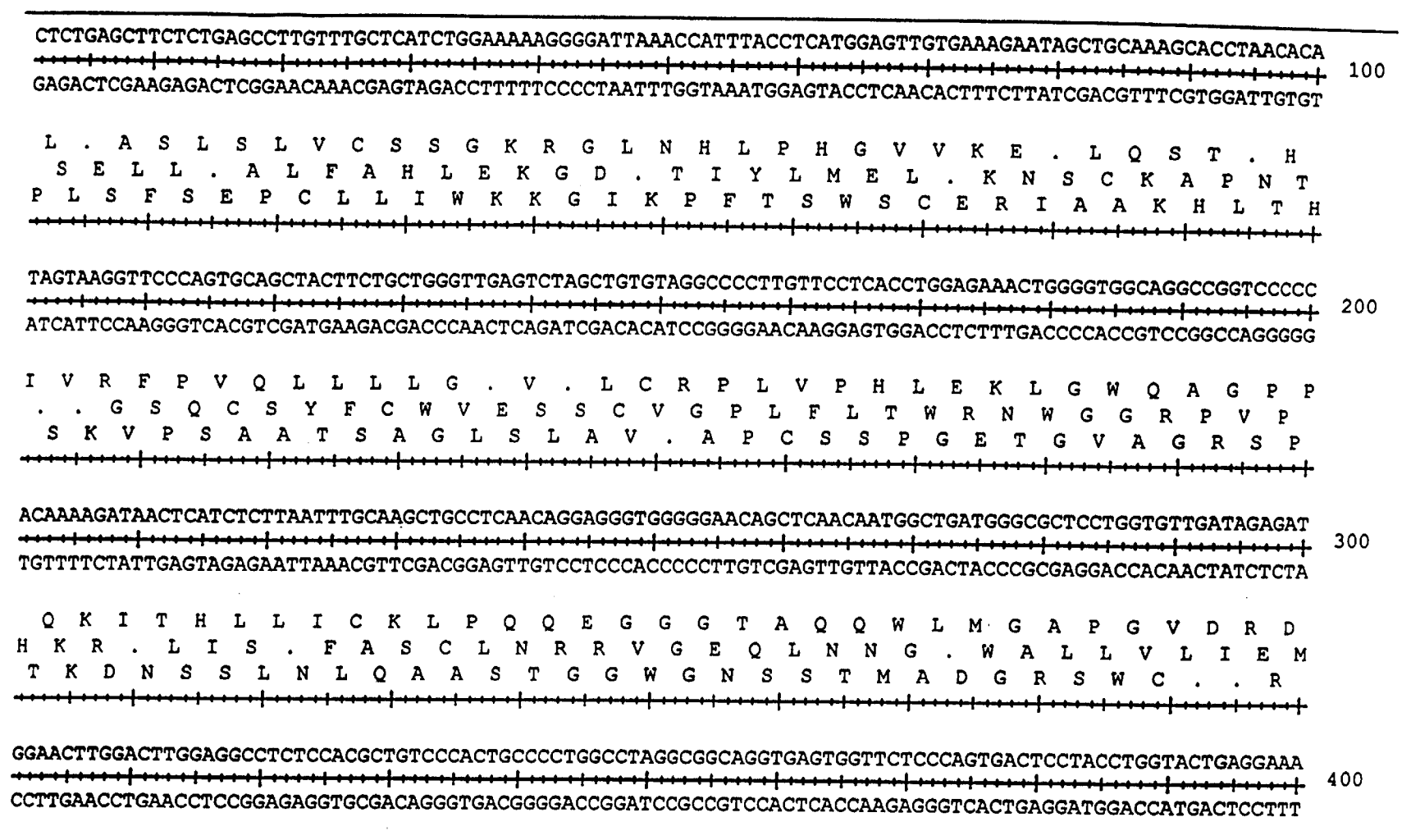
Figure 14B-1:
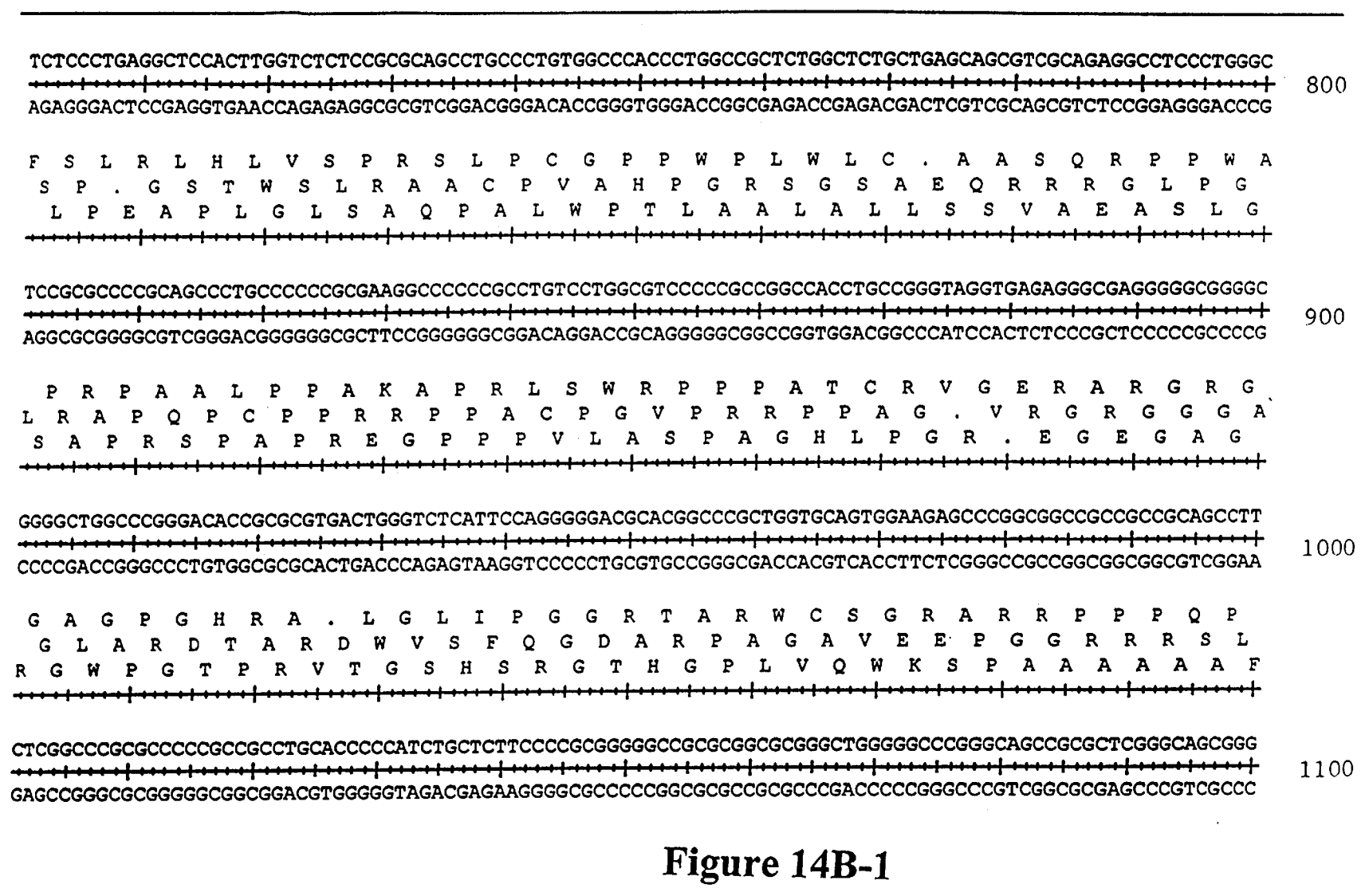
Figure 14C:
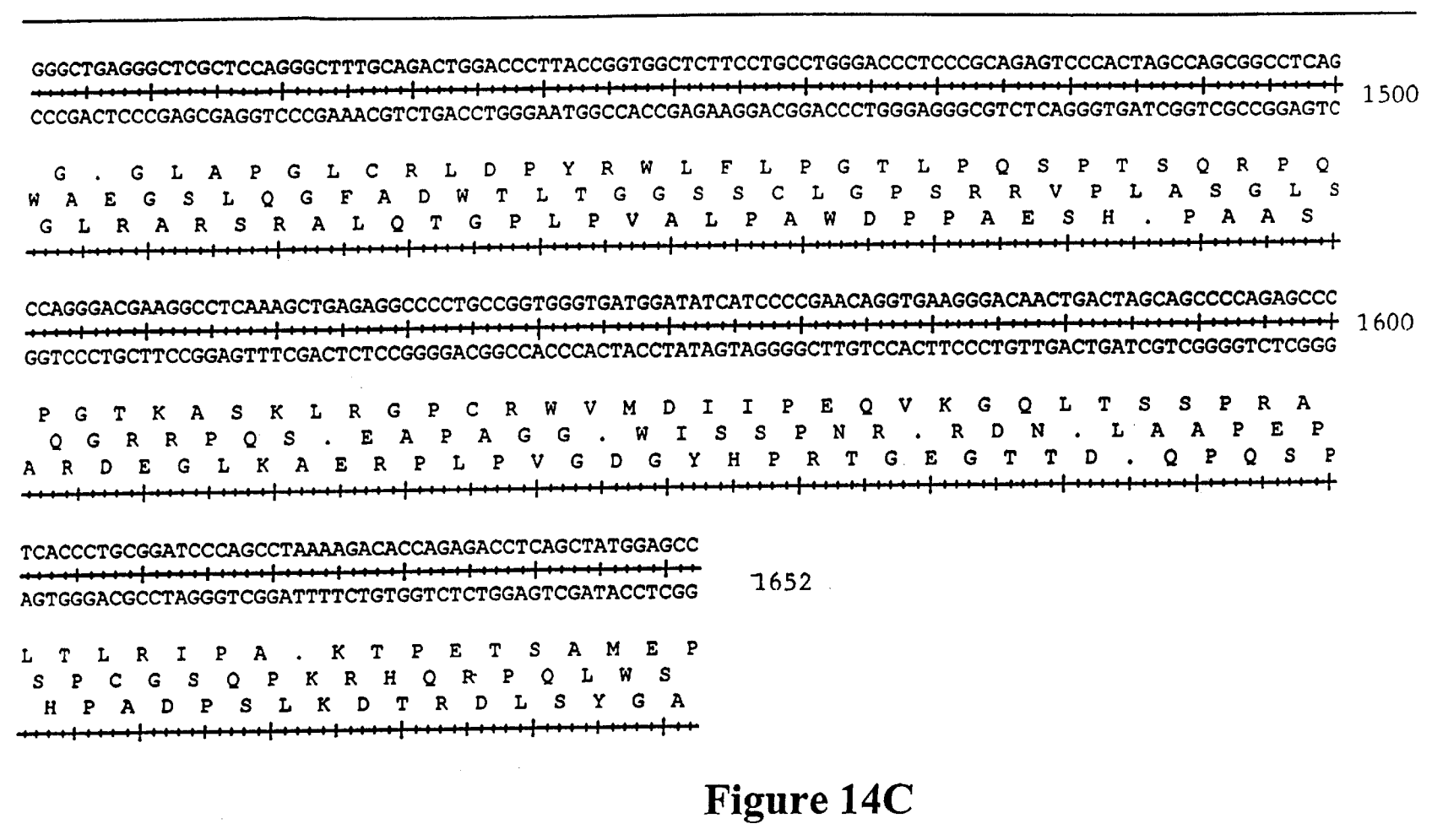

FIGS. 14A–C illustrate the human genomic sequence that encodes the artemin gene as shown in the top nucleotide sequence (SEQ ID NO:68), the complement of that sequence as shown in the bottom nucleotide sequence (SEQ ID NO:69), and the amino acid sequences encoded by the three reading frames of the artemin gene, wherein the top amino acid sequence is the sequence encoded by the reading frame starting at the first nucleotide of the top sequence, the second amino acid sequence is the sequence encoded by the reading frame starting at the second nucleotide of the top sequence, and the third amino acid sequence is the sequence encoded by the reading frame starting at the third nucleotide of the top sequence; the first peptide encoded by the top amino acid sequence (ASLSLVCSSGKRGLNHLPHGVVKE) is SEQ ID NO:70, the second peptide encoded by the top amino acid sequence (LQST) is SEQ ID NO:71, the third peptide encoded by the top amino acid sequence (HIVRFPVQLLLLG) is SEQ ID NO:72, the fourth peptide encoded by the top amino acid sequence (LCRPLVPHLEKLGWQAGPPQKITH-LLICK-LPQQEGGGTAQQWLMGAPGVDRDGTWTWRPLHA VPLPLA) is SEQ ID NO:81, and the last peptide encoded by the bottom amino acid sequence (QPQSPHPADPSLKDTRDLSYGA) is SEQ ID NO:118.

FIG. 15 illustrates the partial rat artemin cDNA coding sequence as shown in the top nucleotide sequence (SEQ ID NO:73), the complementary nucleotide sequence as shown in the bottom nucleotide sequence (SEQ ID NO:74), and the amino acid sequences encoded by the top sequence; wherein the first peptide (PVSALGLGHSS-DELIRFRFCSGSCRRARSPHDLSLASLLGAGALRSPP-GSRPISQ PCCRPTRYEAVS FMDVNSTWRTV-DHLSATACGCLG) is SEQ ID NO:75, the second peptide (SSSFCTLDPYVALPGTAPRGLTS) is SEQ ID NO:119, and the third peptide (EPQLNRK-LRPQADEGQTEPGKMTEPLTNSPKVFMDPSSTDSRN-LSY) is SEQ ID NO:120.

DESCRIPTION OF THE PREFERRED EMBODIMENTS

Figure 2B:
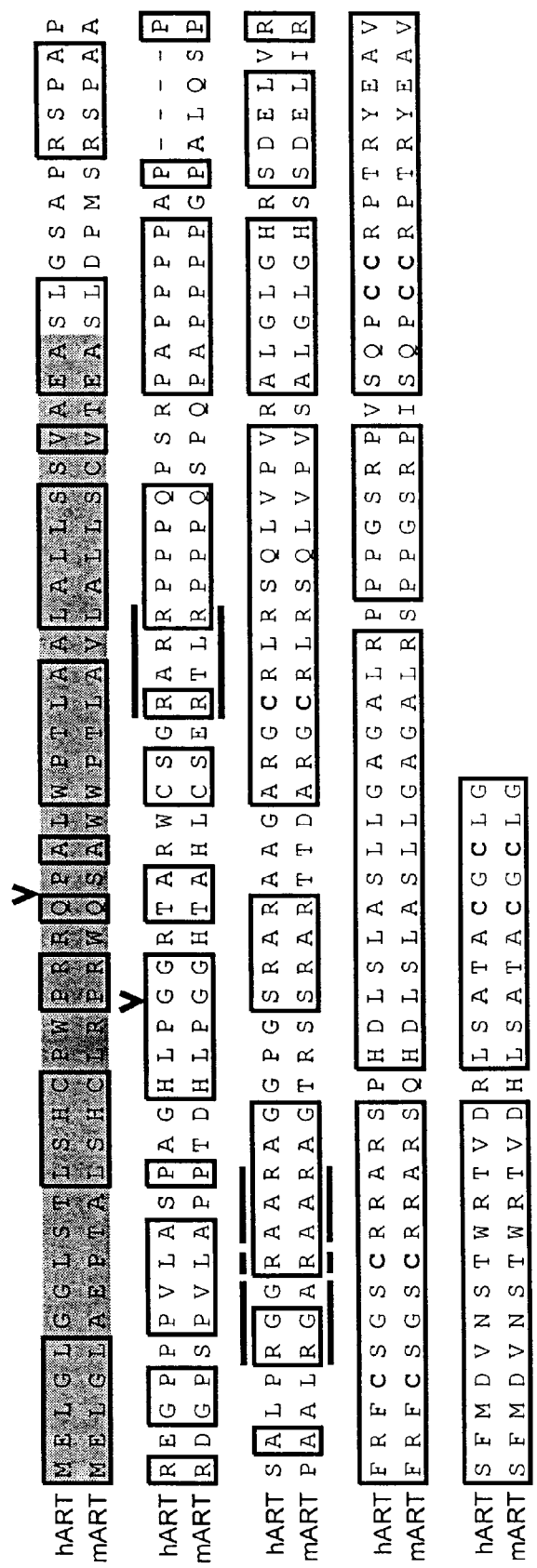
FIG. 2B illustrates the alignment of human and mouse pre-pro artemin (SEQ ID NOS:26 and 29, respectively) with the human and mouse putative signal sequence, pre-region, shaded (amino acids 1–39, SEQ ID NO:48 and SEQ ID NO:52, respectively), putative RXXR cleavage sites designated by thick lines, and arrowheads denoting the location of the two introns in the artemin gene.

The present invention is based upon the identification, isolation and sequencing of genomic and cDNA clones that encode a new member of the neurturin/persephin/GDNF ligand family identified herein as artemin (referenced in copending application Ser. No. 09/163,283, now abandoned, as GF4). The discovery of artemin follows that of neurturin which is described in copending U.S. application Ser. No. 08/775,414, now U.S. Pat. No. 6,090,778 which is incorporated in its entirety by reference, and persephin which is described in copending U.S. applications Ser. Nos. 08/981,739, now pending, and 08/931,858, now pending, both of which are incorporated in their entirety by reference.

Artemin promotes the survival of several peripheral and central neuronal populations in vitro, including sympathetic neurons, neural crest, placodally-derived sensory neurons, and dopaminergic midbrain neurons. Artemin activates both the GFRα3/RET and GRFα1/RET receptor complexes in vitro, but it is believed GFRα3/RET is the preferred multicomponent receptor for artemin signaling in vivo.

Figure 1A-1:
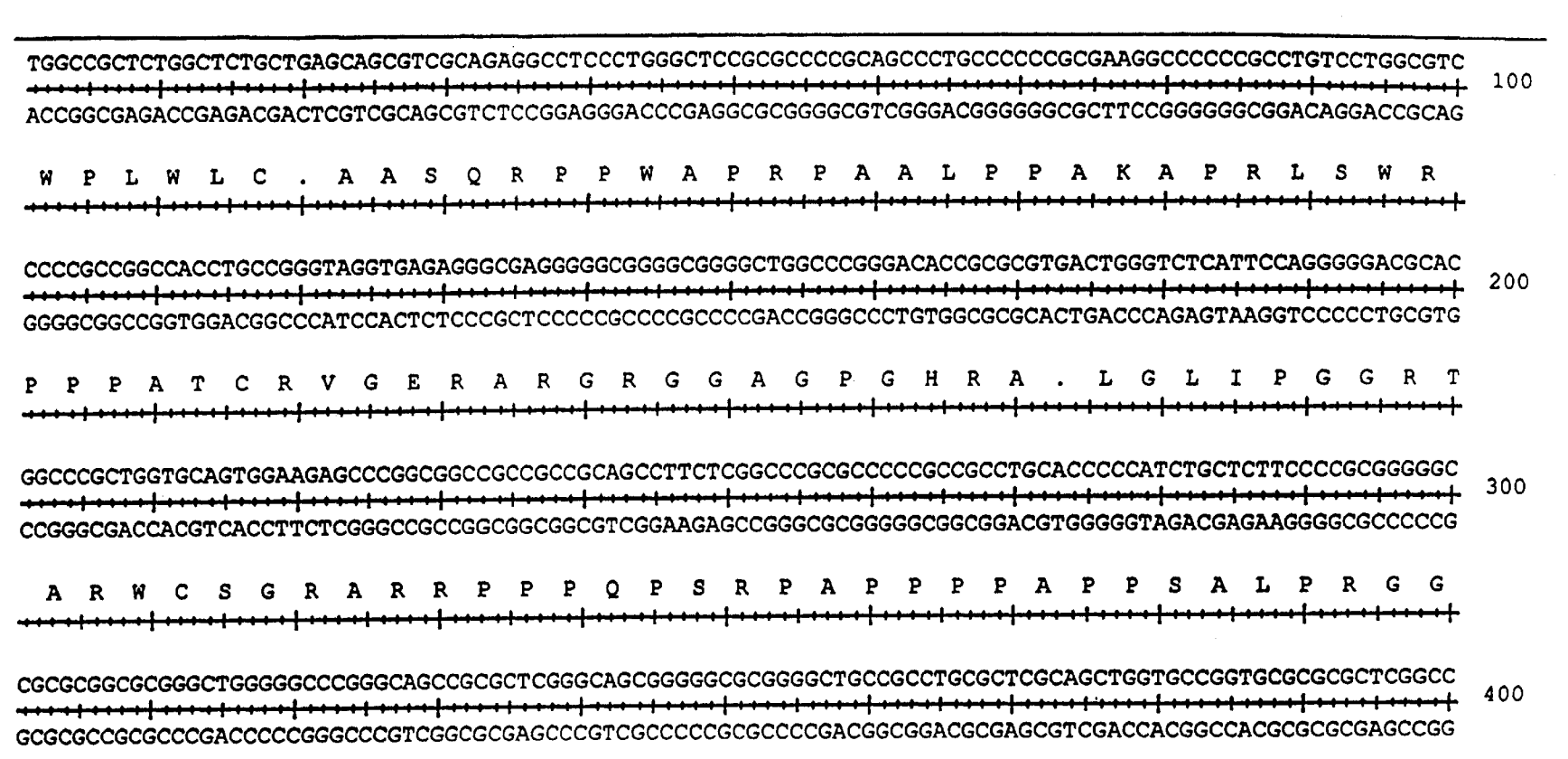
Figure 1B-1:
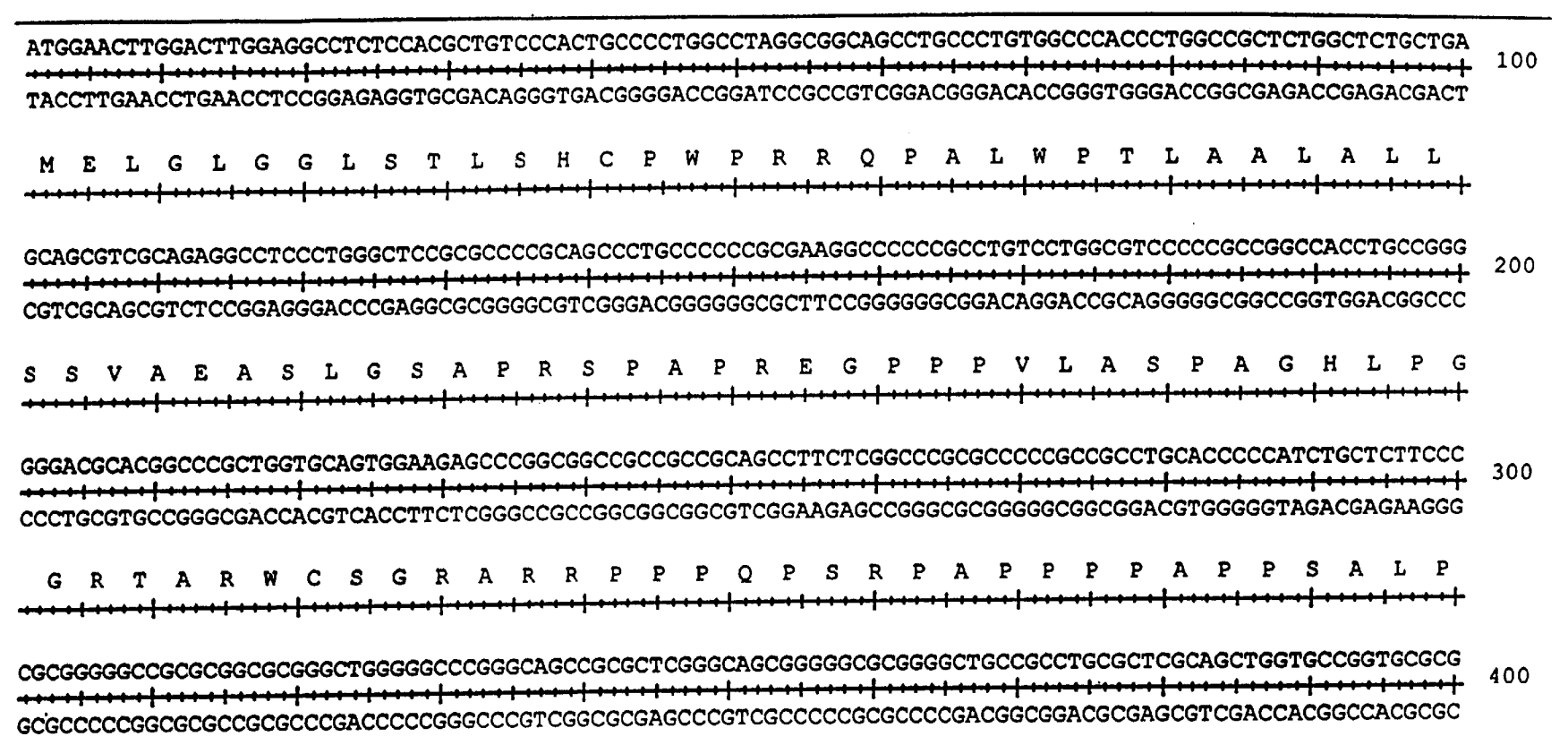
Figure 1B-2:
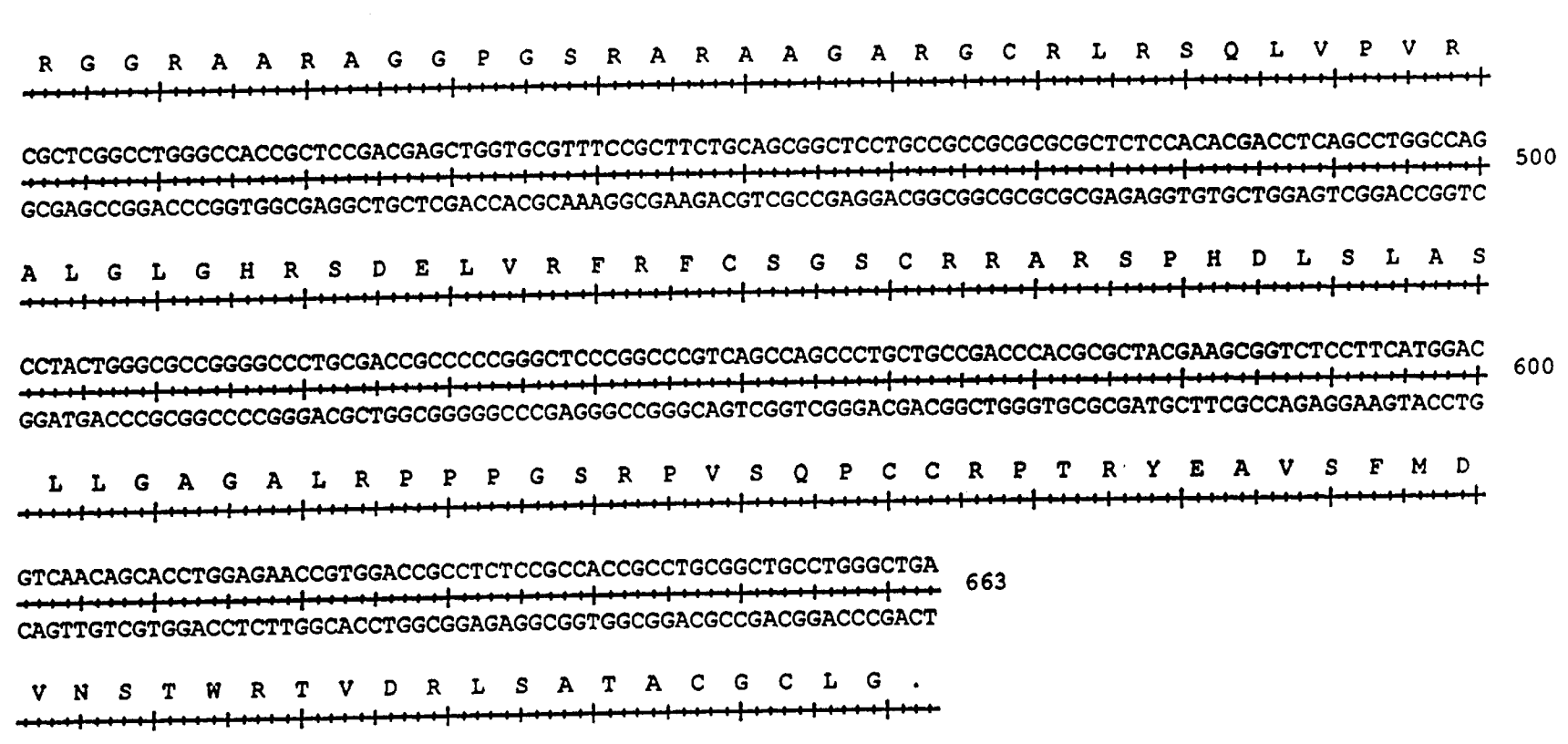
Figure 1D-2:
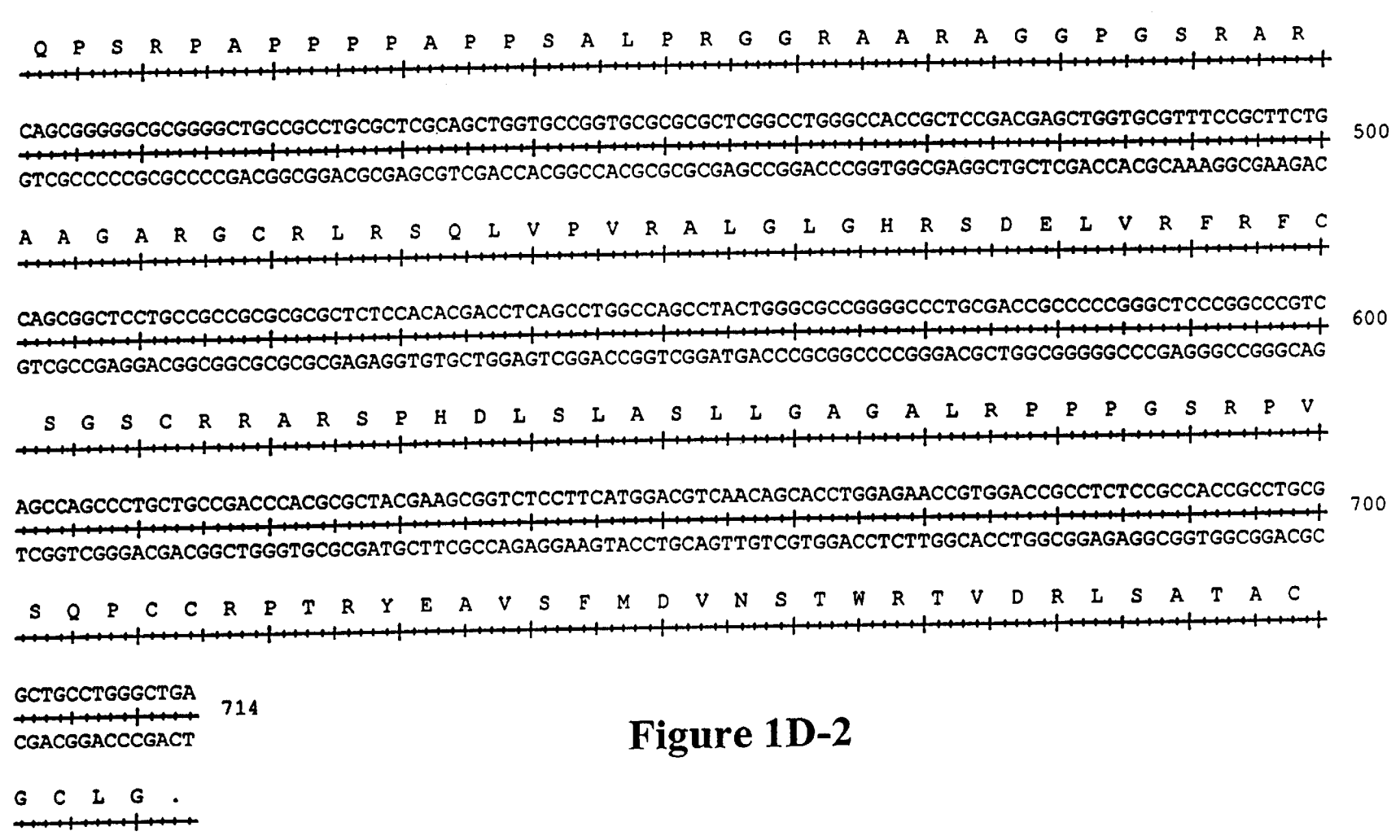

As described in more detail below, artemin was discovered by using the murine pre-pro neurturin amino acid sequence to scan the High Throughput Genome Sequences (hgts) database. This search identified two hgts sequences (AC005038 and AC005051) which had regions of DNA homologous to a DNA encoding pre-pro neurturin. Although, the hgts sequences were later discovered to have numerous sequence errors, i.e. omissions, additions and incorrect bases, one of the hgts sequences (AC005038) had a stretch of 197 nucleotides (nucleotides 67,464 to 67,660) which ultimately turned out to be identical to nucleotides 663–467 of the complementary strand of the Artemin nucleic acid (FIG. 1B) and the other (AC005051) had a stretch of 183 nucleotides (nucleotides 113,379 to 113,561) identical to nucleotides 648–468 of the complementary strand of the Artemin nucleic acid (FIG. 1B).

In order to determine whether the hgts sequences corresponded to coding regions of a new growth factor, oligonucleotide primers were designed based upon the hgts sequences to amplify overlapping polynucleotides of the suspected coding region from human genomic DNA. The overlapping polynucleotides were sequenced and this sequence information was combined with the hgts sequences to assemble the complementary genomic nucleotide sequences (SEQ ID NO:1–2) shown in FIG. 1A. One of the reading frames in SEQ ID NO: 1 encodes a partial pro-artemin amino acid sequence that extends from within a pro-domain including three potential RXXR proteolytic processing sites (encoded by the three sets of 12 nucleotides starting at positions 220, 292, and 301 of the top sequence of FIG. 1A) and terminates at the second glycine residue shown in the last line of FIG. 1A. Alignment of the predicted mature human artemin (hART) protein with the other GDNF ligands (FIG. 2A) confirmed that artemin represents a new member of the GDNF ligand family, with artemin being most similar to neurturin and persephin (~45% identity), and somewhat more divergent from GDNF (~36% identity). Primers designed from the human artemin genomic sequence were used to identify a clone containing the mouse artemin gene.

To isolate full length mRNA species encoding artemin, primers corresponding to the human and mouse artemin genomic sequences were used to perform rapid amplification of cDNA ends (RACE) PCR on multiple human and mouse tissue cDNA libraries. Analysis of the full-length cDNAs from human and mouse (FIGS. 1B and 1C) enabled the prediction of full-length human and mouse artemin proteins (FIGS. 1B, 1C and 2B) having a signal peptide for secretion (amino acids 1–39 of FIG. 2B), and a large pro-region separated from the mature region by multiple conserved RXXR furin protease cleavage sites (FIG. 2B). Comparison of the human mRNA sequence with the genomic locus revealed the presence of two introns in the artemin coding region (FIGS. 2B and 2C), the second of which is positioned similarly to the introns found in the pro-domains of other GDNF family ligands.

Reference to mature artemin herein is intended to be construed to include growth factors of any origin which are substantially homologous to and which are biologically equivalent to mature human and mouse artemin characterized and described herein. Such substantially homologous growth factors may be native to any tissue or species and, similarly, biological activity can be characterized in any of a number of biological assay systems. Reference to pre-pro-artemin is intended to be construed to include pre-pro growth factors containing a pre- or leader or signal sequence region, a pro-sequence region and a mature artemin amino acid sequence as defined herein. Reference to pro-artemin is intended to mean a polypeptide lacking the signal sequence region, but containing both a pro-region ending in an RXXR cleavage sequence and a mature artemin amino acid sequence.

The terms "biologically equivalent" are intended to mean that the compositions of the present invention are capable of demonstrating some or all of the same growth promoting properties in a similar fashion, although not necessarily to the same degree as the recombinantly produced human artemin identified herein.

By "substantially homologous" it is meant that the degree of sequence identity between artemin orthologs including human, mouse and artemin from any other species, is greater than that between paralogs such as human artemin and human neurturin or human artemin and human persephin, and greater than that reported previously for members of the TGF-β superfamily (for discussion of homology of TGF-β superfamily members see Kingsley, *Genes and Dev* 8:133–46, 1994).

Sequence identity or percent identity is intended to mean the percentage of same residues between two sequences aligned using the Clustal method (Higgins et al, *Cabios* 8:189–191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of protein Sequence and Structure*, Dayhoff, Ed., NBRF, Washington, Vol. 5, suppl. 3, p. 345, 1978).

To determine percent sequence identity between two sequences, the number of identical amino acids in the aligned sequences is divided by the total number of amino acids in the reference sequence. As used herein, the reference sequence is human artemin when determining its percent identity with mouse artemin and with the non-artemin growth factors, human neurturin, human GDNF or human persephin. Similarly, the reference sequence would be mouse artemin when determining its percent identity with mouse GDNF, mouse neurturin or mouse persephin and the reference sequence would be rat artemin when determining its percent identity with rat GDNF, rat neurturin and rat persephin. Referencing is to human neurturin when determining percent identity between human neurturin and non-human neurturin or between human neurturin and its human paralogs GDNF and persephin.

Percent conservation is calculated from the above alignment by adding the number of identical residues to the number of positions at which the two residues represent a conservative substitution (defined as having a log odds value of greater than or equal to 0.3 in the PAM250 residue weight table) and dividing by the total number of amino acids in the reference sequence. Preferred conservative amino acid changes are: R-K; E-D, Y-F, L-M; V-I, Q-H.

Table 1 shows the percent identity (I) and conservation (C) for comparisons of mature artemin, mature persephin, mature neurturin and mature GDNF from various species. Comparisons were made between mature human artemin (hART) and mature mouse artemin (mART) and between mature human artemin and mature human persephin (hPSP), mature human neurturin (hNTN) or mature human GDNF (hGDNF) using the alignments shown in FIGS. 2A and 2B and the preferred conservative substitutions stated above. The persephin and neurturin comparisons were made as described in copending application Ser. No. 08/931,858, now pending, with the first listed sequence being the reference sequence.

TABLE 1

| COMPARISON | % IDENTITY | % CONSERVATION |
| --- | --- | --- |
| hART v. mART | 88 | 90 |
| hART v. hPSP | 45 | 48 |
| hART v. hNTN | 49 | 51 |
| hART v. hGDNF | 36 | 40 |
| hPSP v. mPSP | 81 | 81 |
| hPSP v. rPSP | 80 | 81 |
| mPSP v. rPSP | 94 | 96 |
| hPSP v. hNTN | 49 | 50 |
| hPSP v. hGDNF | 40 | 43 |
| hNTN v. mNTN | 90 | 93 |
| hNTN v. rGDNF | 44 | 53 |
| hNTN v. mGDNF | 43 | 52 |
| hNTN v. hGDNF | 43 | 53 |
| mNTN v. rGDNF | 42 | 52 |
| mNTN v. mGDNF | 41 | 51 |
| mNTN v. hGDNF | 41 | 52 |

The sequence identity between human artemin and mouse artemin is about 88%. The persephin comparisons shown in Table 1 indicate that the identity between human persephin and mouse or rat persephin is about 80% whereas the degree of identity between mouse and rat persephin is about 94%. The neurturin comparisons in Table 1 indicate that mature mouse and human neurturin proteins have about 90% sequence identity. Furthermore, all artemin, persephin and neurturin orthologs of non-human mammalian species are believed to similarly have at least about 75% sequence identity with human artemin, human persephin, or human neurturin, respectively. For artemin, persephin or neurturin orthologs from non-mammalian species such as avian species, it is believed that the degree of homology with human artemin, human persephin, or human neurturin is at least about 65% identity.

By way of comparison, the variations between family members of the GDNF ligand family of growth factors can be seen by the comparisons shown in Table 1. For example, human artemin has about 49% sequence identity with human neurturin and about 36% sequence identity with human GDNF. Human persephin has about 49% sequence identity with human neurturin and about 40% sequence identity with human GDNF. Similarly, human neurturin has about 43% sequence identity with human GDNF. Thus, it is believed that any other member of the GDNF ligand family will have a similar sequence identity of about 40% of that of artemin, neurturin, persephin or GDNF of the same species and within a range of about 30% to about 60% sequence identity with artemin, neurturin, persephin or GDNF of the same species.

Based on the data in Table 1, a given member of the GDNF ligand family would be expected to have lesser sequence identity with any other family member of the same species than the sequence identity present in orthologs of that family member in other species just as human GDNF and human neurturin are more closely related to mouse GDNF and mouse neurturin, respectively, than to each other or to GDNF (see U.S. Pat. No. 5,739,307). Similarly, any given member of the GDNF ligand family would be expected to have greater sequence identity with another family member than to any other known member of the TGF-β superfamily (Kingsley, supra).

Figure 4:
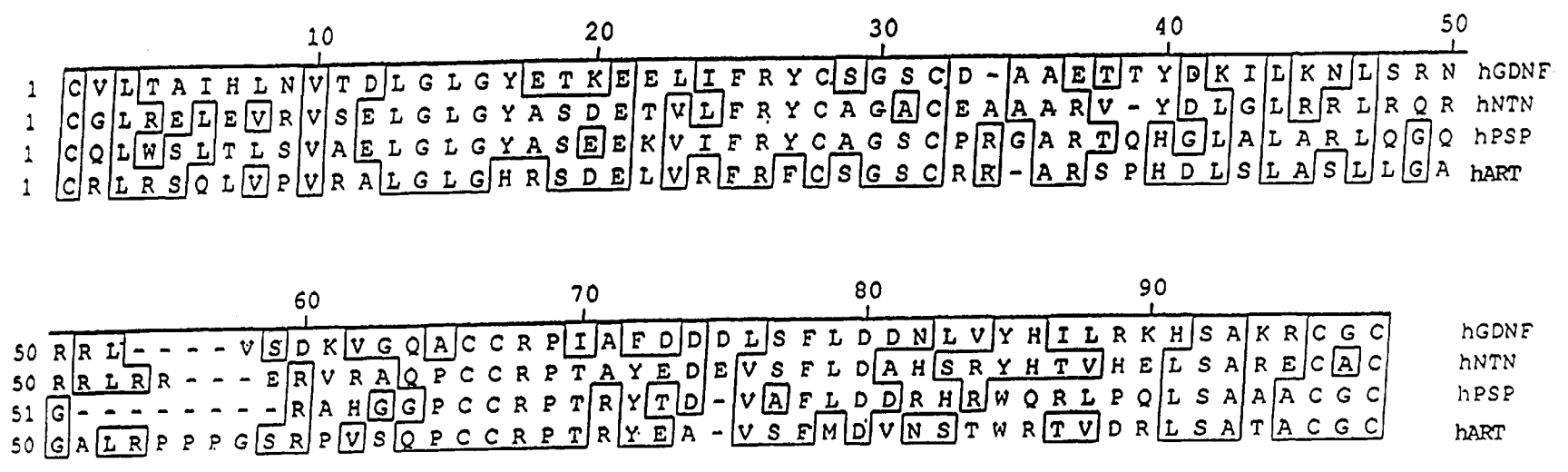

The conservation between members of the GDNF ligand family is also seen in FIG. 4, which shows an alignment, using the Clustal program described above, of the human sequences for GDNF, neurturin (NTN), persephin (PSP) and artemin (ART) from the first to the seventh framework cysteine residues. From this alignment, it is evident that arternin is closely related to the other family members in that artemin and persephin share 46 out of 96 residues (48%), artemin shares 48 out of 96 residues (50%) with neurturin, and artemin and GDNF share 36 out of 96 residues (38%).

Orthologs of pre-pro artemin in non-human mammalian species can be identified by virtue of the mature portion of the amino acid sequence having at least about 75% sequence identity with one of the predicted mature human artemin sequences disclosed herein and nonmammalian orthologs of pre-pro artemin can be identified by virtue of the mature portion of the amino acid sequence having at least about 65% identity with a mature human artemin sequence.

Also included within the meaning of substantially homologous is any artemin polypeptide which may be isolated by virtue of cross-reactivity with antibodies specific to human artemin or whose encoding nucleotide sequences, including genomic DNA, mRNA or cDNA may be isolated through hybridization with the complementary sequences shown in FIGS. 1–3 or fragments thereof. It will also be appreciated by one skilled in the art that degenerate DNA sequences can encode human artemin and these are also intended to be included within the present invention.

Conservatively substituted artemin proteins retaining the biological activity of naturally occurring artemin are also within the scope of the present invention. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H.

As used herein, an artemin polypeptide can also include modifications of the artemin sequences identified herein, including sequences in which one or more amino acids have been inserted, deleted or replaced with a different amino acid or a modified or unusual amino acid, as well as modifications such as glycosylation or phosphorylation of one or more amino acids so long as the polypeptide containing the modified sequence retains the biological activity of artemin. Inserted or deleted amino acid(s) can be added to or removed from the N-terminus, C-terminus or within the naturally-occurring amino acid sequence. By retaining the biological activity, it is meant that the modified polypeptide can bind to and activate GRFα1/RET and/or GFRα3/RET expressed by a cell, although not necessarily at the same level of potency as that of the mature human artemin polypeptide identified herein. Assays for testing such activation are known in the art and include the Gal4-Elk/Gal4-Luc reporter system described in Example 7 below. The term "trophic support" is used herein to mean that a growth factor such as artemin provides nourishment to a cell such that the cell maintains or recovers at least one of its normal functions.

It is intended that the term artemin polypeptide also includes naturally occurring allelic variants of the human artemin sequences disclosed herein. For example, cDNAs encoding a second starting methionine were identified by RACE PCR from some human cDNA libraries and would encode the pre-pro-artemin shown in FIG. 1D (SEQ ID NO:32). However, mature artemin generated from this variant would be identical to the mature human artemin shown in FIG. 3A (SEQ ID NO:3).

Fragments of artemin are also encompassed by the present invention. Such fragments may be of any length but preferably retain the biological activity of artemin or are antigenic. The minimum length of such biologically active or antigenic fragments can readily be determined by those skilled in the art using known techniques. Preferably, the minimum length of fragments of artemin is at least 8 amino acids, more preferably, at least 10 amino acids, still more preferably at least 12 amino acids, even still more preferably at least 15 amino acids and most preferably, at least 20 amino acids or greater. One fragment of artemin which is believed to retain the survival promoting activity of artemin begins at the first conserved cysteine residue and ends at the seventh conserved cysteine residue (FIG. 4, SEQ ID NO:19 (human) or SEQ ID NO:33 (mouse)). Antigenic fragments are capable of eliciting artemin-specific antibodies when administered to a host animal and includes those smaller fragments that require conjugation to a carrier molecule to be immunogenic. Typically, antigenic fragments will be at least 5 or 6 amino acids in length and may be any length up to the length of mature artemin, preferably an antigenic fragment is 8, more preferably 10, still more preferably 12 amino acids in length, even still more preferably 15 amino acids in length and most preferably 20 amino acids or more in length.

It is also believed that particular discrete fragments of artemin, or analogues thereof, can serve as an agonist where the fragment activates an artemin receptor, such as GFRα3/RET or GRFα1/RET, to elicit the survival or growth promoting action on a target cell, or other artemin fragments or analogues can serve as antagonists to artemin where they bind to, but do not activate, the receptor or do not promote survival and growth. Such fragments or analogues that are agonists and those that are antagonists are also within the scope of the present invention.

Although it is not intended that the inventors herein be bound by any theory, it is thought that the human artemin protein identified herein as well as orthologs from other tissues and species may exist as dimers in their biologically active form in a manner consistent with what is known for other factors of the TGF-β superfamily.

In addition to homodimers, the monomeric units of artemin dimers can be used to construct stable growth factor heterodimers or heteromultimers comprising at least one monomer unit of artemin. This can be done by dissociating a homodimer of artemin into its component monomeric units and reassociating in the presence of a monomeric unit of a second or subsequent homodimeric growth factor. This second or subsequent homodimeric growth factor can be selected from a variety of growth factors including neurturin, GDNF, persephin, a member of the NGF family such as NGF, BDNF, NT-3 and NT-4/5, a member of the TGF-β superfamily, a vascular endothelial growth factor, a member of the CNTF/LIF family and the like. By forming heterodimers or heteromultimers of artemin and one or more other growth factors, the resultant hybrid growth factor would be expected to be able to bind to at least two distinct receptor types preferentially having a different tissue distribution. The resultant heterodimers or heteromultimers would be expected to show a different and, possibly, an enlarged spectrum of cells upon which it could act or to provide greater potency. It is also possible that the heterodimer or heteromultimer might provide synergistic effects not seen with homodimers or homomultimers. For example, the combination of factors from different classes has been shown to promote long-term survival of oligodendrocytes whereas single factors or combinations of factors within the same class promoted short-term survival (Barres et al., *Development* 118:283–295, 1993).

Heterodimers can be formed by a number of methods. For example, homodimers can be mixed and subjected to conditions in which dissociation/unfolding occurs, such as in the presence of a dissociation/unfolding agent, followed by subjection to conditions which allow monomer reassociation and formation of heterodimers. Dissociation/unfolding agents include any agent known to promote the dissociation of proteins. Such agents include, but are not limited to, guanidine hydrochloride, urea, potassium thiocyanate, pH lowering agents such as buffered HCl solutions, and polar, water miscible organic solvents such as acetonitrile or alcohols such as propanol or isopropanol. In addition, for homodimers linked covalently by disulfide bonds as is the case with TGF-β family members, reducing agents such as dithiothreitol and β-mercaptoethanol can be used for dissociation/unfolding and for reassociation/refolding.

Heterodimers can also be made by transforming a cell with two or more factors such that the transformed cell produces heterodimers as has been done with the neurotrophins. (Heymach and Schooter, *J Biol Chem* 270:12297–12304, 1995). Another method of forming heterodimers is by combining artemin homodimers and a homodimer from a second growth factor and incubating the mixture at 37° C.

When heterodimers are produced from homodimers, the heterodimers may then be separated from homodimers using methods available to those skilled in the art such as, for example, by elution from preparative, non-denaturing polyacrylamide gels. Alternatively, heterodimers may be purified using high pressure cation exchange chromatography such as with a Mono S cation exchange column or by sequential immunoaffinity columns.

It is well known in the art that many proteins are synthesized within a cell with a signal sequence at the N-terminus of the mature protein sequence and the protein carrying such a leader sequence is referred to as a preprotein. The pre-portion of the protein is cleaved during cellular processing of the protein. In addition to a pre-leader sequence, many proteins contain a distinct pro sequence that describes a region on a protein that is a stable precursor of the mature protein. Proteins synthesized with both pre- and pro-regions are referred to as preproproteins. In view of the processing events known to occur with other TGF-β family members, the inventors believe that the form of the artemin protein as synthesized within a cell is the pre-pro-artemin.

Human and mouse pre-pro-artemin polypeptides are believed to preferably contain an N-terminal methionine of a signal sequence (pre-region) of 39 amino acids (FIG. 2B; SEQ ID NOS:48 and 49, respectively; amino acids 1–39 of SEQ ID NOS:26 and 29, respectively). It is known that the full length of a leader sequence is not necessarily required for the sequence to act as a signal sequence and, therefore, within the definition of pre-region of artemin is included fragments thereof, usually N-terminal fragments, that retain the property of being able to act as a signal sequence, that is to facilitate co-translational insertion into the membrane of one or more cellular organelles such as endoplasmic reticulum, mitochondria, golgi, plasma membrane and the like. It is also possible that the pre-pro-artemin polypeptide might have one or more isoforms having an N-terminal Leucine, inasmuch as isoforms of another growth factor, human fibroblast growth factor-2, have alternative initiations of translation at CUG start codons in addition to AUG (Arnaud et al., *Molecular and Cellular Biology* 19:505–514, 1999). Thus, isoforms of pre-pro-artemin could begin, for example, before the methionine (the first amino acid shown in FIG. 1B) with the start point being at the CTG codon beginning at nucleotide 284 in the genomic human artemin sequence (see FIG. 14) or after the same methionine with the start point being the CTG codon beginning at nucleotide 329 so long as the pre-region of the isoform can serve as a signal sequence. All such isoforms are within the scope of the present invention.

Moreover, also within the scope of the present invention are polypeptides containing a non-artemin pre-pro-region and a mature artemin as well as polynucleotides encoding such polypeptides. The polypeptides can generate a mature artemin upon cleavage of the non-artemin pre-pro-region and the polynucleotides can be used in an expression system to produce the polypeptide which upon cleavage of the non-artemin pre-pro-region yields mature artemin. Such non-artemin pre-pro-region polypeptides and encoding polynucleotides are well known in the art and, preferably, include a pre-pro-region from another growth factor such as neurturin or persephin although any pre-pro-region can be used so long as it functions as a pre-pro-region as described herein. The artemin pre-region is followed by a pro-domain which is believed to preferably terminate with an RXXR consensus site immediately before the N-terminal amino acid of mature artemin. Thus, mature human and mouse artemin are believed to be preferably generated by proteolytic cleavage of human and mouse pro-artemin (SEQ ID NOS:40 and 41, respectively) after one of the three RXXR consensus sequences shown in FIGS. 1A and 2B, (RARR, RGGR and RAAR for human and RTLR, RGAR and RAAR for mouse) although it is possible that cleavage could occur at some other, non-consensus site to produce additional isoforms. All such isoforms are included within the scope of the present invention.

Figure 3A:
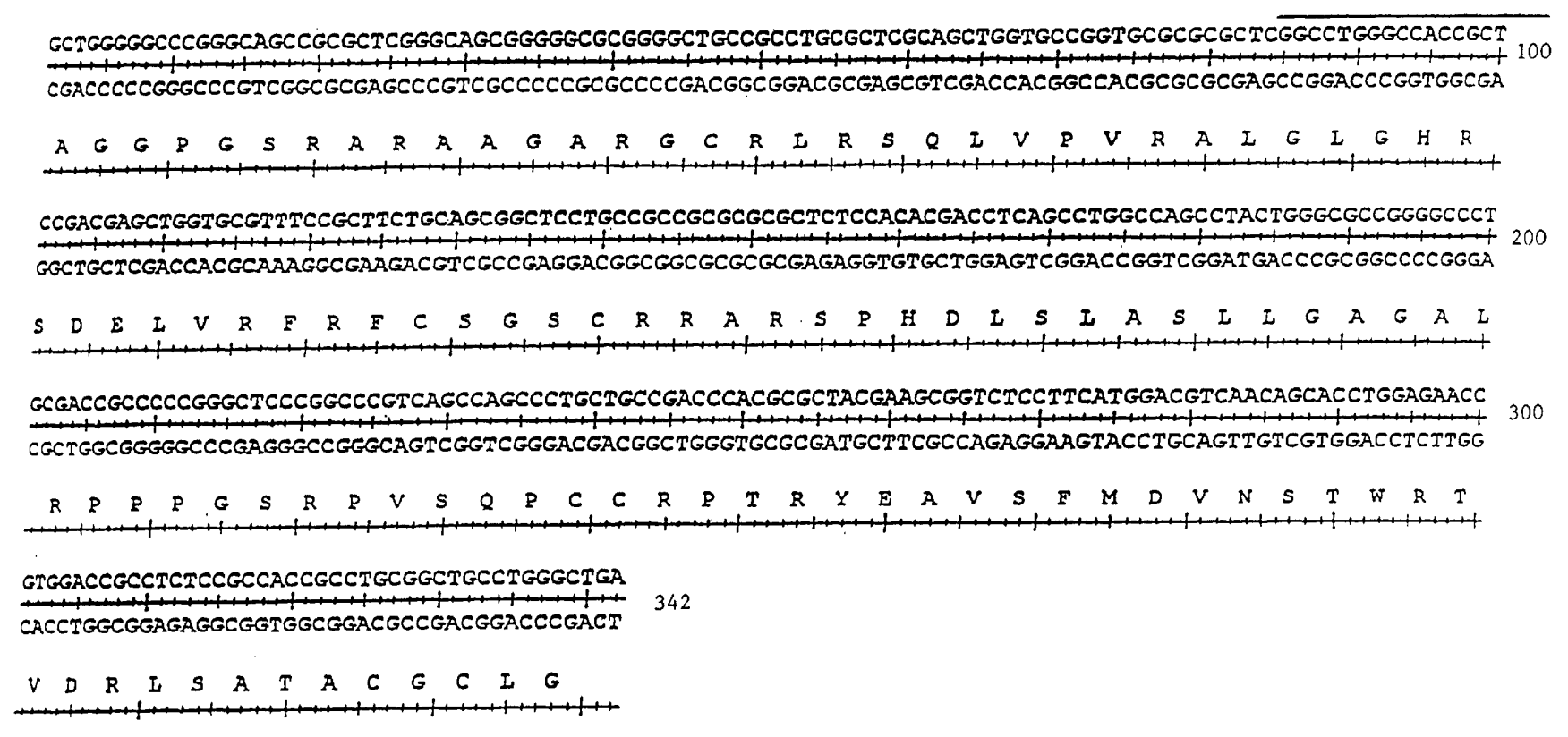
Figure 3C:
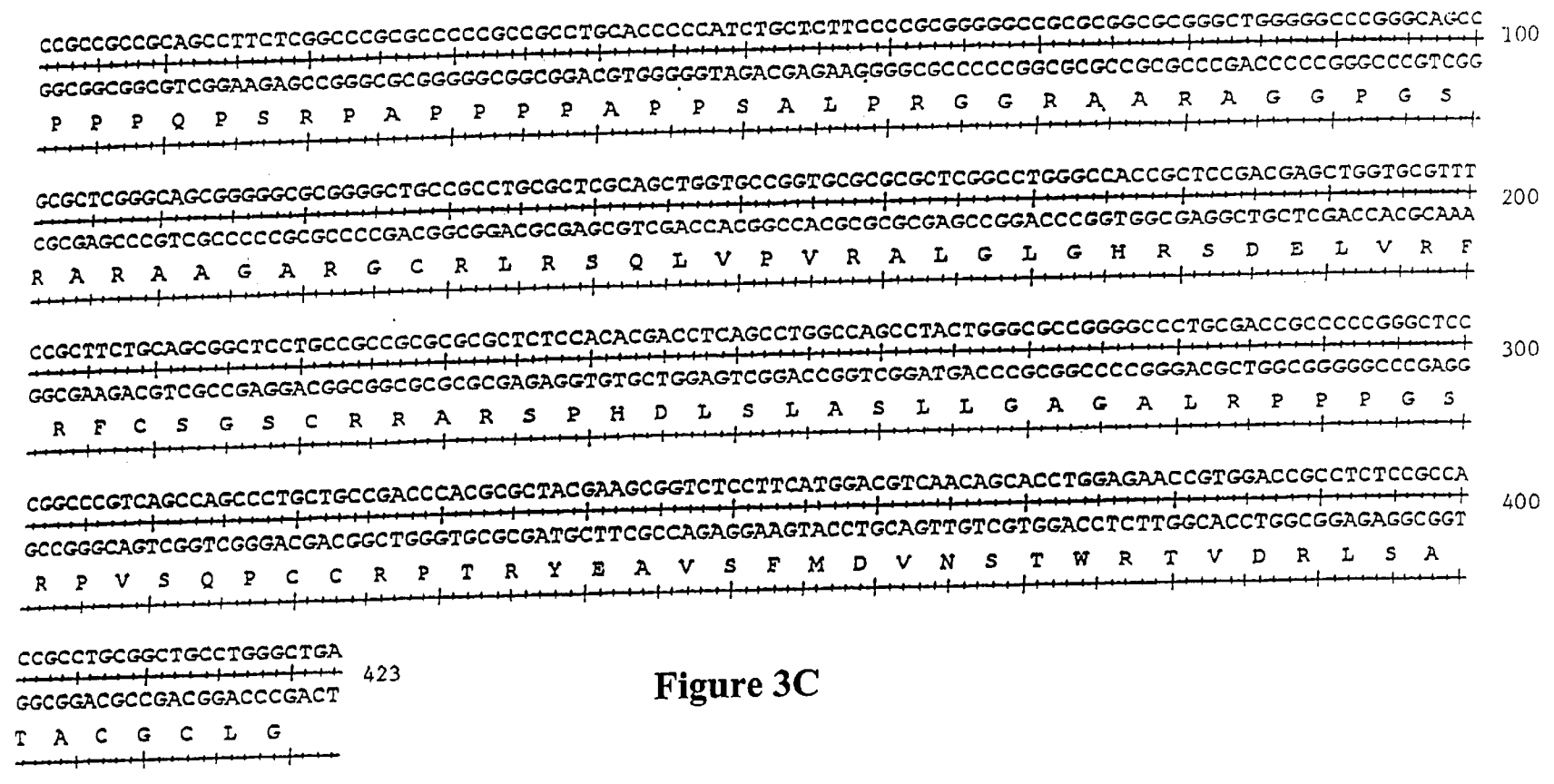

Cleavage after the first RXXR sequence following the N-terminus of human pro-artemin will generate the mature polypeptide shown in FIG. 3C (SEQ ID NO:5). Similarly, cleavage after the second and third RXXR sequences will generate the mature human polypeptides shown in FIGS. 3B (SEQ ID NO:4) and 3A (SEQ ID NO:3), respectively. By analogy, predicted mature mouse artemin sequences are SEQ ID NOS:34, 35 and 36. Based on the biological assays described below, the preferred mature human artemin consists of SEQ ID NO:3 and similarly, the preferred mature mouse artemin consists of SEQ ID NO:34, respectively. The preferred human pro-region polypeptide would thus comprise amino acids 40–107 of FIG. 2B (SEQ ID NO:50) and the corresponding preferred mouse pro-region polypeptide would comprise amino acids 40–111 of FIG. 2B (SEQ ID NO:51). Similarly the preferred human pre-pro-region polypeptide would thus comprise amino acids 1–107 of FIG. 2B (SEQ ID NO:52) and the corresponding preferred mouse pre-pro-region polypeptide would comprise amino acids 1–111 of FIG. 2B (SEQ ID NO:53). The mature, secreted artemin molecule is likely to form a disulfide linked homodimer by analogy to other members of the TGF-β family.

The human and mouse preferred pre-region polynucleotides comprise nucleotides 1–117 of FIG. 1B (SEQ ID NO:54) and nucleotides 1–117 of FIG. 1C (SEQ ID NO:55), respectively; the human and mouse pro-region polynucleotides comprise nucleotides 118–321 of FIG. 1B (SEQ ID NO:56) and nucleotides 118–333 of FIG. 1C (SEQ ID NO:57), respectively; and the human and mouse pre-pro-region polynucleotides comprise nucleotides 1–321 of FIG. 1B (SEQ ID NO:58) and nucleotides 1–333 of FIG. 1C (SEQ ID NO:59), respectively. It is noted, however, that alternative start points and alternative non-consensus cleavage points as discussed above would result in coding sequences corresponding to the alternative isoforms of pre-pro-artemin and mature artemin.

A preferred artemin according to the present invention is prepared by recombinant DNA technology although it is believed that artemin can be isolated in purified form from cell-conditioned medium as was done for neurturin.

By "pure form" or "purified form" or "substantially purified form" it is meant that an artemin composition is substantially free of other proteins which are not artemin. Preferably, a substantially purified artemin composition comprises at least about 50 percent artemin on a molar basis compared to total proteins or other macromolecular species present. More preferably, a substantially purified artemin composition will comprise at least about 80 to about 90 mole percent of the total protein or other macromolecular species present and still more preferably, at least about 95 mole percent or greater.

Recombinant artemin may be made by expressing the DNA sequences encoding artemin in a suitable transformed host cell. Using methods well known in the art, the DNA encoding artemin may be linked to an expression vector, transformed into a host cell and conditions established that are suitable for expression of artemin by the transformed cell.

Any suitable expression vector may be employed to produce recombinant artemin such as, for example, the mammalian expression vector pCB6 (Brewer, *Meth Cell Biol* 43:233–245, 1994) or the *E. coli* pET expression vectors, specifically, pET-30a (Studier et al., *Methods Enzymol* 185:60–89, 1990). Other suitable expression vectors for expression in mammalian and bacterial cells are known in the art as are expression vectors for use in yeast or insect cells. Baculovirus expression systems can also be employed.

A number of cell types may be suitable as host cells for expression of recombinant artemin. Mammalian host cells include, but are not limited to, monkey COS cells, Chinese Hamster Ovary (CHO) cells, human kidney 293 cells, human epidermal A431 cells, human Colo 205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK and Jurkat cells. Yeast strains that may act as suitable host cells include *Saccharomyces cerevisiae, Schizosaccharomyces pombe,* Kluyveromyces strains, Candida, and any other yeast strain capable of expressing heterologous proteins. Host bacterial strains include *Escherichia coli, Bacillus subtilis, Salmonella typhimurium* and any other bacterial strain capable of expressing heterologous proteins. If the polypeptide is made in yeast or bacteria, it may be necessary to modify the polypeptide, for example, by phosphorylation or glycosylation of the appropriate sites using known chemical or enzymatic methods, to obtain a biologically active polypeptide.

The polypeptide of the invention can also be expressed in transgenic plants (see, for example, U.S. Pat. No. 5,679,880) or transgenic animals such as, for example, cows, goats, pigs, or sheep whose somatic or germ cells contain a nucleotide sequence encoding human artemin.

The expressed artemin polypeptide can be purified using known purification procedures, such as gel filtration and ion exchange chromatography. Purification may also include affinity chromatography using an agent that will specifically bind the artemin polypeptide, such as a polyclonal or monoclonal antibody raised against a mature artemin or fragment thereof. Other affinity resins typically used in protein purification may also be used such as concanavalin A-agarose, heparin-toyopearl® or Cibacrom blue 3GA Sepharose®. Purification of artemin can also include one or more steps involving hydrophobic interaction chromatography using such resins as phenyl ether, butyl ether, or propyl ether.

It is also contemplated that an artemin polypeptide may be expressed as a fusion protein to facilitate purification. Such fuision proteins, for example, include an artemin amino acid sequence fused to a histidine tag such as when expressed in the pET bacterial expression system as well as the artemin amino acid sequence fused to the amino acid sequence of maltose binding protein (MBP), glutathione-S-transferase (GST) or thioredoxin (TRX). Similarly, the polypeptide of the invention can be tagged with a heterologous epitope and subsequently purified by immunoaffinity chromatography using an antibody that specifically binds such epitope. Kits for expression and purification of such fusion proteins and tagged proteins are commercially available.

Artemin and fragments thereof may also be produced by chemical synthesis using methods known to those skilled in the art.

Artemin may be expressed in the monomeric units or such monomeric form may be produced by preparation under reducing conditions. In such instances refolding and renaturation can be accomplished using one of the agents noted above that is known to promote dissociation/association of proteins. For example, the monomeric form can be incubated with dithiothreitol followed by incubation with oxidized glutathione disodium salt followed by incubation with a buffer containing a refolding agent such as urea.

Because multiple RXXR cleavage sites are present in the pro-artemin sequence, it is believed that isoforms of mature artemin exist. In addition, alternative non-consensus cleavage sites might also result in different isoforms. Thus, the mature artemin polypeptide may have a variable number of amino acids preceding the first canonical cysteine. Such alternate cleavage sites could be utilized differently among different organisms and among different tissues of the same organism. The N-terminal amino acids preceding the first of the seven conserved cysteines in the mature forms of members of the TGF-β family vary greatly in both length and sequence. Furthermore, insertion of a ten amino acid sequence two residues upstream of the first conserved cysteine does not affect the known biological activities of one family member, dorsalin (Basler et al., *Cell* 73:687–702, 1993). By analogy, it is believed that artemin proteins containing sequences of different lengths preceding the first canonical cysteine may exist or could be made and that these would retain their biological activity.

The present invention also encompasses isolated polynucleotides comprising nucleotide sequences that encode any of the human and mouse artemin polypeptides described herein. As used herein, a polynucleotide includes DNA and/or RNA and thus the nucleotide sequences recited in the Sequence Listing as DNA sequences also include the identical RNA sequences with uracil substituted for thymine residues. Nucleotide sequences included in the invention are those encoding the human and mouse pre-pro-artemin amino acid sequences shown in FIGS. 1B and 1C, respectively, as well as nucleotide sequences encoding the variant human artemin protein shown in FIG. 1D and nucleotide sequences encoding human and mouse pro-artemin (SEQ ID NOS:40 and 41, respectively). Preferred polynucleotides which encode human pre-pro- and pro-artemin comprise SEQ ID NOS:24 and 42, respectively, and preferred polynucleotides encoding mouse pre-pro- and pro-artemin comprise SEQ ID NOS:27 and 43, respectively. Polynucleotides within the scope of this invention do not include isolated chromosomes.

The invention also includes polynucleotides comprising a nucleotide sequence that encodes a mature artemin polypeptide such as mature human and mouse polypeptides consisting of any of SEQ ID NOS:3–5 and SEQ ID NOS:34–36, respectively. Such polynucleotides encoding mature artemin include the human nucleotide sequences set forth in SEQ ID NOS:6–8 and the mouse nucleotide sequences set forth in SEQ ID NOS:37–39. A particularly preferred polynucleotide encodes SEQ ID NO:3 and comprises SEQ ID NO:6.

It is understood by the skilled artisan that degenerate nucleotide sequences can encode the artemin amino acid sequences described herein and these are also intended to be included within the present invention. For example, SEQ ID NO:44 represents the artemin coding sequence found in one human cDNA clone isolated by the inventors herein which contains G rather than A at position 582, but which does not change the encoded amino acid sequence. Such degenerate nucleotide sequences include modifications of naturally-occurring sequences in which at least one codon is substituted with a corresponding redundant codon preferred by a given host cell, such as *E. coli* or insect cells, so as to improve expression of recombinant artemin therein.

The present invention also encompasses vectors comprising an expression regulatory element operably linked to any of the artemin-encoding nucleotide sequences included within the scope of the invention. This invention also includes host cells, of any variety, that have been transformed with such vectors.

In yet another embodiment, a polynucleotide which specifically hybridizes to a human artemin-encoding polynucleotide or to its complement is provided. Specific hybridization is defined herein as the formation of hybrids between a polynucleotide, including oligonucleotides, and a specific reference polynucleotide (e.g., a polynucleotide comprising a nucleotide sequence complementary to a nucleotide sequence encoding human artemin) wherein the polynucleotide preferentially hybridizes to the specific reference polynucleotide over other non-artemin polynucleotides. Specifically hybridizing oligonucleotides are typically at least 15 nucleotides in length and are preferably at least 17 to at least 20 nucleotides long. Other preferred lengths include at least 22 to at least 25 nucleotides. A polynucleotide that specifically hybridizes to a reference sequence can be of any length, for example, about 15 nucleotides up to about 100 nucleotides or up to about 1000 nucleotides or up to about 10,000 nucleotides or even greater. Specific hybridization is preferably done under high stringency conditions which, as well understood by those skilled in the art, can readily be determined by adjusting several factors during hybridization and during the washing procedure, including temperature, ionic strength, length of hybridization or washing times, and concentration of formamide (see for example, Sambrook, Fritsch and Maniatis., *Molecular Cloning: a Laboratory Manual*, 2d Ed., Vols. 1–3, Cold Spring Harbor Laboratory Press, Plainview N.Y. 11803, 1989)

The present invention also includes nucleic acid sequences which encode for artemin polypeptides that have survival or growth promoting activity and that preferentially bind anti-human or anti-mouse artemin antibodies over other antibodies that do not bind to human or mouse artemin.

Methods are also provided herein for producing artemin. Preparation can be by isolation from conditioned medium from a variety of cell types so long as the cell type produces artemin. A second and preferred method involves utilization of recombinant methods by isolating a nucleic acid sequence encoding artemin, cloning the sequence along with appropriate regulatory sequences into suitable vectors and cell types, and expressing the sequence to produce artemin.

On the basis of the structural similarities of artemin to the sequences of neurturin, GDNF and persephin, artemin would be expected to promote the survival and growth of neuronal as well as non-neuronal cells. As discussed above, GDNF, neurturin and persephin influence a broad spectrum of neuronal populations in the peripheral and central nervous systems. Moreover, all other growth factors isolated to date have been shown to act on many different cell types (for example see Scully and Otten, *Cell Biol Int* 19:459–469, 1005; Hefti, *Neurotrophic Factor Therapy* 25:1418–1435, 1994 which are incorporated by reference). As an example of the actions of neurotrophic factors on non-neuronal tissues, the prototypical neurotrophic factor, NGF, also acts upon mast cells to increase their number when injected into newborn rats (Aloe, *J Neuroimmunol* 18:1–12, 1988). In addition, mast cells express the trk receptor and respond to NGF such that NGF is a mast cell secretogogue and survival promoting factor (Horigome et al., *J Biol Chem* 269:2695–2707, 1994). Moreover, members of the TGF-β superfamily act on many cell types of different function and embryologic origin.

Thus, it is likely that artemin will have trophic activity on a variety of different neuronal cells, both peripheral and central, as well as on non-neuronal cells. With respect to neuronal cells, artemin supports the survival of neurons from all peripheral ganglia examined thus far, including sympathetic neurons and neural crest and placodally-derived sensory neurons, and also supports the survival of at least one population of CNS neurons, i.e., dopaminergic midbrain neurons. In addition, the inventors herein have detected artemin expression in a number of adult and fetal tissues, including heart, kidney, lung, peripheral leukocytes and bone marrow, which further supports the conclusion that artemin can provide trophic support to a variety of neuronal and non-neuronal cells. This suggests a role for artemin in hematopoiesis, inflammation, allergy, and cardiomyopathy. Artemin's trophic activity on any particular target cell type can be determined by routine experimentation using standard reference models.

The invention also contemplates synthetic, pan-growth factors comprising at least one active domain of artemin combined with at least one active domain of one or more other non-artemin growth factors. (For example, see Ilag et al., Proc Nat'l Acad Sci 92:607–611, 1995). These pan-growth factors would be expected to have the combined activities or other advantageous properties of artemin and the one or more other growth factors. As such, these pan-growth factors are believed to be potent and multispecific growth factors that are useful in the treatment of a wide spectrum of degenerative diseases and conditions including conditions that can be treated by any or all of the parent factors from which the active domains were obtained. Such pan-growth factors might also provide synergistic effects beyond the activities of the parent factors (Barres et al., supra).

Pan-growth factors within the scope of the present invention can include chimeric or hybrid polypeptides that are constructed from portions of fragments of at least two growth factors. Growth factors of the TGF-β superfamily are structurally related having highly conserved sequence landmarks whereby family members are identified. In particular, seven canonical framework cysteine residues are nearly invariant in members of the superfamily (Kingsley, Genes & Dev 8:133–146, 1994 which is incorporated by reference). Chimeric polypeptide molecules can, therefore, be constructed from a sequence that is substantially identical to a portion of the artemin molecule, up to one or more crossover points, and one or more sequences each of which is substantially identical with a portion of another TGF-β superfamily member extending on the other side of the corresponding one or more crossover points. For example, a portion of the amino terminal end of the artemin polypeptide can be combined with a portion of the carboxy terminal end of a neurturin polypeptide or alternatively a portion of the amino terminal end of a neurturin polypeptide can be combined with a portion of the carboxy terminal end of an artemin polypeptide. Such portions of artemin or neurturin polypeptides are preferably from about 5 to about 95, more preferably from about 10 to about 90, still more preferably from about 20 to about 80 and most preferably from about 30 to about 70 contiguous amino acids and such portions of another, non-artemin or, as the case may be, non-neurturin TGF-β superfamily member are preferably from about 5 to about 95, more preferably from about 10 to about 90, still more preferably from about 20 to about 80 and most preferably from about 30 to about 70 contiguous amino acids. For example, a particular crossover point might be between the third and fourth canonical framework cysteine residues. The particular non-artemin TGF-β family member could be selected from family members including but not limited to transforming growth factor-β1 (TGFβ1), transforming growth factor-β (TGFβ2), transforming growth factor-β3 (TGFβ3), inhibin β A (INHβA), inhibin β B (INHβB), the nodal gene (NODAL), bone morphogenetic proteins 2 and 4 (BMP2 and BMP4), the Drosophila decapentaplegic gene (dpp), bone morphogenetic proteins 5–8 (BMP5, BMP6, BMP7 and BMP8), the Drosophila 60A gene family (60A), bone morphogenetic protein 3 (BMP3), the Vg1 gene, growth differentiation factors 1 and 3 (GDF1 and GDF3), dorsalin (drsln), inhibin α (INHα), the MIS gene (MIS), growth factor 9 (GDF-9), glial-derived neurotrophic growth factor (GDNF), neurturin (NTN) and persephin. Furthermore, additional crossover points can be used to incorporate any desired number of artemin portions or fragments with portions or fragments of any one or more other family members.

In constructing a particular chimeric molecule, the portions of artemin and portions of the other, non-artemin growth factor are amplified using PCR, mixed and used as template for a PCR reaction using the forward primer from one and the reverse primer from the other of the two component portions of the chimeric molecule. Thus, for example a forward and reverse primers are selected to amplify the portion of artemin from the beginning to the selected crossover point between the third and fourth canonical cysteine residues using a artemin-encoding plasmid as template. A forward primer with a 5' portion overlapping with the artemin sequence and a reverse primer are then used to amplify the portion of the other, non-artemin growth factor member of the TGF-β superfamily from the corresponding crossover point through the 3' end using a plasmid template containing the coding sequence for the non-artemin TGF-β family member. The products of the two PCR reactions are gel purified and mixed together and a PCR reaction performed. Using an aliquot of this reaction as template a PCR reaction is performed using the artemin forward primer and the reverse primer for the non-artemin growth factor. The product is then cloned into an expression vector for production of the chimeric molecule.

Chimeric growth factors would be expected to be effective in promoting the growth and development of cells and for use in preventing the atrophy, degeneration or death of cells, particular in neurons. The chimeric polypeptides may also act as receptor antagonists of one or both of the full length growth factors from which the chimeric polypeptide was constructed or as an antagonist of any other growth factor that acts at the same receptor or receptors.

The present invention also includes therapeutic or pharmaceutical compositions comprising an artemin polypeptide in an effective amount for providing trophic support to cells in patients with cellular degeneration or dysfunction and a method comprising administering a therapeutically effective amount of the artemin polypeptide to a cell ex vivo or in vivo. The term "trophic support" is used herein to mean that a growth factor such as artemin provides sufficient nourishment to a cell such that the cell maintains or recovers at least one or more of its normal functions.

The compositions and methods of the present invention are useful for treating a number of degenerative diseases and anaplastic diseases. Where the cellular degeneration, dysfunction or anaplasia involves neurons, the diseases include, but are not limited to peripheral neuropathy, amyotrophic lateral sclerosis, Alzheimer's disease, Parkinson's disease, Huntington's disease, ischemic stroke, acute brain injury, acute spinal chord injury, nervous system tumors such as neuroblastomas, multiple sclerosis, peripheral nerve trauma or injury, exposure to neurotoxins, metabolic diseases such as diabetes or renal dysfunctions and damage caused by infectious agents. In addition, artemin compositions can be used to treat enteric diseases such as idiopathic constipation or constipation associated with Parkinson's disease, spinal cord injury or use of opiate pain-killers. If the cellular degeneration or dysfunction involves nonneuronal cells such as bone marrow cells, artemin may be useful in treating diseases including, but not limited to disorders of insufficient blood cells such as, for example, leukopenias including eosinopenia and/or basopenia, lymphopenia, monocytopenia, neutropenia, anemias, thrombocytopenia as well as an insufficiency of stem cells for any of the above. The cellular degeneration or dysfumction can also involve myocardial muscle cells in diseases such as cardiomyopathy and congestive heart failure. In addition small cell lung carcinoma can be treated with artemin polypeptide or polynucleotide compositions.

Treatment of enteric diseases with artemin includes the treatment of enteric neuropathies. The enteric nervous system is a complex collection of nerves that control the function of the gastrointestinal system, including gastrointestinal motility. Initial clinical studies with the NT-3, have shown that this neurotrophic factor increases gastrointestinal motility in normal volunteers and in patients suffering from peripheral neuropathies. Similarly, it is believed that artemin as well as the other members of the GDNF/neurturin/persephin family of growth factors will also show activity on enteric neurons. As a result, it is believed that artemin will be useful in treating enteric neuropathies such as in patients suffering from severe idiopathic constipation as well as patients suffering from constipation associated with Parkinson's disease, spinal cord injury, use of opiate pain-killers, and the like.

Whether artemin would be effective in the treatment of a particular cell type or tissues can be readily determined by one skilled in the art using any of a variety of assays known in the art. For example, with respect to providing trophic support for cells, trophic factors can produce beneficial biochemical and morphological effects and, under some circumstances, can promote cell survival. With respect to neurons, it is known in the art that depriving a neuron of trophic support results in a decrease in metabolic activity, i.e., glucose uptake, RNA synthesis and protein synthesis, required for normal function and growth. Deckwerth and Johnson, *J. Cell Biol.* 123:1207–1222, 1993. Removal of trophic support also results in a reduction in size of the cell body of the neuron. Presumably as a consequence of the loss of the metabolic effects of trophic factors, trophic factor deprivation results in a decrease or cessation of process outgrowth and may result in retraction of neuronal processes. In addition to the requirement of trophic factor for these aspects of neuronal biology, the neuron may require the neurotrophic factor to maintain survival; thus, survival assays are a frequently used means to detect or quantitate the actions of a neurotrophic factor. However, trophic support can also be manifest as morphological, biochemical, and functional changes; independent of neuronal number or any effect on survival.

As discussed above, growth factors can produce a cell differentiation in addition to providing trophic support for cells. Thus, it is believed that artemin polypeptides and polynucleotides can be beneficially used to produce a differentiation of anaplastic cells such as cancer cells. In particular, artemin can be used to treat nervous system tumors such as neuroblastomas. In addition, small cell lung carcinomas are known to express RET. Hence, it is believed that artemin can also be used to treat small cell lung carcinomas.

It is also contemplated that the eliciting of trophic support and/or differentiation can be achieved by administering an artemin polypeptide along with a GFRα3 polypeptide or by administering an artemin polynucleotide and a GFRα3 polynucleotide using the methods described herein for administration of artemin polypeptides or artemin polynucleotides. As noted above, Mouse GFRα3 was first identified as an expressed sequence tag (EST) that is homologous to GFRα1 and GFRα2 (Baloh et al., 1998, supra; Jing et al., 1997, supra; Naveilhan et al., *Proc Natl Acad Sci USA* 95, 1295–300, 1998; Widenfalk et al., *Eur. J. Neurosci.* 10, 1508–1517, 1998; Worby et al., *J Biol Chem* 273, 3502–3508, 1998). Human GFRα3 was identified by using the human GFRα2 amino acid sequence as a query to search a database of Expressed Sequence Tags (dbEST database) with the BLAST search algorithm (Altschul et al. *J.Mol.Biol.* 215:403–410, 1990; see copending application entitled "GFRα3, A Novel Member of the GDNF Coreceptor Family" which is file concurrently with the present application on Dec. 22, 1998 and which is incorporated in its entirety herein by reference). Of the EST sequences identified, several (AA049894, AA050083, AA041935, AA238748) did not correspond identically to either GFRα1 or GFRα2 but had significant homologies to both sequences. The clones corresponding to these EST's were acquired from the Washington University EST project and sequenced. One of these corresponded to a fuill-length mouse cDNA which the inventors herein named GFRα3. Sequence information from the mouse cDNA was used to identify human genomic and cDNA clones, and the corresponding human and mouse predicted protein sequences are shown in FIG. 12. The predicted amino acid sequences for human and mouse GFRα3 indicate a ~38.8 kDa protein with a putative N-terrninal signal sequence (amino acids 1–31 in hGFRα3 and 1–28 in mGFRα3 of FIG. 12) (Nielsen et al., *Protein Eng.* 10:106, 1997), a mature GFRα3 polypeptide (amino acids 32–372 in hGFRα3 and 29–369 in mGFRα3 of FIG. 12), three putative N-linked glycosylation sites, and a hydrophobic stretch of residues at the C-terminus consistent with a GPI signal peptide (amino acids 373–400 of hGFRα3 and 370–397 of mGFRα3 of FIG. 12) (Undenfriend et al., *Annu. Rev. Biochem.* 64:563–591, 1995) like those present in the related proteins GFRα1 and GFRα2 (Klein et al., *Nature* 387: 717–721, 1997; Jing et al., *Cell* 85:1113–1124, 1996; Treanor et al., *Nature* 382:80–83, 1996; Baloh et al., *Neuron* 18:793–802, 1997.). The human nucleotide sequence encoding GFRα3 precursor (SEQ ID NO:65) is shown in FIG. 13. This precursor sequence includes the encoding sequence for the N-terminal signal sequence (nucleotides 1–93 of FIG. 13), the encoding sequence for mature GFRα3 (nucleotides 94–1116 of FIG. 13) and the encoding sequence for the C-terminal hydrophobic stretch of residues consistent with a GPI signal peptide (nucleotides 1117–1203 of FIG. 13).

As described below, artemin binds to GFRα3 in the absence of RET and it is believed that the resulting ligand/coreceptor complex is capable of binding to and activating RET receptors expressed by a target cell. Thus, treatment with artemin and GFRα3 would be expected to increase the sensitivity of cells normally responsive to artemin and would also be expected to provide trophic support to cells that express RET but that are not normally responsive to artemin. Preferably, the artemin and GFRα3 polypeptides are from the same species, i.e., human. It is also preferred that the GFRα3 polypeptide be in soluble form, i.e., that it lack the GPI linkage to avoid potential undesirable interactions with cell membranes. As used herein a GFRα3 polypeptide is intended to include the mature protein with or without the GPI anchor, as well as GFRα3 fragments, particularly soluble fragments lacking a GPI anchor, that are capable of binding to both artemin and RET with such binding leading to the activation of RET.

In certain circumstances, it may be desirable to modulate or decrease the amount of artemin expressed. Thus, in another aspect of the present invention, artemin anti-sense oligonucleotides can be made and a method utilized for diminishing the level of expression of artemin, respectively, by a cell comprising administering one or more artemin anti-sense oligonucleotides. By artemin anti-sense oligonucleotides reference is made to oligonucleotides that have a nucleotide sequence that interacts through base pairing with a specific complementary nucleic acid sequence involved in the expression of artemin such that the expression of artemin is reduced. Preferably, the specific nucleic acid sequence involved in the expression of artemin is a genomic DNA molecule or mRNA molecule that contains sequences of the artemin gene. Thus, the invention contemplates artemin anti-sense oligonucleotides that can base pair to flanking regions of the artemin gene, untranslated regions of artemin mRNA, the pre- or pro-portions of the artemin gene or the coding sequence for mature artemin protein. The term complementary to a nucleotide sequence in the context of artemin antisense oligonucleotides and methods therefor means sufficiently complementary to such a sequence as to allow hybridization to that sequence in a cell, i.e., under physiological conditions. The artemin antisense-oligonucleotides preferably comprise a sequence containing from about 8 to about 100 nucleotides and more preferably the artemin antisense oligonucleotides comprise from about 15 to about 30 nucleotides. The artemin antisense oligonucleotides can also contain a variety of modifications that confer resistance to nucleolytic degradation such as, for example, modified internucleoside linkages (Uhlmann and Peyman, *Chemical Reviews* 90:543–548, 1990; Schneider and Banner, *Tetrahedron Lett* 31:335, 1990), modified nucleic acid bases and/or sugars and the like.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation. For treating tissues in the central nervous system, administration can be by injection or infusion into the cerebrospinal fluid (CSF). When it is intended that artemin be administered to cells in the central nervous system, administration can be with one or more agents capable of promoting penetration of artemin across the blood-brain barrier.

Artemin can also be linked or conjugated with agents that provide desirable pharmaceutical or pharmacodynamic properties. For example, artemin can be coupled to any substance known in the art to promote penetration or transport across the blood-brain barrier such as an antibody to the transferrin receptor, and administered by intravenous injection. (See for example, Friden et al., *Science* 259:373–377, 1993). Furthermore, artemin can be stably linked to a polymer such as polyethylene glycol to obtain desirable properties of solubility, stability, half-life and other pharmaceutically advantageous properties. (See for example Davis et al. *Enzyme Eng* 4:169–73, 1978; Burnham, *Am J Hosp Pharm* 51:210–218, 1994). Preferably, artemin is administered with a carrier such as liposomes or polymers containing a targeting moiety to limit delivery of artemin to targeted cells. Examples of targeting moieties include but are not limited to antibodies, ligands or receptors to specific cell surface molecules.

For nonparenteral administration, the compositions can also include absorption enhancers which increase the pore size of the mucosal membrane. Such absorption enhancers include sodium deoxycholate, sodium glycocholate, dimethyl-β-cyclodextrin, lauroyl-1-lysophosphatidylcholine and other substances having structural similarities to the phospholipid domains of the mucosal membrane.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. Artemin can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing artemin are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art based on the activity of artemin for a particular cell type in vitro. The activity of artemin on various peripheral and central neurons in culture is described below and artemin activity on a particular target cell type can be determined by routine experimentation. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, artemin may be therapeutically administered by implanting into patients vectors or cells capable of producing a biologically-active form of artemin or a precursor of artemin, i.e. a molecule that can be readily converted to a biological-active form of artemin by the body. In one approach cells that secrete artemin may be encapsulated into semipermeable membranes for implantation into a patient. The cells can be cells that normally express artemin or a precursor of artemin or the cells can be transformed to express artemin or a precursor thereof. In some embodiments, the cells are transformed to express and secrete both artemin and GFRα3, preferably in a soluble form. It is preferred that the cell be of human origin and that the artemin be human artemin when the patient is human. However, the formulations and methods herein can be used for veterinary as well as human applications and the term "patient" as used herein is intended to include human and veterinary patients.

Cells can be grown ex vivo for use in transplantation or engraftment into patients (Muench et al., *Leuk & Lymph* 16:1–11, 1994). In another embodiment of the present invention, artemin can be used to promote the ex vivo expansion of a cells for transplantation or engraftment. Current methods have used bioreactor culture systems containing factors such as erythropoietin, colony stimulating factors, stem cell factor, and interleukins to expand hematopoietic progenitor cells for erythrocytes, monocytes, neutrophils, and lymphocytes (Verfaillie, *Stem Cells* 12:466–476, 1994). These stem cells can be isolated from the marrow of human donors, from human peripheral blood, or from umbilical cord blood cells. The expanded blood cells are used to treat patients who lack these cells as a result of specific disease conditions or as a result of high dose chemotherapy for treatment of malignancy (George, *Stem Cells* 12(Suppl 1):249–255, 1994). In the case of cell transplant after chemotherapy, autologous transplants can be performed by removing bone marrow cells before chemotherapy, expanding the cells ex vivo using methods that also function to purge malignant cells, and transplanting the expanded cells back into the patient following chemotherapy (for review see Rummel and Van Zant, *J Hematotherapy* 3:213–218, 1994).

It is also believed that artemin with or without GFRα3 can be used for the ex vivo expansion of precursor cells in the nervous system. Transplant or engraftment of cells is currently being explored as a therapy for diseases in which certain populations of neurons are lost due to degeneration such as, for example, in Parkinson's disease (Bjorklund, *Curr Opin Neurobiol* 2:683–689, 1992). Neuronal precursor cells can be obtained from animal or human donors or from human fetal tissue and then expanded in culture using artemin. These cells can then be engrafted into patients where they would function to replace some of the cells lost due to degeneration. Because neurotrophins have been shown to be capable of stimulating the survival and proliferation of neuronal precursor cells such as, for example, NT-3 stimulation of sympathetic neuroblast cells (Birren et al., *Develop* 119:597–610, 1993), artemin could also function in similar ways during the development of the nervous system and could be useful in the ex vivo expansion of neuronal cells.

In a number of circumstances it would be desirable to determine the levels of artemin or soluble GFRα3 in a patient. A change in the amount of endogenously produced artemin or GFRα3 may play a role in certain disease conditions, particularly where there is cellular degeneration such as in neurodegenerative conditions or diseases. Other neurotrophic factors are known to change during disease conditions. For example, in multiple sclerosis, levels of NGF protein in the cerebrospinal fluid are increased during acute phases of the disease (Bracci-Laudiero et al., *Neuroscience Lett* 147:9–12, 1992) and in systemic lupus erythematosus there is a correlation between inflammatory episodes and NGF levels in sera (Bracci-Laudiero et al. *NeuroReport* 4:563–565, 1993).

Thus, quantification of artemin levels may provide clinically useful information. Furthermore, in the treatment of degenerative conditions, compositions containing artemin can be administered and it would likely be desirable to achieve certain target levels of artemin in sera, in cerebrospinal fluid or in any desired tissue compartment. It would, therefore, be advantageous to be able to monitor the levels of artemin in a patient. Accordingly, the present invention also provides methods for detecting the presence of artemin in a sample from a patient.

The term "detection" as used herein in the context of detecting the presence of artemin in a patient is intended to include the determining of the amount of artemin or the ability to express an amount of artemin in a patient, the distinguishing of artemin from other growth factors, the estimation of prognosis in terms of probable outcome of a degenerative disease and prospect for recovery, the monitoring of the artemin levels over a period of time as a measure of status of the condition, and the monitoring of artemin levels for determining a preferred therapeutic regimen for the patient.

To detect the presence of artemin in a patient, a sample is obtained from the patient. The sample can be a tissue biopsy sample or a sample of blood, plasma, serum, CSF or the like. Samples for detecting artemin can be taken from any tissue known to express artemin. When assessing peripheral levels of artemin, it is preferred that the sample be a sample of blood, plasma or serum or alternatively from a tissue biopsy sample. When assessing the levels of artemin in the central nervous system a preferred sample is a sample obtained from cerebrospinal fluid.

In some instances it is desirable to determine whether the artemin gene is intact in the patient or in a tissue or cell line within the patient. By an intact artemin gene it is meant that there are no alterations in the gene such as point mutations, deletions, insertions, chromosomal breakage, chromosomal rearrangements and the like wherein such alteration might alter production of artemin or alter its biological activity, stability or the like to lead to disease processes or susceptibility to cellular degenerative conditions. Conversely, by a non-intact artemin gene it is meant that such alterations are present. Thus, in one embodiment of the present invention a method is provided for detecting and characterizing any alterations in the artemin gene. The method comprises providing a polynucleotide that specifically hybridizes to an artemin cDNA, genomic DNA or a fragment thereof.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact artemin gene or an abnormality in the artemin gene. Hybridization to the artemin gene would involve denaturing the chromosomal DNA to obtain a single-stranded DNA; contacting the single-stranded DNA with a gene probe associated with the artemin gene sequence; and identifying the hybridized DNA-probe to detect chromosomal DNA containing at least a portion of the human artemin gene.

The term "probe" as used herein refers to a structure comprised of a polynucleotide which forms a hybrid structure with a target sequence, due to complementarity of probe sequence with a sequence in the target region. The probes need not contain the exact complement of the target sequence, but must be sufficiently complementary to selectively hybridize with the strand being detected. By selective hybridization or specific hybridization it is meant that a polynucleotide preferentially hybridizes to a target polynucleotide. Oligomers suitable for use as probes may contain a minimum of about 8–12 contiguous nucleotides which are complementary to the targeted sequence and preferably a minimum of about 15 or 17 nucleotides although polynucleotide probes of about 20 to 25 nucleotides and up to about 100 nucleotides or even greater are within the scope of this invention.

The artemin gene probes of the present invention can be DNA or RNA oligonucleotides and can be made by any method known in the art such as, for example, excision, transcription or chemical synthesis. Probes may be labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25–45° C., more preferably at 32–40° C. and more preferably at 37–38° C. The time required for hybridization is from about 0.25 to about 96 hours, more preferably from about one to about 72 hours, and most preferably from about 4 to about 24 hours.

Artemin gene abnormalities can also be detected by using the PCR method or any other known DNA amplification method, which uses oligonucleotides to identify a target sequence within a longer sequence and primers that flank or lie within the artemin gene. The PCR method is well known in the art. Briefly, this method is performed using two oligonucleotide primers which are capable of hybridizing to the nucleic acid sequences flanking a target sequence that lies within an artemin gene and amplifying the target sequence. The terms "oligonucleotide primer" as used herein refers to a short strand of DNA or RNA typically ranging in length from about 8 to about 30 bases. The upstream and downstream primers are preferably a minimum of from about 15 nucleotides to about 20 nucleotides and up to about 30 nucleotides or even greater in length. The primers can hybridize to the flanking regions for replication of the target nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, the method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize or specifically hybridize with the strand being amplified. By selective hybridization or specific hybridization it is meant that a polynucleotide preferentially hybridizes to a target polynucleotide.

After PCR amplification, the DNA sequence comprising an artemin-encoding nucleotide sequence or a fragment thereof is then directly sequenced and analyzed by comparison of the sequence with the sequences disclosed herein to identify alterations which might change activity or expression levels or the like.

In another embodiment a method for detecting artemin is provided based upon an analysis of tissue expressing the artemin gene. The method comprises hybridizing a polynucleotide probe to mRNA from a sample of tissues that normally express the artemin gene or from a cDNA produced from the mRNA of the sample. The sample is obtained from a patient suspected of having an abnormality in the artemin gene or from a particular patient tissue or cell type suspected of having an abnormality in the artemin gene.

To detect the presence of mRNA encoding artemin protein, a sample is obtained from a patient. The sample can be from blood or from a tissue biopsy sample. The sample may be treated to extract the mRNA contained therein. The resulting mRNA from the sample is subjected to gel electrophoresis or other size separation techniques.

The mRNA of the sample is contacted with a nucleic acid serving as a probe to form hybrid duplexes. The use of a labeled probes as discussed above allows detection of the resulting duplex.

High stringency conditions can be used in order to prevent false positives, that is hybridization to non-artemin nucleotide sequences. When using sequences that are not perfectly complementary to an artemin-encoding polynucleotide or a fragment thereof, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook, et al., 1989, supra).

In order to increase the sensitivity of the detection in a sample of mRNA encoding the artemin protein, the technique of reverse transcription/polymerization chain reaction (RT/PCR) can be used to amplify cDNA transcribed from mRNA encoding the artemin protein. The method of RT/PCR is well known in the art.

Alternatively, an artemin target sequence in the reverse transcribed cDNA can be amplified and detected using any other known methodology such as ligase chain reaction methods, including gap LCR (G-LCR) and other variations, or self-sustained sequence replication (3SR) and its various modifications. In addition, the artemin mRNA can be detected directly by asymmetric gap LCR (AG-LCR). See, e.g., Leckie et al., "Infectious Disease Testing by Ligase Chain Reaction" in *Molecular Biology and Biotechnology*, R. A. Myers, ed., pp. 463–466, VCH Publishers, 1995.

The present invention further provides for methods to detect the presence of the artemin protein in a sample obtained from a patient. Any method known in the art for detecting proteins can be used. Such methods include, but are not limited to immunodiffiision, immunoelectrophoresis, immunochemical methods, binder-ligand assays, immunohistochemical techniques, agglutination and complement assays. (for example see *Basic and Clinical Immunology*, Sites and Terr, eds., Appleton & Lange, Norwalk, Conn. pp 217–262, 1991). Preferred are binder-ligand immunoassay methods including reacting antibodies with an epitope or epitopes of the artemin protein and competitively displacing the artemin protein.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to the artemin protein or to an epitope thereof can be made for use in immunoassays by any of a number of methods known in the art. By epitope reference is made to an antigenic determinant of a polypeptide. The term epitope can also include artemin-specific B cell epitopes or T helper cell epitopes. An epitope could comprise 3 amino acids in a spatial conformation which is unique to the epitope. Generally an epitope consists of at least 6 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse (See Example 10).

Oligopeptides can be selected as candidates for the production of an antibody to the artemin protein based upon the oligopeptides lying in hydrophilic regions, which are thus likely to be exposed in the mature protein.

Antibodies to artemin can also be raised against oligopeptides that include one or more of the conserved regions identified herein such that the antibody can cross-react with other family members. Such antibodies can be used to identify and isolate the other family members.

Methods for preparation of the artemin protein or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J Am Chem Soc* 85:2149, 1963) or the FMOC strategy on a Rapid Automated Multiple Peptide Synthesis system (DuPont Company, Wilmington, Del.) (Caprino and Han, *J Org Chem* 37:3404, 1972).

Polyclonal antibodies can be prepared by immunizing rabbits or other animals by injecting antigen followed by subsequent boosts at appropriate intervals. The animals are bled and sera assayed against purified artemin protein usually by ELISA or by bioassay based upon the ability to block the action of artemin. When using avian species, e.g. chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler *Nature* 256:495–497, 1975; Gulfre and Milstein, *Methods in Enzymology: Immunochemical Techniques* 73:1–46, Langone and Banatis eds., Academic Press, 1981). The hybridoma cells so formed are then cloned by limiting dilution methods and supernates assayed for antibody production by ELISA, RIA or bioassay.

The unique ability of antibodies to recognize and specifically bind to target proteins provides an approach for treating an over expression of the protein. Thus, another aspect of the present invention provides for a method for preventing or treating diseases involving over expression of the artemin protein by treatment of a patient with specific antibodies to the artemin protein.

Specific antibodies, either polyclonal or monoclonal, to the artemin protein can be produced by any suitable method known in the art as discussed above. For example, murine or human monoclonal antibodies can be produced by hybridoma technology or, alternatively, the artemin protein, or an immunologically active fragment thereof, or an anti-idiotypic antibody, or fragment thereof can be administered to an animal to elicit the production of antibodies capable of recognizing and binding to the artemin protein. Such antibodies can be from any class of antibodies including, but not limited to IgG, IgA, IgM, IgD, and IgE or in the case of avian species, IgY and from any subclass of antibodies.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the identification and cloning of polynucleotides encoding human and mouse artemin.

Artemin was discovered by using the full length murine pre-pro neurturin amino acid sequence (195 amino acids) to scan the High Throughout Genome Sequences (htgs) database. The database was searched using the tblastn feature of the BLAST 2.0.5 program using the default parameters (Altschul, et al., Nucleic Acids Res. 25:3389–3402, 1997). This search identified two human bacterial artificial chromosome (BAC) clones, AC005038 (NH0486122) and AC005051 (RG037F03), with significant homology scores when aligned with murine pre-pro neurturin. When the BLAST search was repeated using the mature human neurturin sequence as a query, the same two BAC clones were identified. Using the sequences of these two BAC clones, two EST's (Expressed Sequence Tags) were also identified in the EST database using the blastn feature of BLAST 2.0.5 program using the default parameters. These ESTs were: AA931637 (oo35c12) from a lung carcinoma and AA533512 (nj96b11) from a prostate carcinoma. Analysis of these alignments indicated that portions of the anonymous htgs sequences possibly represented a new member of the GDNF-neurturin-persephin family. Indeed, although, the hgts sequences were later discovered to have numerous sequence errors, i.e. omissions, additions and incorrect bases, one of the BAC clones, AC005038, had a stretch of 197 nucleotides (nucleotides 67,464 to 67,660) which ultimately turned out to be identical to nucleotides 663–467 of the complementary strand of the artemin nucleic acid (FIG.

1B) and the other, AC005051, had a stretch of 183 nucleotides (nucleotides 113,379 to 113,561) identical to nucleotides 648–468 of the complementary strand of the artemin nucleic acid (FIG. 1B).

Because sequences in the hgts database were generally known to contain many sequence errors, oligonucleotide primers were designed from the sequences of the two htgs entries to obtain fragments of the gene for this new growth factor from human genomic DNA. The primers were designed to amplify an approximate 708 nt fragment encoding a portion of the predicted new growth factor, which would extend from within the pro-domain, through the mature region of the protein, and end within the 3' untranslated region. Human genomic DNA was used as a template in a PCR reaction which utilized a forward primer M4206 [5'-TGGCCGCTCTGGCTCTGCTGAGCA-3'] (SEQ ID NO:20) and reverse primer M4205 [5'-CGATCATCTAGACCACCGGTAAGGGTCCAGTCTG-CAA-3'] (SEQ ID NO:21). The PCR reaction was carried out using Klentaq in Klentaq buffer with additives (1.5 M betaine/1.5% DMSO; final concentration) and the following parameters: initial denaturation at 95° C. for 5 min, then 950C for15 sec, 60 C for 30 sec, 68 C for 80 sec x 30 cycles. The amplified products were kinased with T4 polynucleotide kinase, the ends were blunted with *E. coli* DNA polymerase I (Klenow fragment), and cloned into EcoRV digested BSKS plasmid. The nucleotide sequences of the resulting clones were obtained.

An additional, overlapping fragment was also amplified from human genomic DNA, which extends from the beginning of the mature region to the stop codon. This was amplified by PCR using the forward primer M4207 (5'-TACAAGGACGATGAC-GATAAGGGGGCGCGGGGCTGCGGCCTGCGCTCGC AGCTG-3') (SEQ ID NO:22) and reverse primer M4205 (5'-CGATCATCTAGACCACCGGTAAGGGTCCAGT-CTGCAA-3') (SEQ ID NO:23). The PCR reaction was carried out using Klentaq in Klentaq buffer with additives (5% DMSO; final concentration) and the following parameters: initial denaturation at 95° C. for 5 min, then 95° C. for 15 sec, 60° C. for 30 sec, 68° C. for 80 sec×30 cycles. The amplified products were kinased with T4 polynucleotide kinase, the ends were blunted with *E. coli* DNA polymerase I (Klenow fragment), and cloned into EcoRV digested BSKS plasmid. The nucleotide sequences of the resulting clones were obtained.

The sequences from these fragments and the sequences of the entries in the htgs database were assembled using Seqman program (DNASTAR). The assembled nucleotide sequence, which is shown in FIG. 1A, encodes a partial pro-artemin amino acid sequence which extends from within the pro-domain, includes 3 potential RXXR cleavage sites and then includes a region corresponding to the mature artemin polypeptide, which is homologous to mature GDNF, neurturin and persephin as shown in FIG. 2A.

Primers designed from this sequence were also used to PCR amplify a fragment of mouse genomic DNA which corresponded to the mouse artemin gene. This mouse DNA fragment was than used to screen mouse BAC genomic libraries and a BAC clone containing the mouse artemin gene was identified (data not shown).

Primers were made from the human and mouse artemin genomic sequences to perform rapid amplification of cDNA ends (RACE) PCR to obtain the 5' end of the artemin cDNA from several tissue libraries. PCR fragments were blunt-cloned into EcoRV digested BSKS as above, and sequenced entirely. Human RACE products were obtained from MARATHON RACE cDNA libraries (CLONTECH) prepared from pituitary, placenta, and kidney. Mouse RACE products were obtained from an embryonic day 18 (E18) mouse MARATHON RACE library. Complete double-stranded sequence analysis of cloned PCR fragments from genomic DNA and cDNA was performed to generate contigs of the human and mouse cDNAs. At least two independent clones of each PCR fragment were sequenced. Genomic sequence of mouse BAC clone restriction fragments (subdloned into pBluescript), and sequences derived from portions of the human BAC clone, were used to confirm the cDNA sequences, which are shown in FIG. 1B (human) and FIG. 1C (mouse).

Figure 2C:
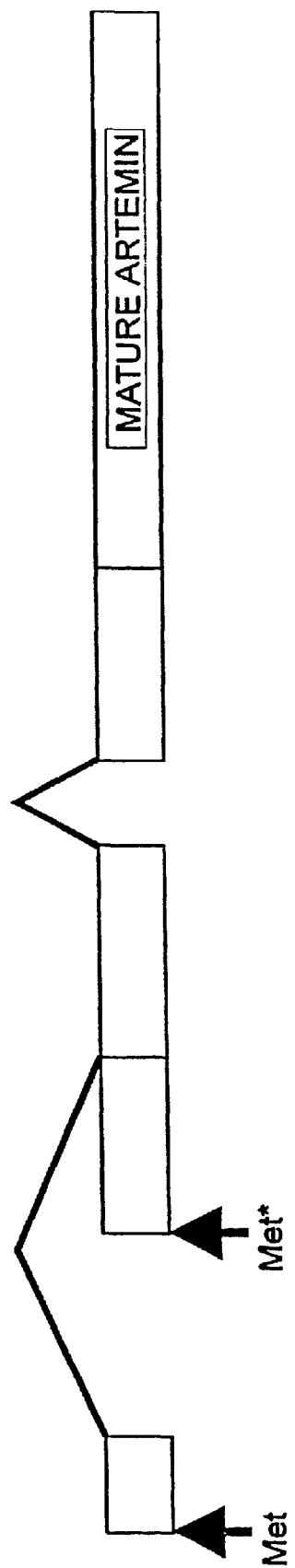
FIG. 2C is a schematic diagram of the location of the two introns in the artemin gene, and their splicing to produce artemin mRNA, with the location of a second starting methionine identified by RACE PCR in cDNA's isolated from some human cDNA libraries indicated by Met*.

Intron locations in the cDNA and splicing were confirmed by sequencing PCR amplified fragments from human and mouse cDNA libraries that cross both introns. As illustrated in FIG. 2C, the artemin gene has two introns. cDNAs containing a second starting methionine (Met*) produced by alternative splicing of the first intron were also identified by RACE PCR from some human cDNA libraries; however, a similar message was not identified in mouse, and the mouse genomic sequence does not contain a methionine in this position. Mature artemin protein generated from either of the human messages would be identical.

Analysis of markers present on the artemin-encoding BAC clones indicated that the human artemin gene is located on chromosome 1p32–33, flanked by markers D1S190-artemin-D1S211 (telomeric to centromeric).

The human DNA sequence as shown in FIG. 14, which includes the Artemin gene, was compiled from sequences from multiple independently cloned PCT products using human genomic DNA as template and from the human BAC clone sequences. The beginning of the sequence corresponds to nt 11472 of BAC clone AC00505 1, and nt 68862 of BAC clone AC005038 from the htgs database as described above.

Figure 15:
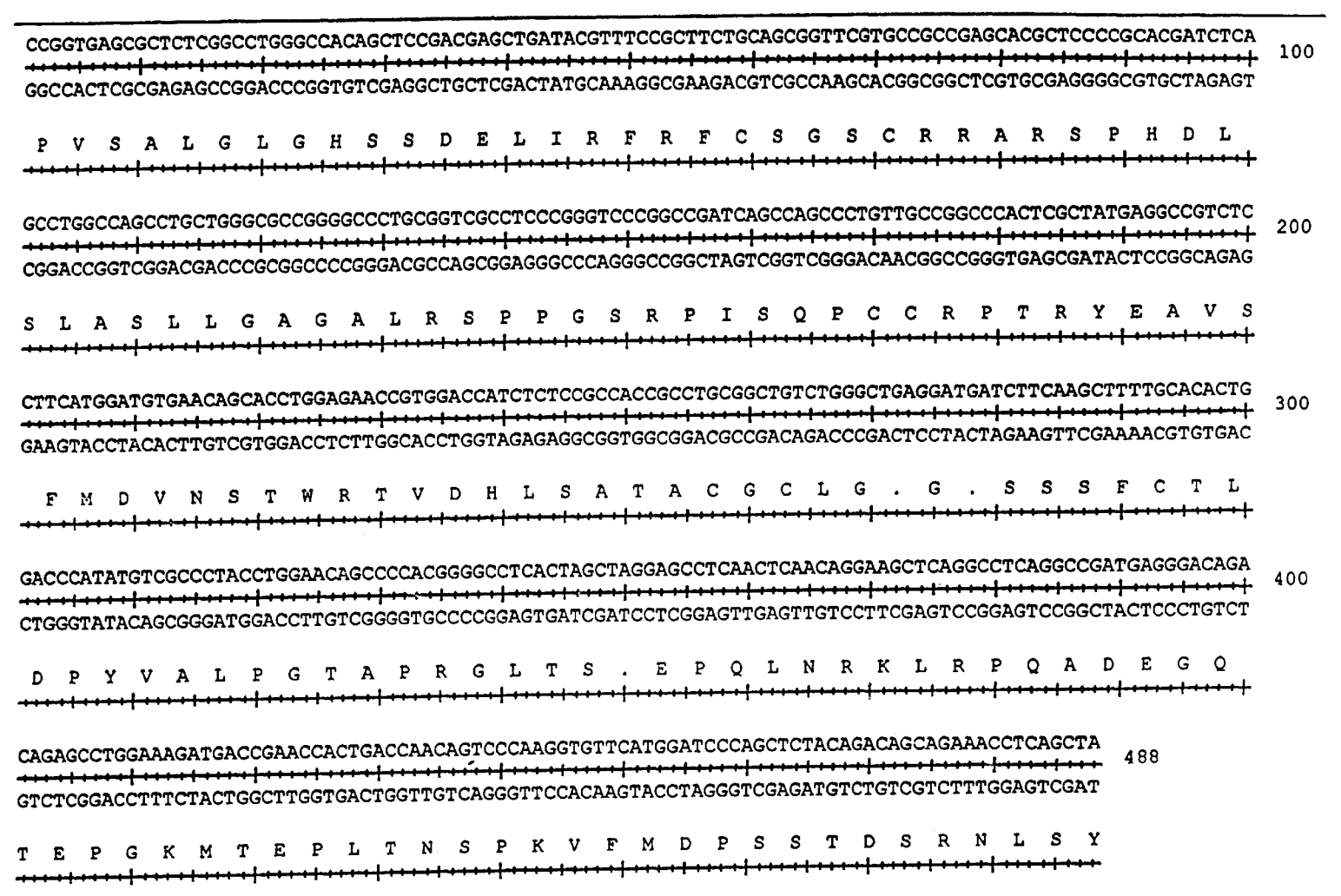

A rat artemin cDNA fragment as shown in FIG. 15 was generated using PCT from a rat Schwann cell cDNA library as template with the following primers: forward 5'-CCGGTGAGCGCTCTCGGCCT-3' (SEQ ID NO:76) and reverse primer 5'-TTCTGGATTCTCCCAGAGGAGTTC-3' (SEQ ID NO:77). PCT conditions were as follows: 95° C. for 2 min; then 30 cycles of 95° C. for 10 sec, 60° C. for 30 sec; 72° C. for 30 sec, then 72° C. for 5 min.

EXAMPLE 2

This example illustrates the expression of artemin in various human tissues.

Figure 5A:
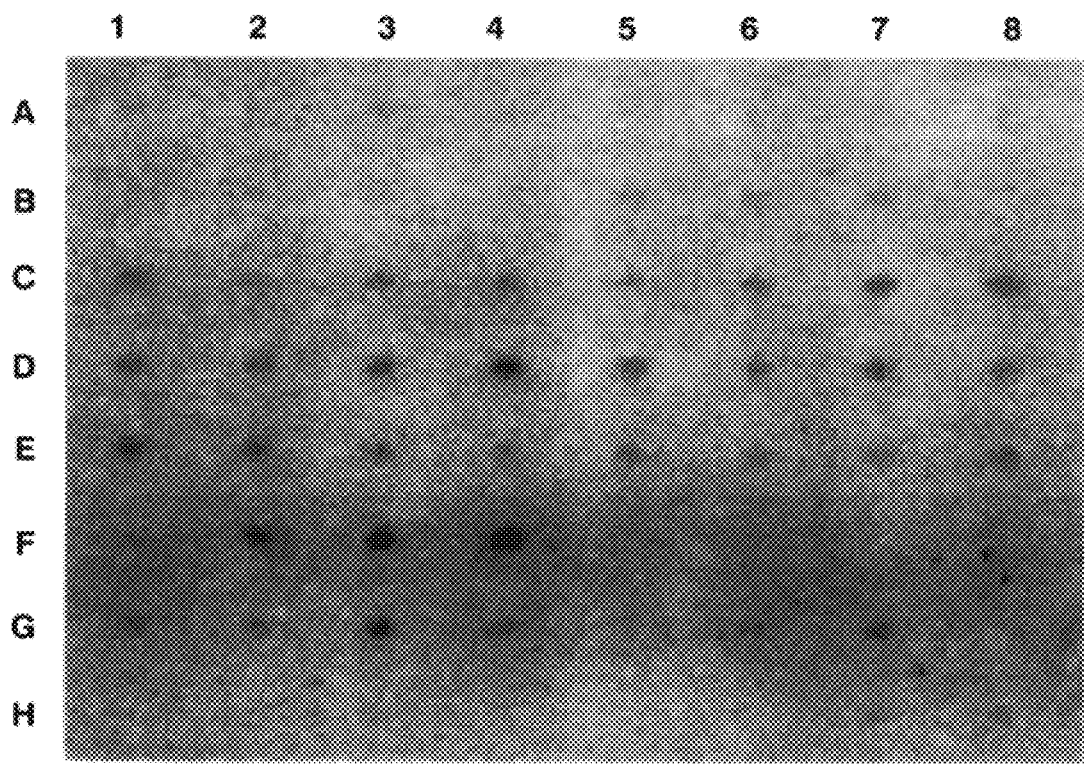

As an initial survey of artemin expression in adult and embryonic human tissues, a human master RNA blot (MRB) (CLONTECH) containing normalized samples of poly(A) RNA was probed with a random hexamer $^{32}$P-labeled fragment of the human artemin cDNA and signals were visualized using a Phosphorimager and (Molecular Dynamics). The results are shown in FIG. 5A.

Relatively low level expression was observed in many adult tissues, with the highest level in the pituitary gland, placenta and trachea. Among human fetal tissues, kidney and lung showed the highest level of expression. While little signal was visible in the adult and fetal brain, low-level expression of artemin mRNA was observed in structures of the adult basal ganglia (subthalamic nucleus, putamen, substantia nigra) and in the adult thalamus, suggesting artemin may influence subcortical motor systems. Expression was also observed in the spinal cord, however the RNA preparation from this tissue contains DRG material as well as spinal cord, which likely contributes to the observed expression (see FIG. 6).

Figure 6A:
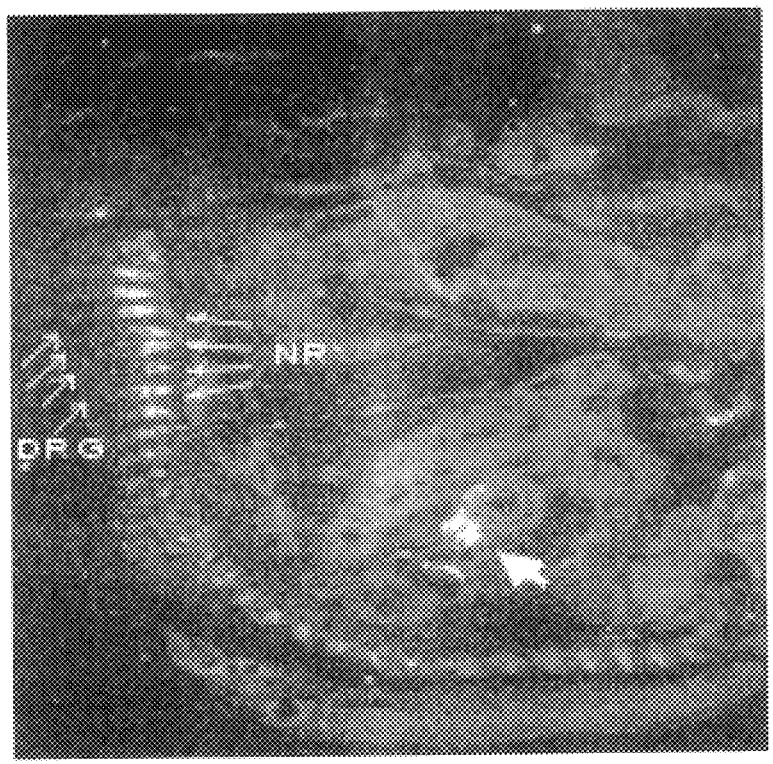
FIGS. 6A and 6B illustrate in situ hybridization analysis of artemin expression in embryonic rat using a $^{32}$P-labeled RNA probe generated from a rat artemin cDNA fragment as a probe, showing in FIG. 6A a sagittal section of an embryonic day 14 (E14) rat, with the section oriented such that the top is the rostral and the left side is the dorsal, in which no signal is observed in the dorsal root ganglia (DRG) and strong signal is observed in probable exiting nerve roots (NR), with the arrowhead indicating expression observed in tissue below the liver that likely represents a lateral extension of the superior mesenteric artery, and showing in FIG. 6B a parasagittal section of E14 rat in the same orientation as in (A), in which high level artemin expression surrounding the developing superior mesenteric artery (SMA) is detected.
Figure 6B:
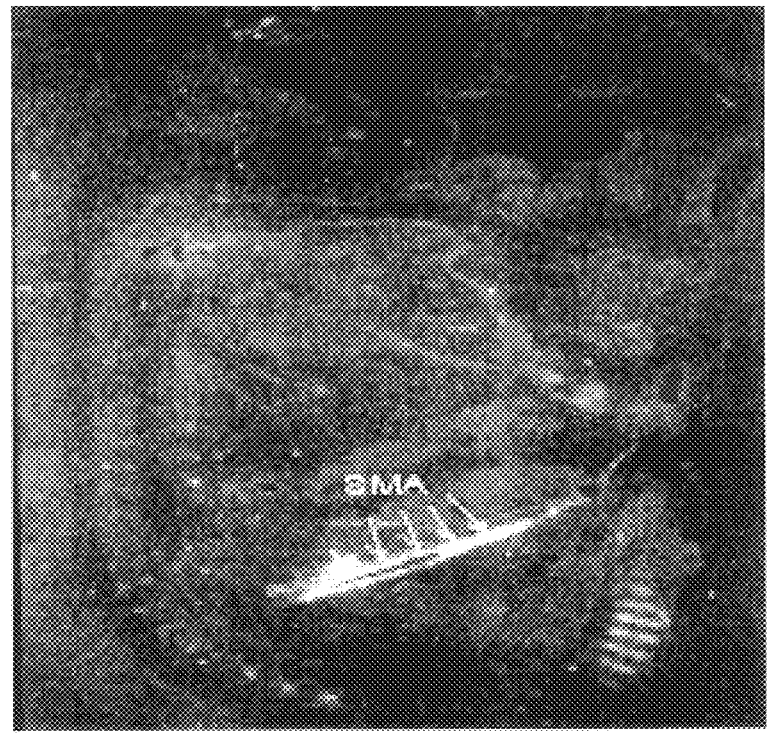

To more precisely localize artemin expression during embryogenesis, a fragment of the rat artemin cDNA was generated using PCR and cloned into pBluescript. Sense and anti-sense $^{33}$P-labeled RNA probes were generated from the cloned rat artemin cDNA fragment and used for in situ hybridization analysis of artemin mRNA expression in fresh-frozen embryonic day 14 (E14) rat embryos, which was performed as described previously (Araki et al., *Neuron* 17:353–361, 1998). The results are shown in FIGS. 6A and 6B.

No signal was observed in the brain or spinal cord at this embryonic age. The most striking expression was observed in the nerve roots, but not the developing neurons, of the dorsal root ganglia (DRG) (FIG. 6A). Furthermore, significant diffuse expression was also observed surrounding the superior mesenteric artery, corresponding to either the surrounding mesenchyme or expression by cell of the artery itself (FIG. 6B). These data suggest the possibility that artemin may act as a survival/trophic factor for peripheral neurons, either in a paracrine fashion for developing sensory neurons of the DRG, or as a target-derived factor for autonomic innervation of the superior mesenteric artery. Interestingly, among potential GFRα receptors, expression of artemin is most complementary with that of the orphan GFRα3, which is expressed at high levels in peripheral ganglia, but which has no detectable expression in the developing CNS by in situ hybridization (Baloh et al., 1998, supra; Trupp et al., *Mol. Cell. Neurosci.*, 11:47–63, 1998; Widenfalk et al., *Eur. J. Neurosci.* 10:1508–1517, 1998; Worby et al., *J. Biol. Chem.* 271, 23619–23622, 1998). No signal was detected using the sense probe on any tissue samples.

The expression of artemin in the developing nerve roots at E14 suggested it is produced by Schwann cell precursors or immature Schwann cells. To investigate if Schwann cells express artemin, semi-quantitative RT-PCR analysis was performed on cDNA libraries prepared from primary cultures of Schwann cells isolated from early post-natal rats, from myelinating Schwann cells from the adult sciatic nerve and from Schwann cells isolated from the distal segment of the sciatic nerve at 16 hours, 3 days or 7 days following nerve transection. Cultures of purified Schwann cells from early post-natal rats was performed as described by Brockes et al., *Brain Res.* 165:105–118, 1979. Sciatic nerve transection in adult rats and generation of reverse-transcribed cDNA were performed as described elsewhere (Araki et al., supra; Baloh et al., *Neuron* 18:793–802, 1997). cDNA samples from the libraries were normalized to levels of glyceraldehyde 3-phosphate dehydrogenase (GAPDH) and then amplified by RT-PCR using as forward primer 5'-TCGCGACGGTGGCTCACCGGTCTT-3' (SEQ ID NO:66) and as reverse primer 5'-GCACGAGCCGCTGCAGAAGCGGAA-3' (SEQ ID NO:67) and the following conditions: 95° C. for 2 min followed by 36 cycles of 95° C., 20 sec; 54° C., 30 sec; and 72° C., 30 sec.; and then a final incubation at 72° C., 2 min. Products were separated on a 3% agarose gel and stained with Ethidium Bromide.

Figure 6C:
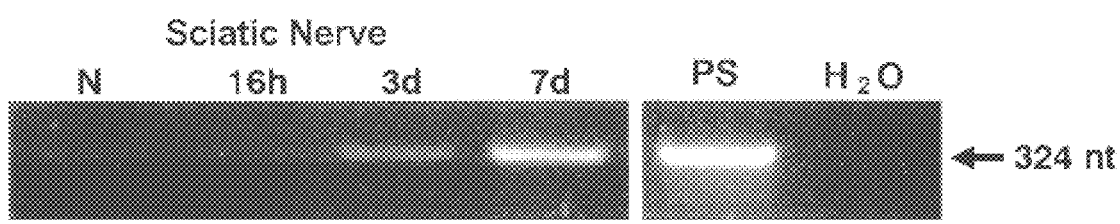
FIG. 6C illustrates semi-quantitative RT-PCR analysis of artemin expression in Schwann cells isolated from neonatal rats (PS), from the adult sciatic nerve (N), and from the distal segment of the sciatic nerve at the indicated times following nerve transection.

As shown in FIG. 6C, artemin is expressed at much higher levels in immature Schwann cells in culture than by mature myelinating Schwann cells (PS) of the adult sciatic nerve (N). However, artemin expression is up-regulated in the distal nerve segment after sciatic transection, a paradigm in which Schwann cells reacquire an immature state to support regenerating axons (reviewed in Scherer, *Curr. Opin Neurol.* 10:386–397, 1997). These data indicate that Schwann cells produce artemin, and furthermore suggest that artemin expression is regulated appropriately to influence developing and regenerating peripheral neurons.

EXAMPLE 3

This example illustrates the production of recombinant artemin protein.

A PCR fragment was generated which corresponded to the mature human artemin coding sequence (FIG. 3A), with an NdeI site and an 8-histidine tag on the 5' end, and a KpnI site on the 3' end, and then cloned directly into the corresponding sites of the pET30a(+) bacterial expression vector (Novagen). The artemin-encoding expression vector was transformed into the *E. coli* strain BL21 and recombinant human artemin protein was produced and purified as described previously for neurturin (Creedon et al., *Proc. Natl. Acad. Sci. USA* 94:7018–7023, 1997).

EXAMPLE 4

This example illustrates that artemin promotes the survival of peripheral neurons in vitro.

As shown above, expression of artemin suggests it may influence developing peripheral neurons, like GDNF and neurturin. To assess artemin's ability to support the survival of different peripheral neuronal populations in vitro, neurons from the dorsal root, trigeminal, nodose, and superior cervical ganglia (SCG) derived from postnatal day 1 (P1) Sprague-Dawley rats (Harlan Sprague-Dawley, Ind.) were cultured in the presence of artemin, GDNF, neurturin or persephin. Each GDNF ligand family member consisted of the human mature amino acid sequence and was produced by standard recombinant DNA methods. Recombinant GDNF, neurturin and persephin were obtained from Genentech while recombinant artemin was produced as described in Example 3.

The cultures were performed using standard methods described elsewhere (Kotzbauer et al., *Neuron* 12:763–773, 1994; Kotzbauer et al., *Nature* 384:467–470, 1996; Milbrandt et al., *Neuron* 20:245–253, 1998). In brief, for SCG neurons, after dissection and dissociation, neurons were plated on collagen-coated 24-well tissue culture plates and maintained in NGF-containing medium (AM50) for 5 days, after which they were either kept in AM50 or switched to medium containing neutralizing anti-NGF antibodies plus GDNF, neurturin, persephin, artemin, (50 ng/ml where not noted otherwise), or no growth factors. Cultures were maintained for 3 days, after which they were fixed in 4% paraformaldehyde and stained with toluidine blue, and surviving neurons were counted. For nodose ganglion and dorsal root ganglion neuron cultures, dissociated neurons were plated directly into NGF (for dorsal root ganglia), or BDNF (for nodose ganglia, 100 ng/ml) or one of the GDNF ligands in serum-containing medium (AM50 with anti-NGF antibodies), and cells surviving after 3 days in culture were counted as above. Trigeminal ganglia were dissected, dissociated, and plated directly into medium containing NGF or the indicated GDNF ligands, and the number of surviving cells was assessed after 3 days in vitro. For all culture systems, 2–3 independent experiments were performed. The results are shown in FIGS. 7A–7E.

Figure 7A:
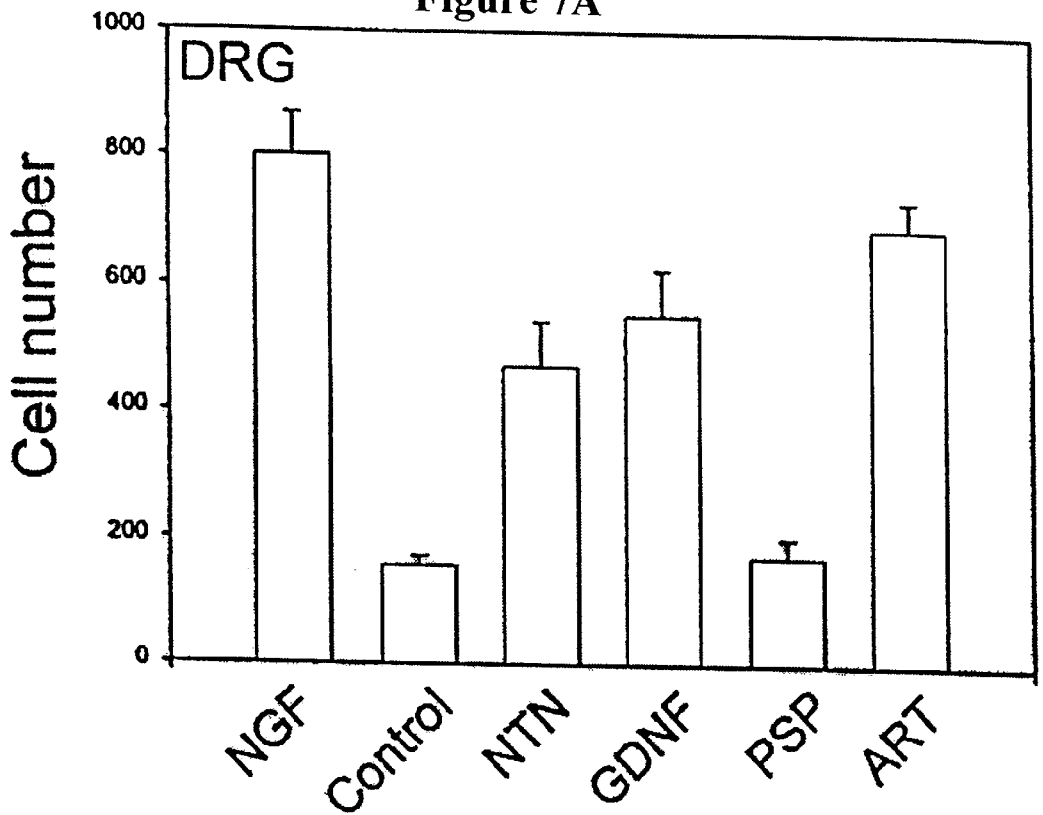
Figure 7B:
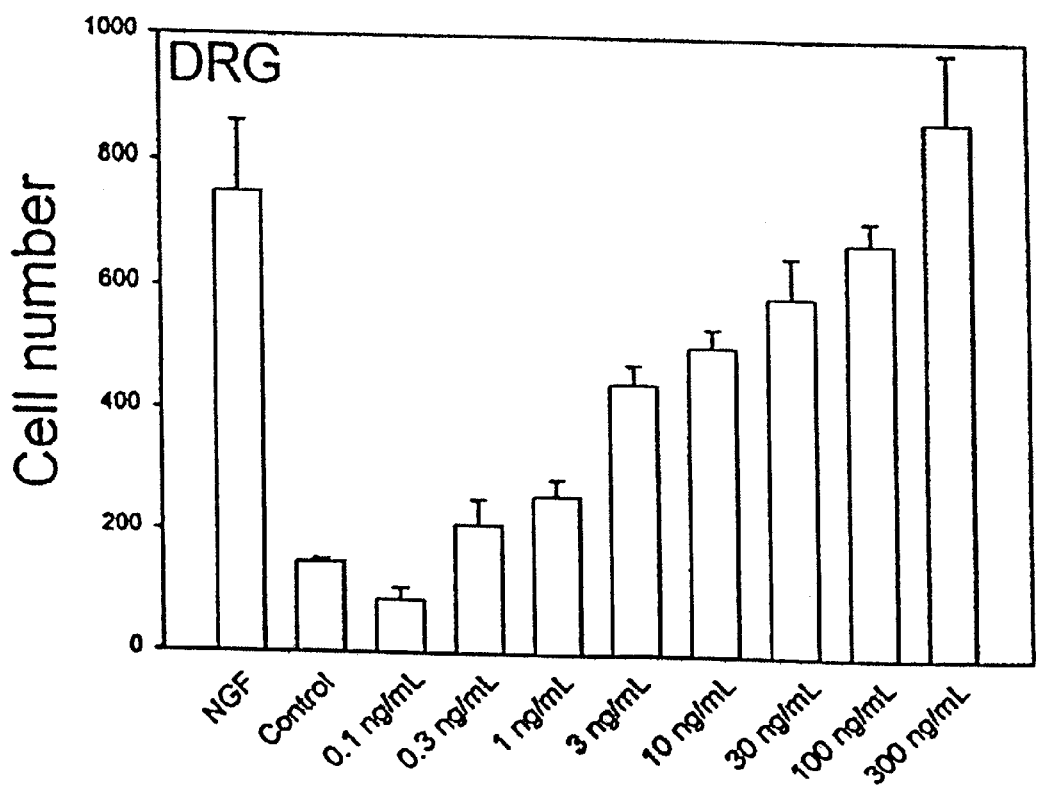
Figure 7C:
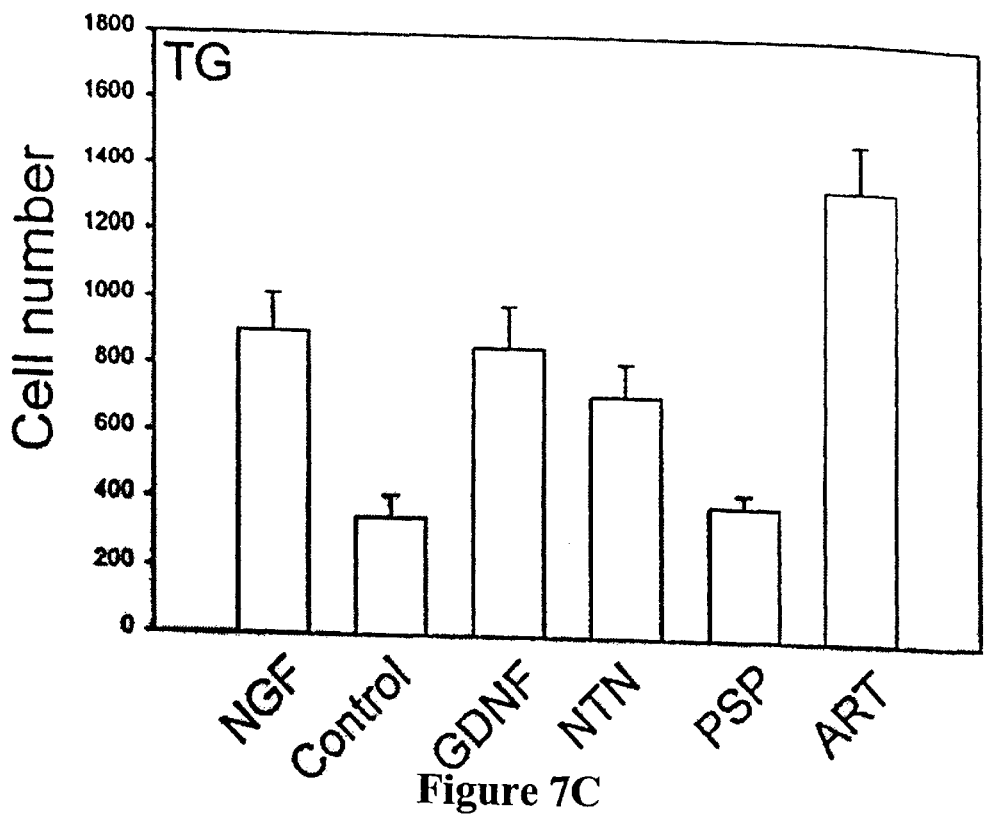

Like GDNF and neurturin (NTN), artemin (ART) supported the survival of a subset of sensory neurons from both the dorsal root ganglion (DRG) and the trigeminal ganglion (TG), whereas persephin (PSP) did not (FIG. 7A and 7C). Interestingly, in both these populations of sensory neurons ART supported a larger number of neurons than GDNF or neurturin, and supported a similar (DRG) or a greater number (TG) of neurons than NGF. Dose response analysis of artemin's survival promoting effect on DRG neurons (FIG. 7B) revealed an $EC_{50}$ of 1–3 ng/ml, ~$10^{-}$M.

Figure 7D:
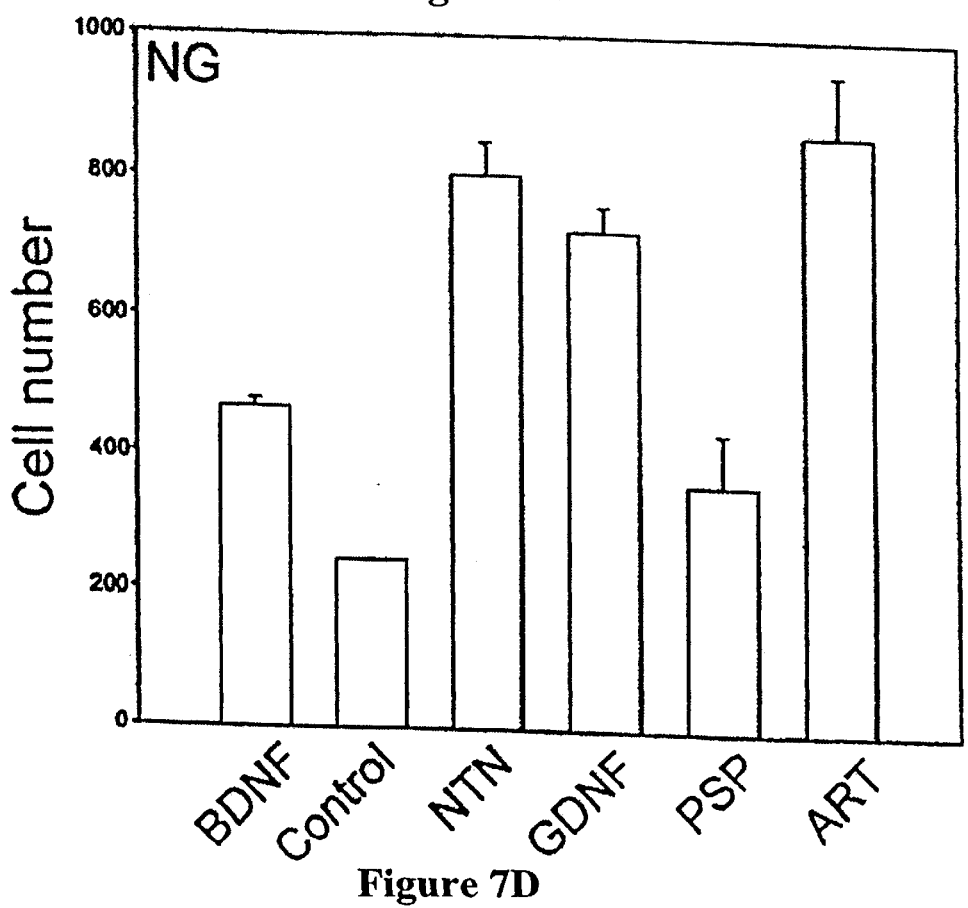
Figure 7E:
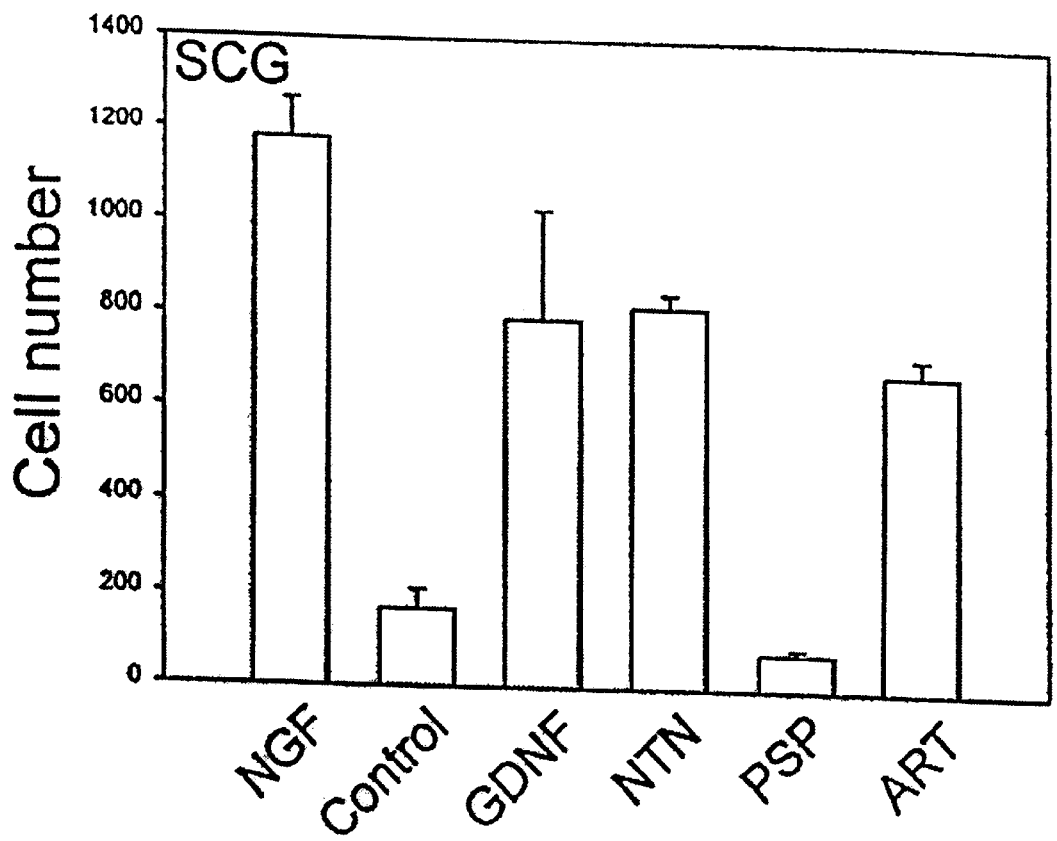

With respect to visceral sensory neurons of the nodose ganglion (NG), which consists of a large number of neurons responsive to the neurotrophin BDNF (Lindsay et al., 1985), artemin, GDNF, and neurturin supported similar numbers of NG neurons, and each factor yielded equal or greater survival promotion than BDNF (FIG. 7D). These results were similar to previous reports (Kotzbauer et al., 1996, supra; Trupp et al., 1995, supra).

Artemin also supported the survival of SCG neurons in culture (FIG. 7E), although fewer neurons were supported by artemin than by GDNF or neurturin. In contrast to the sensory neurons examined above, none of the GDNF family ligands supported as many neurons as NGF. Therefore, similar to GDNF and neurturin, and as consistent with its embryonic expression pattern, artemin is a survival factor for sensory and sympathetic peripheral neurons in culture.

EXAMPLE 5

This example illustrates that RET-expressing neuroblastoma cell lines are responsive to artemin.

Neuroblastoma cell lines are derivatives of peripheral sympathetic neuroblast tumors that respond to GDNF and neurturin and display a variety of GFRα/RET receptor profiles (Hishiki et al., Cancer Res. 58:2158–2165, 1998; Tansey et al., submitted). Artemin's ability to influence several of these neuronal cell lines was investigated to determine if responsive cells had a consistent receptor profile.

Figure 8A:
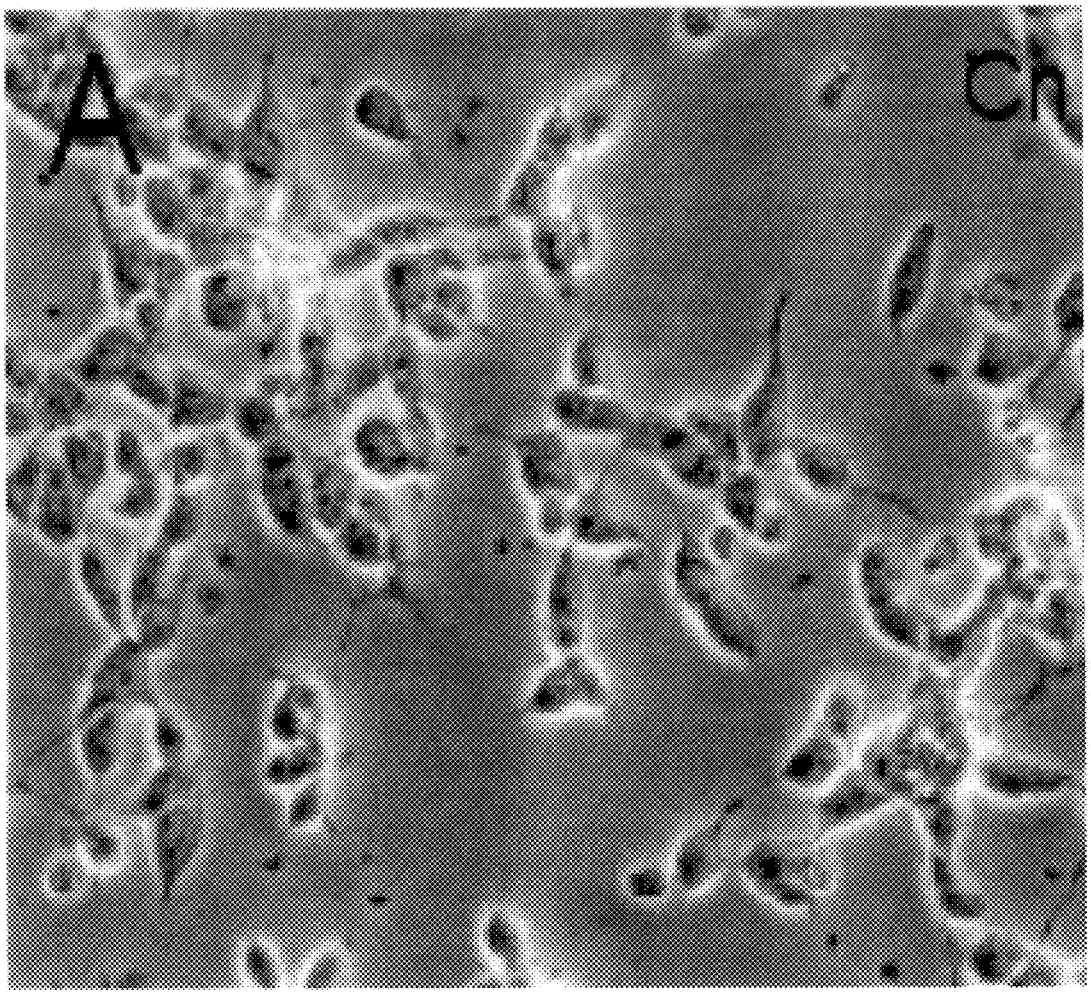
FIGS. 8A–D illustrate that artemin induces differentiation and proliferation in neuroblastoma cell lines showing in FIGS. 8A–8C photographs of SK-SY5Y neuroblastoma cells cultured in the presence of no factor (Cn) (FIG. 8A), 10 µM all-trans retinoic acid (RA), a known inducer of differentiation of these cells (FIG. 8B), or 50 ng/mL artemin (ART) (FIG. 8C), and in FIG. 8D a histogram of BrdU incorporation by NBL-S neuroblastoma cells in the presence of 50 ng/mL of the indicated factor.
Figure 8B:
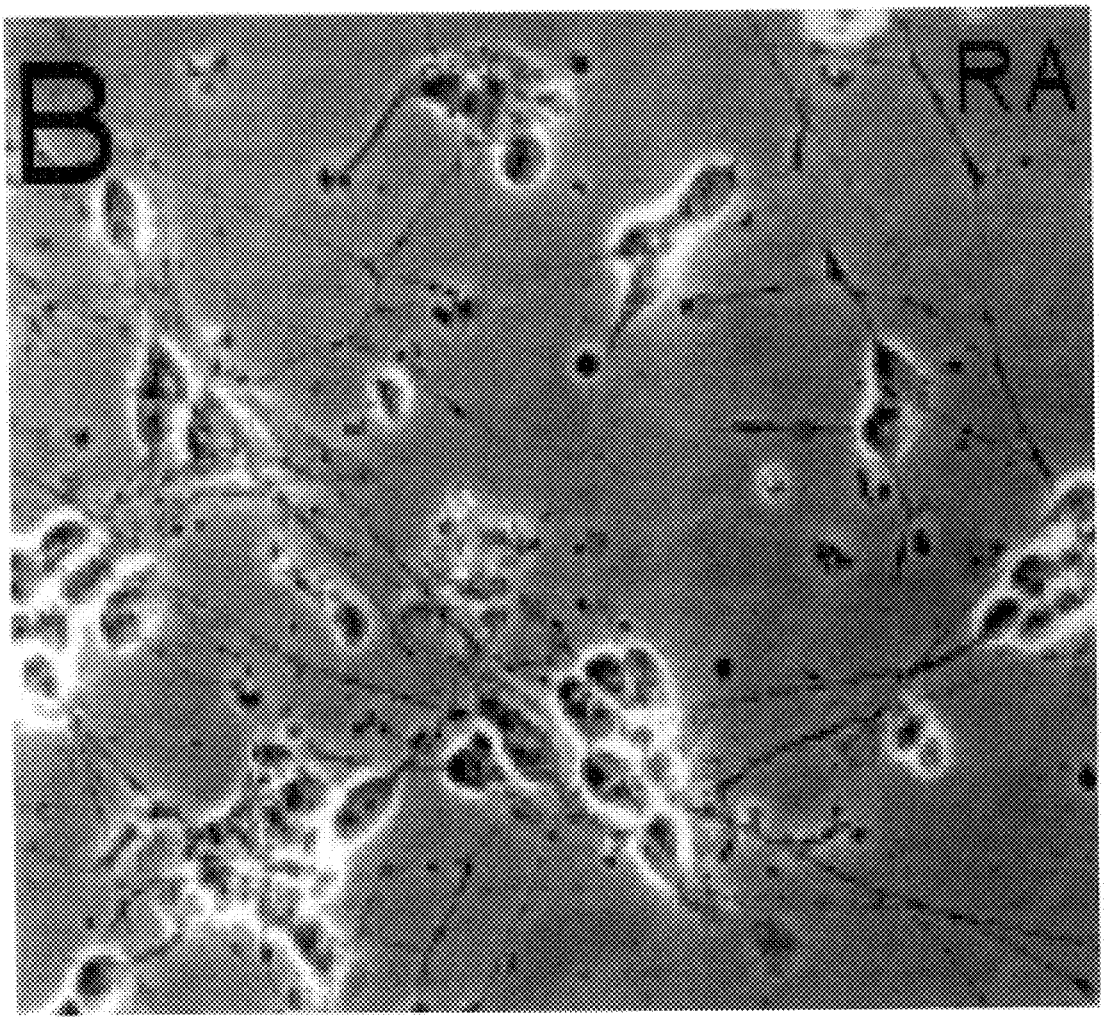
Figure 8C:
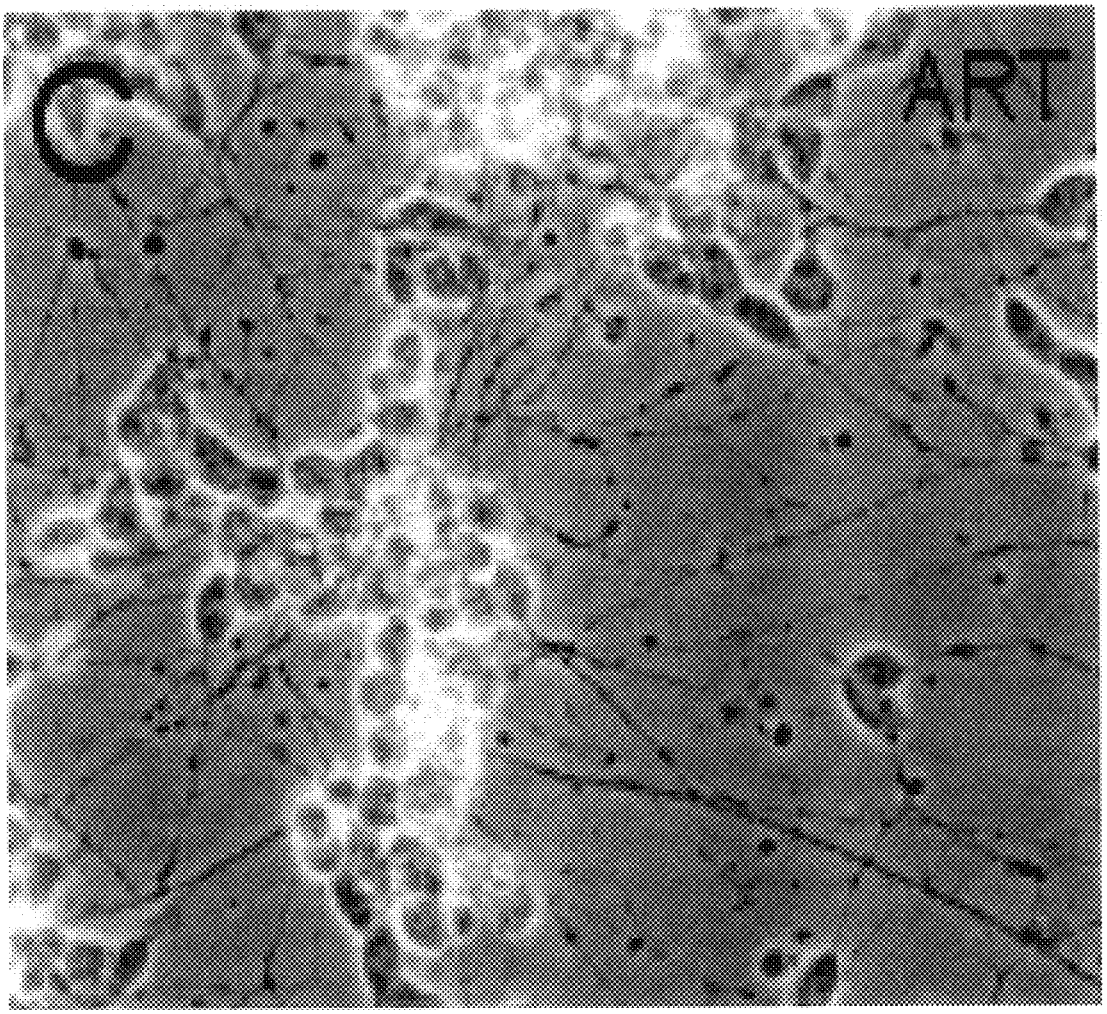

In one experiment, cells from the SH-SY5Y neuroblastoma cell line were plated at $2\times10^5$ cells/ml/well in 12-well tissue culture plates. After one day in culture cells were either left untreated (Cn) or stimulated with 50 ng/ml artemin (ART) or 10 μM retinoic acid (RA), a known inducer of differentiation of SH-SY5Y cells. Three days after factor addition, differentiation was assessed and cells were photographed. As shown in FIGS. 8A–8C, artemin and retinoic acid induced strong differentiation responses in the SH-SY5Y cell line as indicated by their robust neurite outgrowth and neuronal morphology.

Figure 8D:
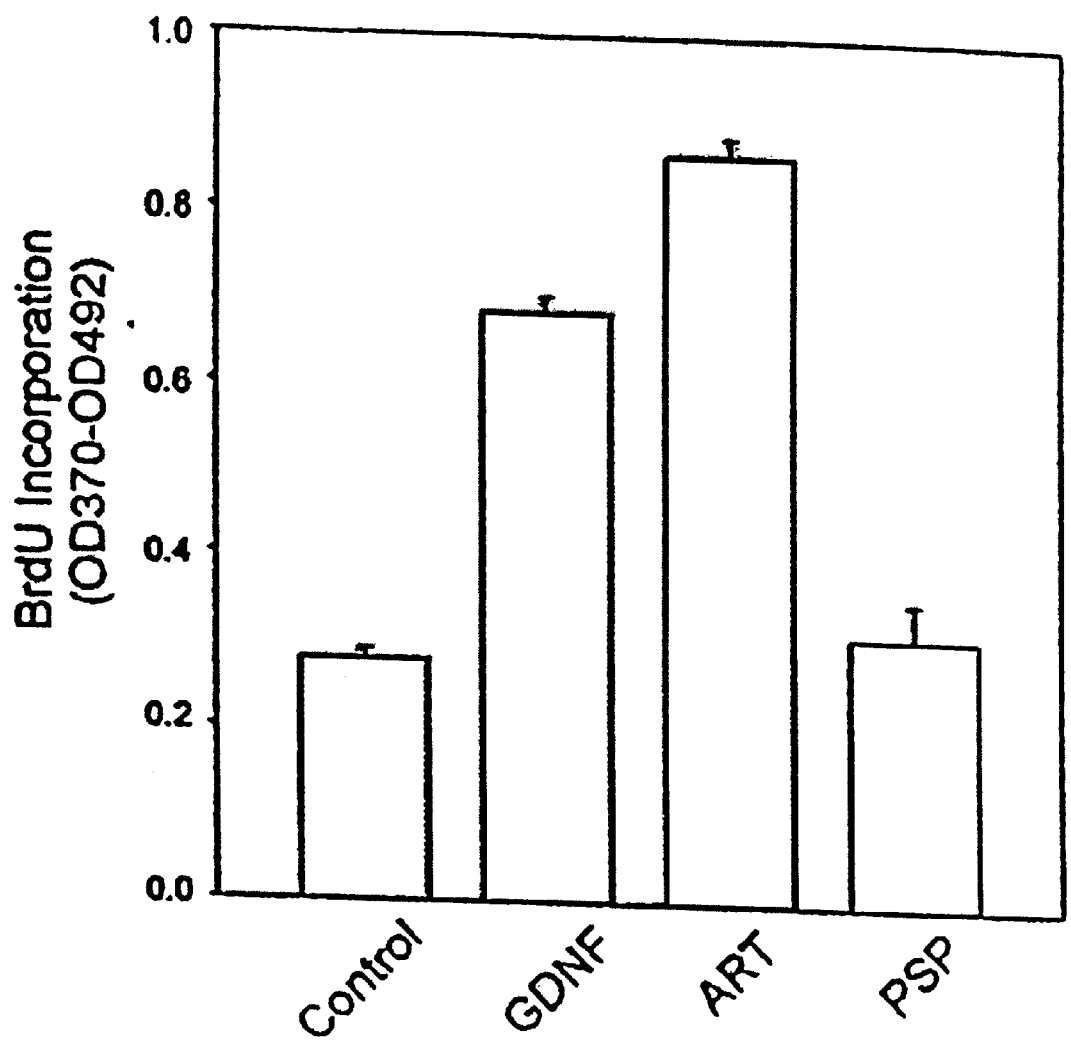

In another experiment, the ability of artemin to induce proliferation of the NBL-S neuroblastoma cell line was examined. NBL-S cells were plated at $5\times10^4$ cells/well on 48-well plates in standard medium, either without treatment or in the presence of 50 ng/mL of GDNF, artemin, or persephin. Actively dividing cells undergoing DNA synthesis 30 hrs after factor addition were detected using the BrdU (colorimetric) cell proliferation assay kit according to the manufacturer's instructions (Boehringer-Mannheim) and the data are shown in FIG. 8D. Like GDNF, artemin stimulated proliferation of NBL-S cells, whereas persephin did not.

To confirm that RET was a required component of the artemin receptor, the responsiveness of the neuroblastoma cell lines CHP126, CHP134, and SAN, which do not express RET, were examined. These cell lines did not respond to GDNF, neurturin or artemin (data not shown). Because both the SH-SY5Y and NBL-S cell lines express GFRα1, GFRα2, and GFRα3, as well as RET, these experiments did not suggest the usage of a particular coreceptor by artemin.

EXAMPLE 6

This example illustrates that artemin supports the survival of dopaminergic neurons.

As shown above, artemin expression was not observed in the brain or spinal cord of embryonic rats at the age examined and was not observed in the fetal human brain, but was present at very low levels in some adult brain regions. Therefore artemin's ability to influence dopaminergic neurons from the rat embryonic ventral midbrain was compared to the survival promoting activity of the other GDNF ligand family members.

Figure 7F:
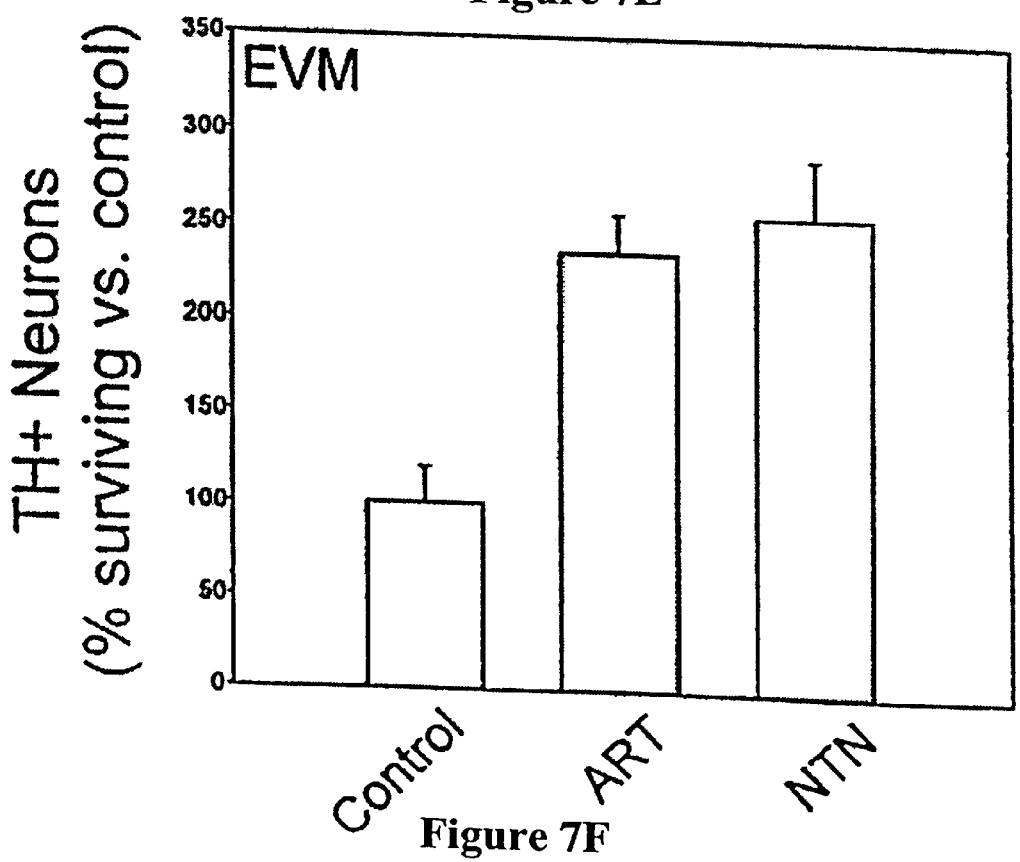

Embryonic day 14 ventral mesencephalon cultures were prepared by removing the entire mesencephalon into cold Leibovitz's L15+6 mg/ml glucose and dissecting the tissue while keeping it on ice. Following dissection, the tissue was digested in a mixture of dispase (1 mg/ml, Sigma) and collagenase (1 mg/ml, Worthington Biochemical) for 25 min. Tissue was then washed twice with modified N2 media and triturated 35 times. Cell density and viability was assessed using a hemocytometer to count trypan blue excluding cells. Cells were plated at 20,000 cells/well on 8-well chamber slides (coated with 125 ng/ml poly-D-lysine and 25 ng/ml laminin) in serum-free medium consisting of DME/Hams F12 (1:1), 1 mg/ml BSA, 5 μM insulin, 10 nM progesterone, 100 μM putrescine, 30 nM selenium, 10 ng/ml rat transferrin, 100 U/ml penicillin, 100 U/ml streptomycin. Factors were added within 15 min of plating. After 3 days in culture, the cells were fixed, stained for tyrosine hydroxylase, and the number of tyrosine hydroxylase staining (TH+) neurons were counted. The results from two independent experiments are shown in FIG. 7F as the percentage of surviving TH+ neurons over control.

Interestingly, artemin supported the survival of dopaminergic midbrain neurons, although there is no apparent artemin expression in the ventral midbrain at this age. Therefore, artemin can promote survival of central as well as peripheral neurons, and indicates that receptors for artemin are present in both these populations.

In summary, all of the biological responses of artemin in peripheral and central neurons, and in neuronal cell lines, suggest that artemin utilizes receptor components similar to or overlapping with GDNF and neurturin.

EXAMPLE 7

This example illustrates that artemin signals through RET using the former orphan receptor GFRα3 as a coreceptor.

Because artemin, GDNF and neurturin exhibit similar activity profiles for peripheral and central neuronal populations and because artemin's activity correlated with RET expression in neuroblastoma cell lines, artemin's ability to activate RET in primary cultured SCG neurons and in the artemin-responsive neuroblastoma cell line NBL-S was examined by performing Western blot analysis of Ret phosphorylation and MAP kinase activation as described previously (Baloh et al., 1997, supra; Creedon et al., 1997, supra).

In brief, SCG neurons were dissected from postnatal day 1 (P1) rats and maintained in NGF-containing medium for 5 days, after which they were deprived of NGF by switching to NGF-free medium in the presence of anti-NGF antibodies. After 2 hours without NGF, neurons were switched to medium containing NGF, GDNF or artemin at 50 ng/ml for 20 minutes. Cells were washed in cold PBS, and collected in immunoprecipitation buffer (1 mM EDTA/1 mM EGTA/0.2 mM $NaVO_3$/1 mM Pefabloc/1 uM pepstatin A/10 ug/ml leupeptin/2 ug/ml aprotinin/1% Triton X-100/0.5% Nonidet P40/150 mM NaCl in 10 mM Tris, pH 7.4). The lysates were incubated with 30 μl agarose-conjugated anti-phosphotyrosine antibodies (Calbiochem) at 4° C. for 1 hr. Beads were then washed three times with immunoprecipitation buffer, resuspended in SDS sample buffer, and boiled for 5 min. Samples were separated using SDS-PAGE, and transferred to nitrocellulose membranes. Membranes were blocked for 1 hr at 25° C. in TBS containing 5% dry milk, incubated overnight 4° C. with a 1:300 dilution of anti-Ret antibody (C-19; Santa Cruz), then washed (3× in TBS containing 0.1% Tween-20) and incubated in a 1:10,000 dilution of anti-rabbit antibodies conjugated to HRP (Jackson Immunoresearch). Membranes were washed 3×, incubated with SuperSignal ULTRA (Pierce) for 5 minutes, then exposed to film. For MAP kinase (MAPK) assays, a portion of the total lysate wars removed before immunoprecipitation, separated by SDS-PAGE, and immunoblotted using an anti-phospho-MAP-kinase antibody (New England Biolabs).

NBL-S cells were plated at $3 \times 10^5$ cells/well in 6-well plates, and after 46 hr switched to low-serum (0.5%) medium for 2 hr, and then stimulated with NGF, GDNF or artemin (50 ng/ml) for 20 min. Cells were then collected and analyzed as above. For PI-PLC treatment, a parallel set of NBL-S cells were plated as above but treated with 500 mU/ml of PI-PLC (Boehringer-Mannheim) for 1 hr, and washed with PBS and stimulated with factors as above.

Figure 9A:
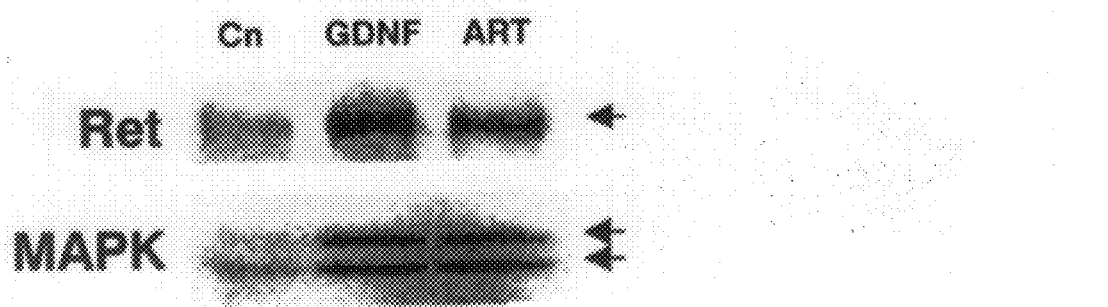
FIG. 9A illustrates that artemin activates RET and downstream signaling in primary cultured SCG neurons showing an immunoblot of tyrosine phosphorylated RET or phosphorylated MAPK (MAPK) in lysates from SCG neurons treated with either no factor (Cn), GDNF, or artemin (ART) at 50 ng/ml.
Figure 9B:
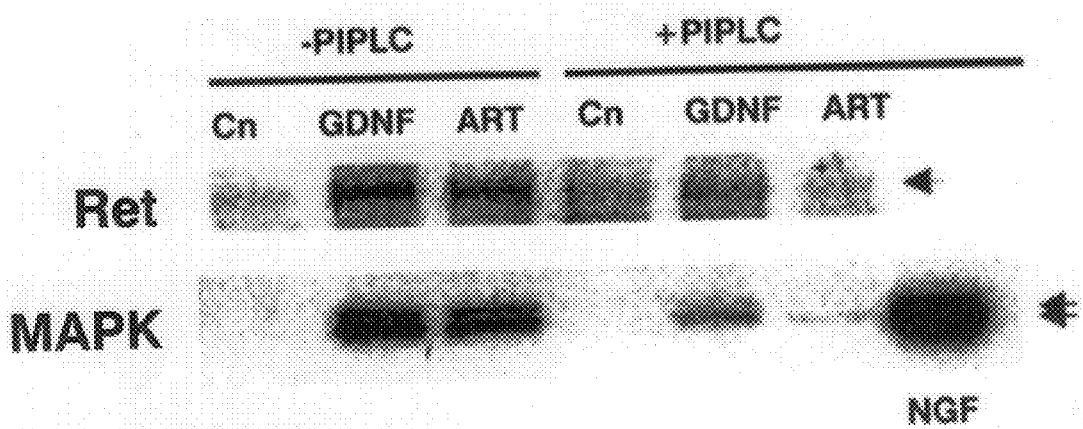
FIG. 9B illustrates that artemin activates RET in NBL-S neuroblastoma cells, showing an immunoblot of tyrosine phosphorylated RET or phosphorylated MAPK (MAPK) in lysates from NBL-S cells stimulated as in FIG. 9A in the absence or presence of the enzyme PI-PLC, which specifically cleaves GPI-anchored proteins from the cell surface.

The results are shown in FIGS. 9A and 9B. Like GDNF, artemin induced tyrosine-phosphorylation of RET in SCG neurons and in the NBL-S cell line, and this activation was effective in eliciting downstream signaling as measured by activation of the MAP kinase pathway. Furthermore, pretreatment of the NBLS cell line with the enzyme PI-PLC, which specifically cleaves GPI-anchored proteins from the cell surface, abolished artemin's ability to activate RET and all downstream signaling, but as expected had no effect on NGF signaling (FIG. 9B). Therefore, these data indicate that like the other members of the GDNF ligand family, artemin signals through the RET receptor tyrosine kinase, and requires a GPI-anchored coreceptor to do so.

Figure 9C:
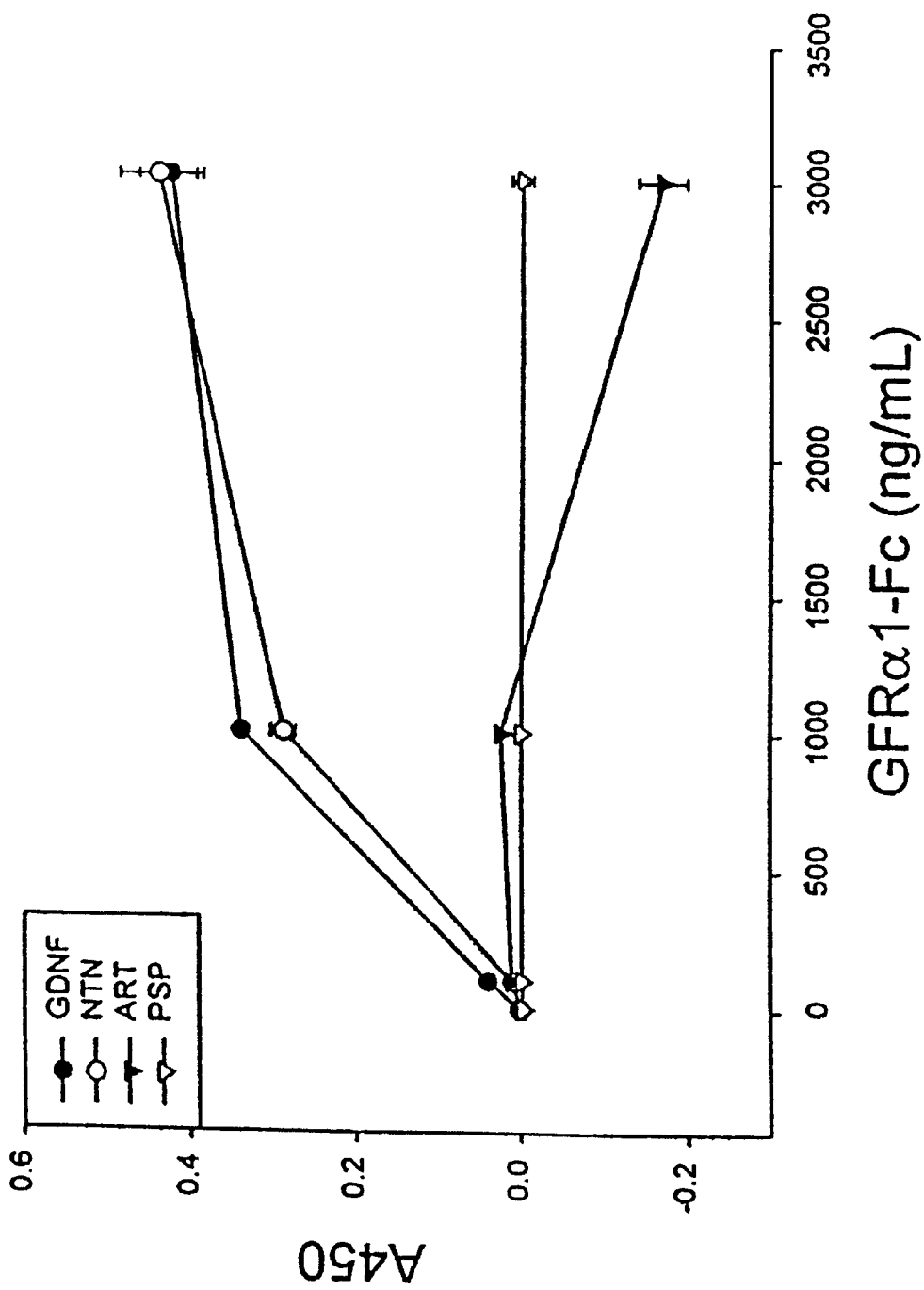
FIGS. 9C–9E illustrate the direct binding of GRFα1-Fc, GFRα2-Fc, and GFRα3-Fc receptor bodies to GDNF ligand family members showing graphs of the amount of absorbance at 450 mn plotted against increasing concentrations of the indicated soluble GFRα-Fc fusion protein added to microtiter plates coated with GDNF, neurturin, artemin or persephin, which were then treated with anti-human Fc antibodies conjugated to horseradish peroxidase (HRP) and binding of receptor bodies measured using the chromogenic HRP substrate 3,3',5,5'-tetramethylbenzidine, with error bars representing the standard deviation of duplicates from a representative experiment.
Figure 9D:
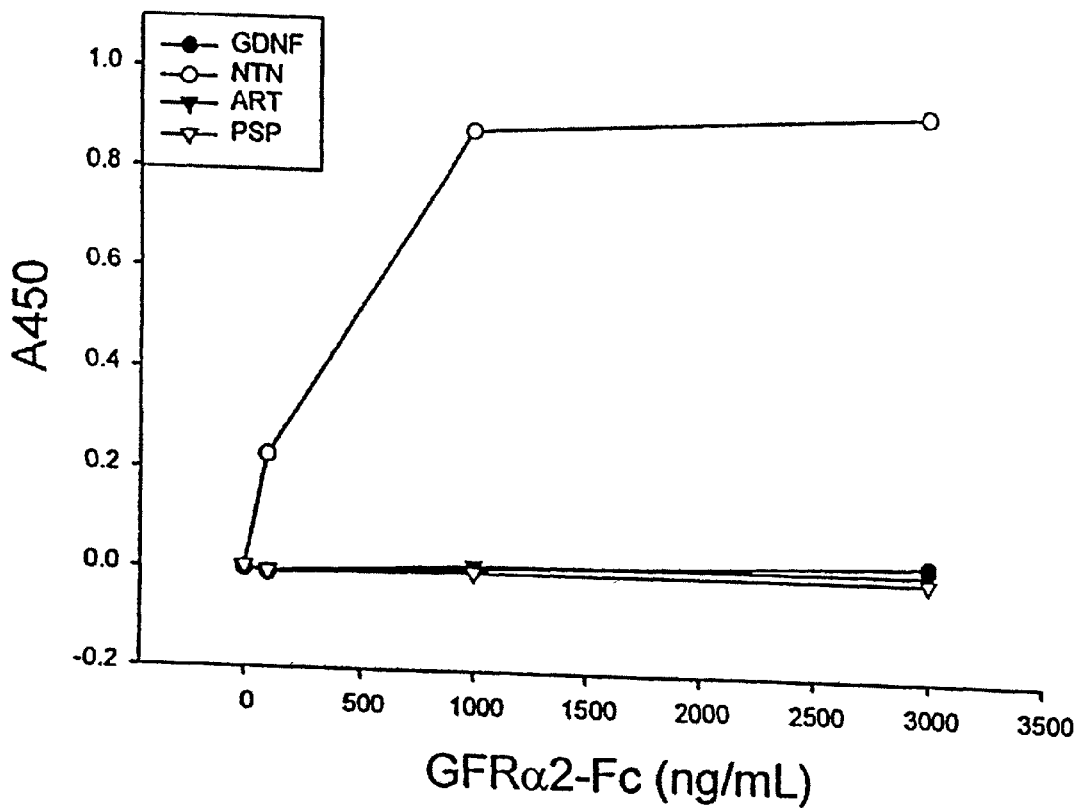
Figure 9E:
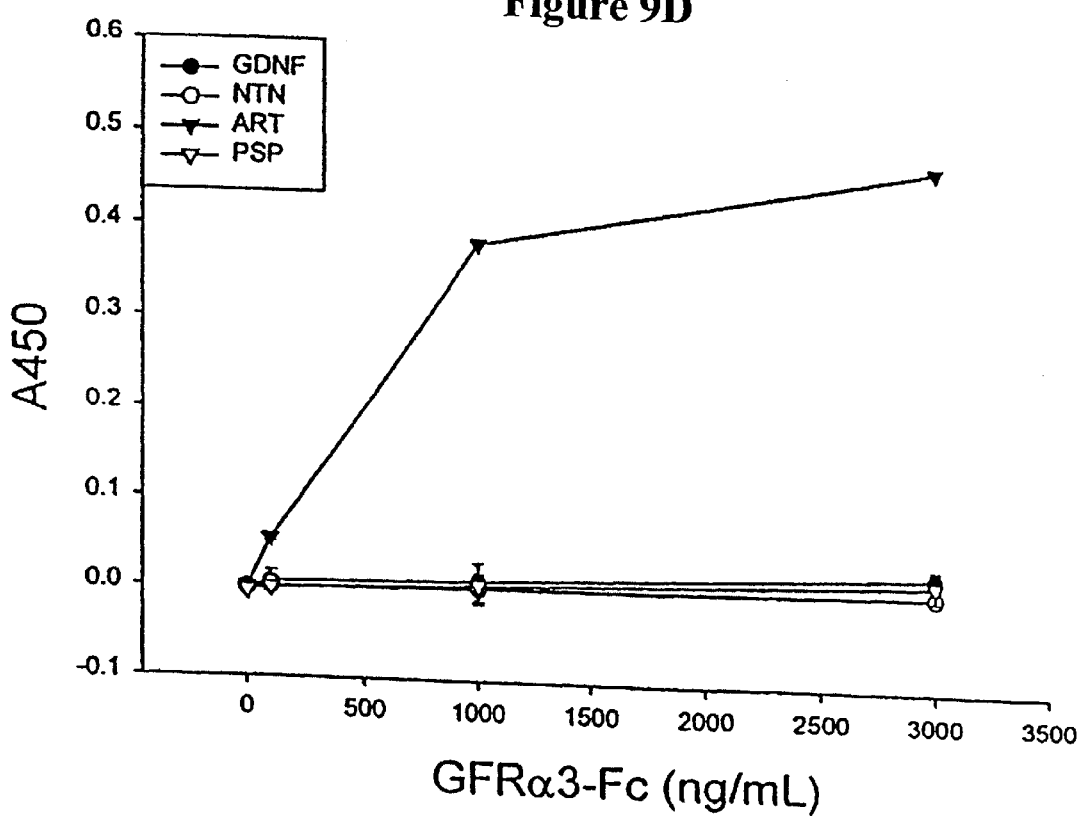

To investigate which if any of the known coreceptor(s) artemin can utilize to activate RET, its ability to directly bind to soluble Fc-fusion forms of GRFα1, GFRα2, or GFRα3 was assessed. GFRα1-Fc, GFRα2-Fc and GFRα3-Fc fusion proteins were obtained from R&D Systems. Binding assays were performed similarly to assays previously described (Sanicola et al., *Proc. Natl. Acad. Sci., USA* 94:6238–6243, 1997). Recombinant GDNF, neurturin, artemin, persephin, or purified bovine serum albumin (BSA; Pierce) were coated to Nunc-Immuno MaxiSorp microtiter plates at 325 ng/ml in TBS (10 mM Tris-HCl pH 7.5, 150 mM NaCl) for 1 hour at 25° C. Plates were washed (3× in TBS/0.03% Tween-20), and then blocked (blocking solution: TBS/1% BSA) for 1 hr at 25° C. Receptor bodies diluted in blocking solution were added and incubated for 2 hr at 25° C., washed 5×, then incubated with 1:10,000 dilution of HRP-conjugated anti-human Fc antibodies in blocking solution (Jackson Immunoresearch) for 45 minutes at 25° C. Finally, wells were washed 5× and the presence of HRP was assayed by addition of the chromogenic substrate 3,3', 5,5-tetramethylbenzidine for 5 min. The reaction was stopped by adding an equal volume of 0.5M $H_2SO_4$, and color was measured in a plate reader at 450 nm. Non-specific binding of receptor bodies to the plates was measured in BSA coated wells, and this binding was subtracted from all other measurements. All experiments were performed in duplicate and the results are shown in FIGS. 9C–9E.

In this assay, GFRα1-Fc was able to bind to both GDNF and neurturin with similar affinity, but not to persephin or artemin. GFRα2-Fc bound to neurturin but not to GDNF or artemin, consistent with previous reports that GDNF can only bind to GFRα2 in the presence of RET (Sanicola et al., 1997). Interestingly, the former orphan receptor GFRα3-Fc was able to bind to artemin, but not to any of the other GDNF ligand family members, consistent with the inability of GFRα3 and RET to form a functional receptor complex for GDNF, neurturin or persephin (Baloh et al., 1998, supra; Worby et al., 1998, supra). Each of the receptor bodies bound to their respective ligands with an apparent Kd of ~3 nM, which is similar to the previously reported affinity between GFRα1-Fc and GDNF in this assay (Sanicola et al., 1997). Therefore, artemin can bind to the former orphan receptor GFRα3, with an affinity similar to GDNF and NTN binding to their respective receptors.

While the binding data above suggest that GFRα3/RET is the functional receptor for artemin, such direct binding studies alone have been unreliable in predicting all GDNF family receptor interactions because of the observation that RET can modulate receptor binding (Sanicola et al., 1997, supra). Thus, to directly test which receptor combinations can form fimetional receptors for artemin, expression plasmids for the individual GFRα coreceptors together with the Gal4-Elk/Gal4-Luc reporter system were transiently transformed into fibroblasts that stably express RET. This system, which utilizes the ability of the Gal4-Elk fuision protein to respond to MAP kinase activity and activate transcription of the Gal4-luciferase reporter, has been used previously to monitor NGF/TrkA activation of the MAP kinase pathway in PC12 cells (Vossler et al., *Cell* 89:73–82, 1997; York et al., *Nature* 392:622–626, 1998), and GDNF/RET activation of MAP kinase in neuroblastoma cell lines (Worby et al., 1998, supra; Worby et al., *J. Biol. Chem.* 271:23619–23622, 1996).

Generation of the expression plasmids for rat GFRα1 and human GFRα2, as well as MG87 fibroblasts stably expressing human RET (RET-3T3), were described in detail previously (Baloh et al., 1997, supra; Creedon et al., 1997, supra). For generation of the GFRα3 expression plasmid, a fragment containing the complete coding region of human GFRα3 was PCR-amplified from a human pituitary cDNA library, and this fragment was directly cloned into the KpnI and BamHI sites of pCB6 (Brewer, *Methods in Cell Biol.* 43:233–245, 1994) using sites engineered into the PCR primers. The GAL4-Elk1 chimera expression plasmid was a gift of P. Stork (Vollum Institute, Oregon Health Sciences University).

NLF neuroblastoma cells, which naturally express GFRα2/RET (Tansey et al., submitted), or the RET-3T3 cells were plated at 85,000 cells/well in 12-well plates, and cotransfected with the reporter plasmids Gal4-Luc and CMV-Gal4-Elk (250 ng/well and 50 ng/well, respectively), CMV-lacZ (50 ng/well) for transfection normalization, one of the CMV-GRFα expression plasmids (500 ng/well), and pBluescript (650 ng/well) as carrier for a total of 1.5 μg DNA/well using the Superfect reagent (Qiagen) according to the manufacturer's instructions. RET-3T3 fibroblasts were exposed to DNA/Superfect mixtures at 37° C. overnight, washed and placed in low-serum (0.5%) medium, and stimulated with 50 ng/ml GDNF, artemin or persephin for 6–8 hours before collection (48 hours post-transformation). NLF neuroblastoma cells were exposed to DNA/Superfect mixtures for 2 hours, placed in full-serum medium overnight for recovery, and then switched to low-serum (0.5%) medium containing 50 ng/m of GDNF, artemin or persephin for 24 hours before collection (48 hours post-transformation). Measurement of luciferase and β-galactosidase activity was measured using a luminometer and performed as described (Svaren et al., *EMBO J* 17:6010–6019, 1998). The average luciferase activity of duplicate samples was normalized to β-galactosidase activity of the cotransformed lacZ reporter, and fold activation was calculated by dividing the normalized activity in factor-treated cells by that in the no treatment control.

Figure 10A:
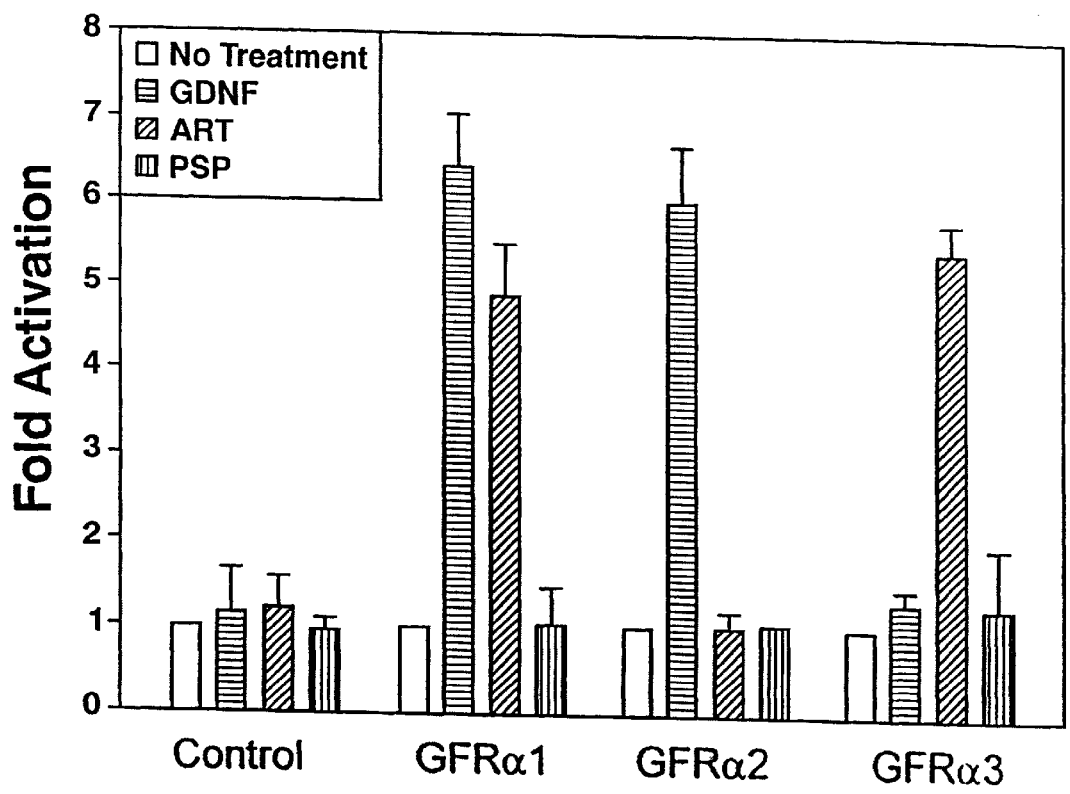
FIGS. 10A and 10B illustrate receptor activation by GDNF ligand family members in the presence of defined coreceptor components showing bar graphs of the amount of luciferase expression induced by the indicated growth factor in RET-expressing MG87 fibroblasts (RET-3T3) (FIG. 10A) or in NLF neuroblastoma cells (NLF) (FIG. 10B) transiently transformed with the Gal4-Elk/Gal4-Luc reporter system together with an expression plasmid for the indicated coreceptor or the CMV plasmid with no insert (Control), with fold-activation determined by dividing luciferase activity in the indicated treatment condition by the no treatment control, and error bars representing the standard deviation of duplicate measurements from a representative experiment.

As seen in FIG. 10A, consistent with previous reports in multiple systems, GDNF activated RET signaling in cells expressing GRFα1/RET or GFRα2/RET, but not GFRα3/RET (Baloh et al., 1998; Baloh et al., 1997; Jing et al., 1997; Sanicola et al., 1997; Suvanto et al., 1997; Worby et al., 1998). As predicted from the binding data, artemin was able to activate GFRα3/RET, but not GFRα2/RET receptor complexes. Interestingly, artemin was also able to activate RET in cells expressing GFRα1/RET, although to a lesser degree than GDNF.

Figure 10B:
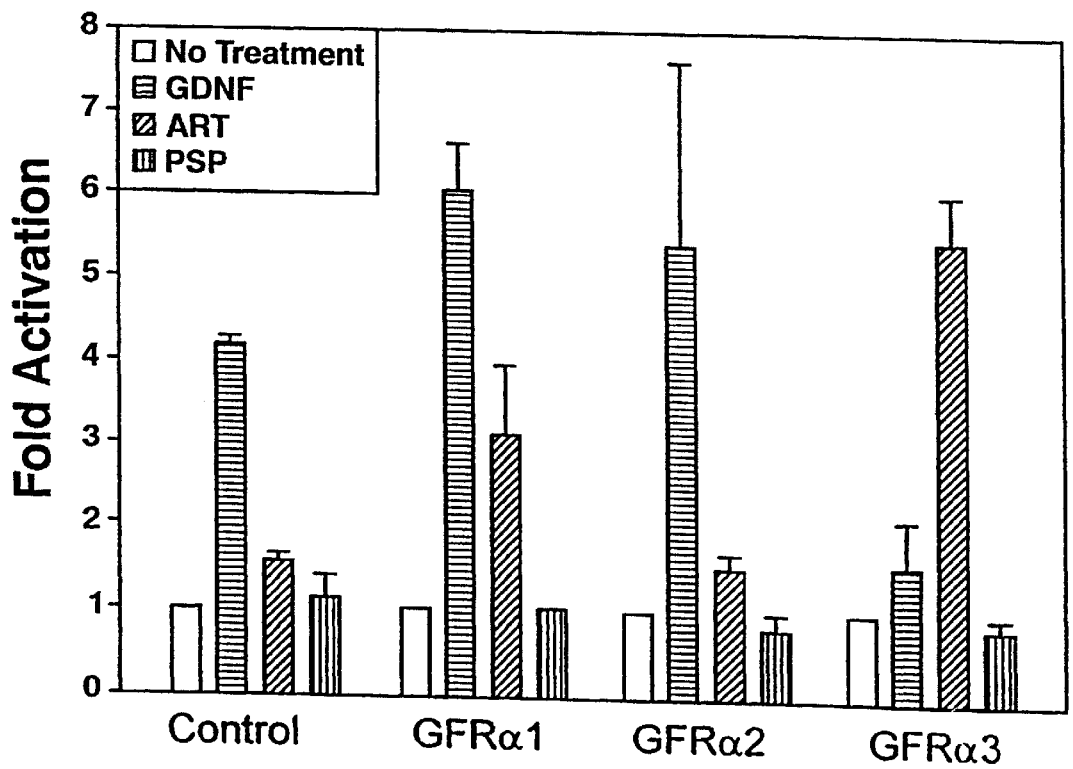

These results were confirmed in the NLF cell line, which is a more neuronal cell line that natively responds to GDNF by RET and MAP kinase activation (unpublished data). As shown in FIG. 10B, NLF cells transformed with GFRα1 responded more intensely to GDNF, and became responsive to artemin, confirming the results observed in fibroblasts. Furthermore, transformation of NLF cells with GFRα3, but not GFRα2, allowed the cells to respond to artemin stimulation. Transformation of NFL cells with GFRα3 also decreased the ability of the cells to respond to GDNF, presumably because CMV-driven overexpression of GFRα3 decreases the relative amount of GFRα2/RET complexes on the cells, thereby decreasing the number of functional GDNF receptors.

In summary, direct binding data and in vitro receptor activation experiments together indicate that artemin is the only known GDNF family ligand for the GFRα3/RET receptor complex, but like GDNF and neurturin it can also activate the GRFα1/RET receptor complex.

EXAMPLE 8

This example illustrates the specificity and cross-talk in interactions of members of the GDNF ligand and GRFα receptor families.

Figure 11:
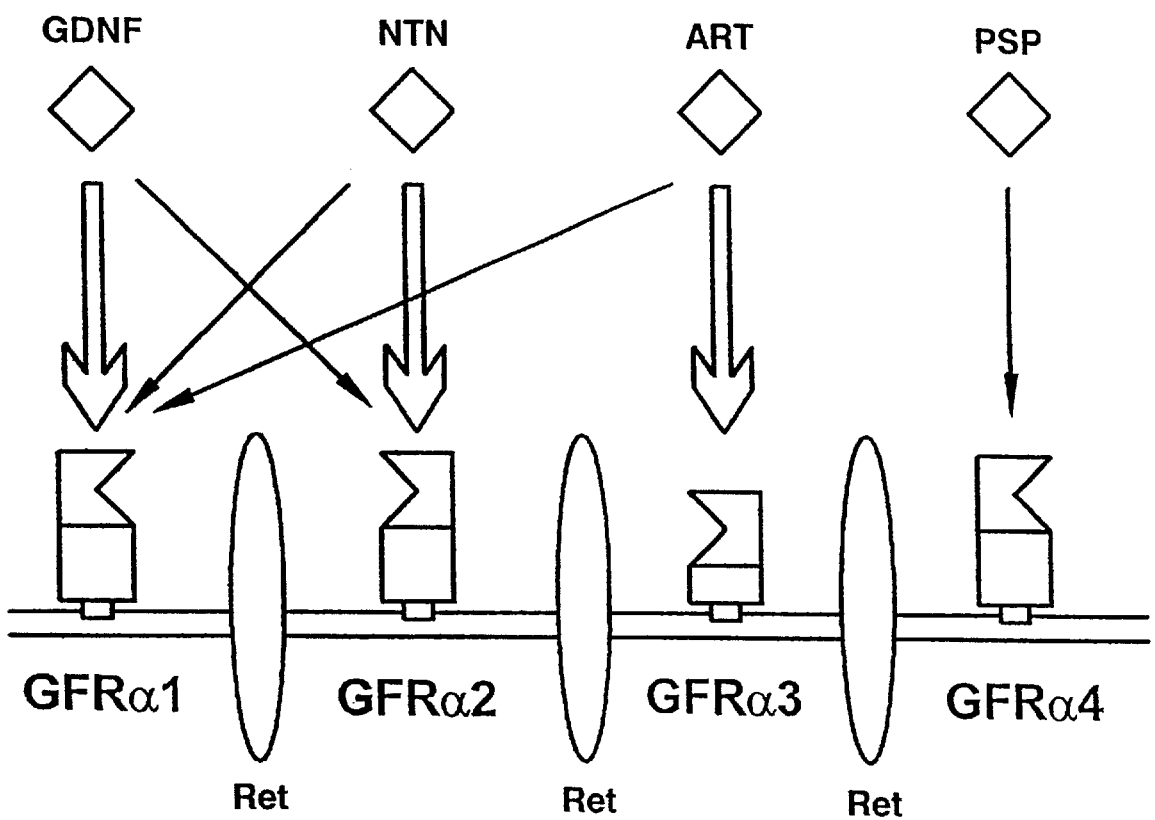
FIG. 11 is a schematic diagram of ligand/receptor interactions in the GDNF ligand family deduced from multiple experimental paradigms in vitro, with large arrows indicating preferred ligand receptor interactions and smaller arrows indicating alternate receptor interactions.

A schematic interaction diagram of the GDNF ligand family members and GRFα receptor family members is presented in FIG. 11. Similar to many other ligand/receptor systems, including the neurotrophins, the system is characterized by having preferred ligand/receptor pairs, however cross-talk between the different ligands and receptors is apparent. The addition of artemin to this diagram reveals several new features. First, both direct receptor binding experiments and receptor activation experiments presented herein indicate that artemin is the only GDNF family ligand capable of utilizing the GFRα3/RET receptor complex. One additional study indicated that GDNF was able bind to GFRα3 in the presence of RET (Trupp et al., 1998), however this interaction was of low-affinity in that it required cross-linking to be observed, and its relevance is unclear because it does not lead to RET activation in multiple experimental paradigms in vitro (Baloh et al., 1998; Trupp et al., 1998; Worby et al., 1998). Second, the GFRα1/RET receptor complex is highly promiscuous, and although results from most in vitro paradigms agree that it is the preferred receptor for GDNF, it is believed that neurturin and artemin also utilize the GFRα1/RET receptor complex in some systems in vivo. Recent observations regarding differences in peripheral neuron losses between GDNF and GRFα1-deficient mice suggest that GDNF can use GFRα2/RET as a receptor in vivo, and confirm that alternative ligand/receptor interactions may have biological importance in the GDNF family (Cacalano et al., 1998; Enomoto et al., 1998). Furthermore, a recent paper analyzing neurotrophin knockout mice concluded that NT-3 can signal through TrkB in vivo, an interaction observed many years earlier in vitro but was thought to be irrelevant in vivo (Farinas I et al., 1998; Ip et al., 1993). Therefore, consideration of all possible ligand/receptor interactions identified in vitro is often necessary to understand results of in vivo analysis of neurotrophic factor influences.

Results from direct binding and RET activation experiments presented herein further suggest that like the GDNF-GFRα2 interaction, the artemin-GFRα1 interaction appears dependent on the presence of RET, as direct binding of artemin to GFRα1-Fc, or GDNF to GFRα2-Fc receptor bodies was not observed (FIG. 9C; Sanicola et al., 1997). This may be due to the nature of the binding assay which utilizes soluble receptor bodies binding to immobilized ligand. However, this may alternatively reflect an additional level of specificity available to the GDNF ligand/GRFα system, in cases where the GFRα coreceptors are expressed in the absence of RET (Baloh et al., 1997; Golden et al., 1998; Trupp et al., 1997; Yu et al., 1998). In these situations (i.e. GFRα1 in injured peripheral nerve, and GFRα2 expression in cerebral cortex), where coreceptors are expressed in "trans" and are hypothesized to secrete or present ligand/coreceptor complexes to cells or axons expressing RET, only the RET-independent subset of binding interactions would be possible.

Deposit of Plasmid:

The following plasmid has been deposited under the terms of the Budapest Treaty, with the American Type Culture Collection, 10801 University Blvd., Manassas, Va. 20110-2209. The accession number indicated was assigned after successful verification of the presence of the plasmid in the deposit, and the requisite fees have been paid. Access to said plasmid will be available during pendency of the patent application to one determined by the Commissioner to be entitled thereto under 37 CFR 1.14 and 35 USC 122. All restriction on availability of said plasmid to the public will be irrevocably removed upon the granting of a patent based upon the application. Moreover, the designated deposits will be maintained for a period of thirty (30) years from the date of deposit, or for five (5) years after the last request for the deposit, or for the enforceable life of the U.S. patent, whichever is longer. Should the plasmid become nonviable or be inadvertently destroyed, it will be replaced with a viable plasmid. The deposited materials mentioned herein are intended for convenience only, and are not required to practice the present invention in view of the description herein, and in addition, these materials are incorporated herein by reference.

| Name of Plasmid | Deposit Date | ATCC No. |
| --- | --- | --- |
| phART | December 22, 1998 | |

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicants reserve the right to challenge the accuracy and pertinency of the cited references.

What is claimed is:

1. A method for providing trophic support to a mammalian neuronal cell, or producing differentiation of the cell, or both, comprising introducing into the cell in vitro a nucleic acid comprising a nucleotide sequence encoding an artemin polypeptide of at least 96 amino acids and which has at least 75% sequence identity with SEQ ID NO: 19, wherein the artemin polypeptide comprises seven canonical framework cysteine residues, is naturally occurring, and is expressed in an amount that is effective to provide trophic support to a mammalian neuronal cell or, produce differentiation of the cell, or both.

2. The method of claim 1, wherein the nucleotide sequence comprises SEQ ID NO:6 or SEQ ID NO:37.

3. The method of claim 1, wherein the artemin polypeptide comprises SEQ ID NO:19 or SEQ ID NO:33.

4. The method of claim 1, wherein the method further comprises treating the cell with a second nucleotide sequence encoding a GFRα3 polypeptide comprising amino acids 32–372 of SEQ ID NO:63 or amino acids 29–369 of SEQ ID NO:64.

5. The method of claim 4, wherein the second nucleotide sequence comprises nucleotides 94–1116 of SEQ ID NO:65.

* * * * *

SEQUENCE LISTING

<160> NUMBER OF SEQ ID NOS: 120

<210> SEQ ID NO 1
<211> LENGTH: 696
<212> TYPE: DNA
<213> ORGANISM: Homo sapiens

<400> SEQUENCE: 1

```
tggccgctct ggctctgctg agcagcgtcg cagaggcctc cctgggctcc gcgccccgca    60
gccctgcccc ccgcgaaggc ccccgcctg tcctggcgtc cccgccggc cacctgccgg     120
gtaggtgaga gggcgagggg gcggggcggg gctggcccgg acaccgcgc gtgactgggt    180
ctcattccag ggggacgcac ggcccgctgg tgcagtggaa gagcccggcg gccgccgccg    240
cagccttctc ggcccgcgcc cccgccgcct gcaccccat ctgctcttcc ccgcgggggc     300
cgcgcggcgc gggctggggg cccgggcagc gcgctcggg cagcggggc gcgggctgc       360
cgcctgcgct cgcagctggt gccggtgcgc gcgctcggcc tgggccaccg ctccgacgag    420
ctggtgcgtt tccgcttctg cagcggctcc tgccgccgcg cgcgctctcc acacgacctc    480
agcctggcca gctactggg cgccggggcc ctgcgaccgc cccgggctc ccggcccgtc      540
agccagccct gctgccgacc cacgcgctac gaagcggtct ccttcatgga cgtcaacagc    600
acctggagaa ccgtggaccg cctctccgcc accgcctgcg gctgcctggg ctgagggctc    660
gctccagggc tttgcagact ggaccttac cggtgg                               696
```

<210> SEQ ID NO 2
<211> LENGTH: 696
<212> TYPE: DNA
<213> ORGANISM: Homo sapiens

<400> SEQUENCE: 2

```
ccaccggtaa gggtccagtc tgcaaagccc tggagcgagc cctcagccca ggcagccgca    60
ggcggtggcg gagaggcggt ccacggttct ccaggtgctg ttgacgtcca tgaaggagac    120
cgcttcgtag cgcgtgggtc ggcagcaggg ctggctgacg ggccgggagc ccgggggcgg    180
tcgcagggcc ccgcgcccca gtaggctggc caggctgagg tcgtgtggag agcgcgcgcg    240
gcggcaggag ccgctgcaga agcggaaacg caccagctcg tcggagcggt ggcccaggcc    300
gagcgcgcgc accggcacca gctgcgagcg caggcggcag cccgcgccc ccgctgcccg     360
agcgcggctg cccgggcccc cagcccgcgc cgcgcggccc ccgcggggaa gagcagatgg    420
gggtgcaggc ggcggggcg cgggccgaga aggctgcggc ggcggccgcc gggctcttcc     480
actgcaccag cgggccgtgc gtccccctgg aatgagaccc agtcacgcgc ggtgtcccgg    540
gccagccccg ccccgccccc tcgccctctc acctacccgg caggtggccg gcggggacg     600
ccaggacagg cgggggggcct tcgcgggggg cagggctgcg gggcgcggag cccagggagg    660
cctctgcgac gctgctcagc agagccagag cggcca                              696
```

<210> SEQ ID NO 3
<211> LENGTH: 113
<212> TYPE: PRT
<213> ORGANISM: Homo sapiens

<400> SEQUENCE: 3

```
Ala Gly Gly Pro Gly Ser Arg Ala Arg Ala Gly Ala Arg Gly Cys
 1               5                  10                  15
```

-continued

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65              70                  75                  80

Cys Arg Pro Thr Arg Tyr Glu Ala Val Ser Phe Met Asp Val Asn Ser
            85                  90                  95

Thr Trp Arg Thr Val Asp Arg Leu Ser Ala Thr Ala Cys Gly Cys Leu
            100                 105                 110

Gly

<210> SEQ ID NO 4
<211> LENGTH: 116
<212> TYPE: PRT
<213> ORGANISM: Homo sapiens

<400> SEQUENCE: 4

Ala Ala Arg Ala Gly Gly Pro Gly Ser Arg Ala Arg Ala Ala Gly Ala
1               5                   10                  15

Arg Gly Cys Arg Leu Arg Ser Gln Leu Val Pro Val Arg Ala Leu Gly
            20                  25                  30

Leu Gly His Arg Ser Asp Glu Leu Val Arg Phe Arg Phe Cys Ser Gly
        35                  40                  45

Ser Cys Arg Arg Ala Arg Ser Pro His Asp Leu Ser Leu Ala Ser Leu
    50                  55                  60

Leu Gly Ala Gly Ala Leu Arg Pro Pro Gly Ser Arg Pro Val Ser
65              70                  75                  80

Gln Pro Cys Cys Arg Pro Thr Arg Tyr Glu Ala Val Ser Phe Met Asp
                85                  90                  95

Val Asn Ser Thr Trp Arg Thr Val Asp Arg Leu Ser Ala Thr Ala Cys
            100                 105                 110

Gly Cys Leu Gly
        115

<210> SEQ ID NO 5
<211> LENGTH: 140
<212> TYPE: PRT
<213> ORGANISM: Homo sapiens

<400> SEQUENCE: 5

Pro Pro Pro Gln Pro Ser Arg Pro Ala Pro Pro Pro Ala Pro Pro
1               5                   10                  15

Ser Ala Leu Pro Arg Gly Gly Arg Ala Ala Arg Ala Gly Gly Pro Gly
            20                  25                  30

Ser Arg Ala Arg Ala Ala Gly Ala Arg Gly Cys Arg Leu Arg Ser Gln
        35                  40                  45

Leu Val Pro Val Arg Ala Leu Gly Leu Gly His Arg Ser Asp Glu Leu
    50                  55                  60

Val Arg Phe Arg Phe Cys Ser Gly Ser Cys Arg Arg Ala Arg Ser Pro
65              70                  75                  80

His Asp Leu Ser Leu Ala Ser Leu Leu Gly Ala Gly Ala Leu Arg Pro
                85                  90                  95

Pro Pro Gly Ser Arg Pro Val Ser Gln Pro Cys Cys Arg Pro Thr Arg

```
              100                 105                 110
Tyr Glu Ala Val Ser Phe Met Asp Val Asn Ser Thr Trp Arg Thr Val
            115                 120                 125
Asp Arg Leu Ser Ala Thr Ala Cys Gly Cys Leu Gly
        130                 135                 140

<210> SEQ ID NO 6
<211> LENGTH: 342
<212> TYPE: DNA
<213> ORGANISM: Homo sapiens

<400> SEQUENCE: 6
gctgggggcc cggcagccg cgctcgggca gcggggggcgc ggggctgccg cctgcgctcg      60
cagctggtgc cggtgcgcgc gctcggcctg gccaccgct ccgacgagct ggtgcgtttc     120
cgcttctgca gcggctcctg ccgccgcgcg cgctctccac acgacctcag cctggccagc     180
ctactgggcg ccggggccct gcgaccgccc cgggctccc ggcccgtcag ccagccctgc     240
tgccgaccca cgcgctacga agcggtctcc ttcatggacg tcaacagcac ctggagaacc     300
gtggaccgcc tctccgccac cgcctgcggc tgcctgggct ga                        342

<210> SEQ ID NO 7
<211> LENGTH: 351
<212> TYPE: DNA
<213> ORGANISM: Homo sapiens

<400> SEQUENCE: 7
gcggcgcggg ctgggggccc gggcagccgc gctcgggcag cggggcgcg gggctgccgc      60 ctgcgctcgc agctggtgcc ggtgcgcgcg ctcggcctgg ccaccgctc cgacgagctg     120 gtgcgtttcc gcttctgcag cggctcctgc cgccgcgcgc gctctccaca cgacctcagc     180
ctggccagcc tactgggcgc cggggccctg cgaccgcccc gggctcccg gcccgtcagc     240 cagccctgct gccgacccac gcgctacgaa gcggtctcct tcatggacgt caacagcacc     300
tggagaaccg tggaccgcct ctccgccacc gcctgcggct gcctgggctg a              351

<210> SEQ ID NO 8
<211> LENGTH: 423
<212> TYPE: DNA
<213> ORGANISM: Homo sapiens

<400> SEQUENCE: 8
ccgccgccgc agccttctcg gcccgcgccc cgccgcctg caccccatc tgctcttccc      60 cgcgggggcc gcgcggcgcg ggctgggggc cgggcagcc gcgctcgggc agcgggggcg     120
cggggctgcc gcctgcgctc gcagctggtg ccggtgcgcg cgctcggcct gggccaccgc     180
tccgacgagc tggtgcgttt ccgcttctgc agcggctcct gccgccgcgc gcgctctcca     240
cacgacctca gcctggccag cctactgggc gccggggccc tgcgaccgcc cccgggctcc     300 ggcccgtca gccagccctg ctgccgaccc acgcgctacg aagcggtctc cttcatggac     360
gtcaacagca cctggagaac cgtggaccgc ctctccgcca ccgcctgcgg ctgcctgggc     420
tga                                                                  423

<210> SEQ ID NO 9
<211> LENGTH: 342
<212> TYPE: DNA
<213> ORGANISM: Homo sapiens

<400> SEQUENCE: 9
```

```
tcagcccagg cagccgcagg cggtggcgga gaggcggtcc acggttctcc aggtgctgtt      60
gacgtccatg aaggagaccg cttcgtagcg cgtgggtcgg cagcagggct ggctgacggg     120
ccgggagccc gggggcggtc gcagggcccc ggcgcccagt aggctggcca ggctgaggtc     180
gtgtggagag cgcgcgcggc ggcaggagcc gctgcagaag cggaaacgca ccagctcgtc     240
ggagcggtgg cccaggccga gcgcgcgcac cggcaccagc tgcgagcgca ggcggcagcc     300
ccgcgccccc gctgcccgag cgcggctgcc cgggccccca gc                        342
```

<210> SEQ ID NO 10
<211> LENGTH: 351
<212> TYPE: DNA
<213> ORGANISM: Homo sapiens

<400> SEQUENCE: 10

```
tcagcccagg cagccgcagg cggtggcgga gaggcggtcc acggttctcc aggtgctgtt      60
gacgtccatg aaggagaccg cttcgtagcg cgtgggtcgg cagcagggct ggctgacggg     120
ccgggagccc gggggcggtc gcagggcccc ggcgcccagt aggctggcca ggctgaggtc     180
gtgtggagag cgcgcgcggc ggcaggagcc gctgcagaag cggaaacgca ccagctcgtc     240
ggagcggtgg cccaggccga gcgcgcgcac cggcaccagc tgcgagcgca ggcggcagcc     300
ccgcgccccc gctgcccgag cgcggctgcc cgggccccca gcccgcgccg c              351
```

<210> SEQ ID NO 11
<211> LENGTH: 423
<212> TYPE: DNA
<213> ORGANISM: Homo sapiens

<400> SEQUENCE: 11

```
tcagcccagg cagccgcagg cggtggcgga gaggcggtcc acggttctcc aggtgctgtt      60
gacgtccatg aaggagaccg cttcgtagcg cgtgggtcgg cagcagggct ggctgacggg     120
ccgggagccc gggggcggtc gcagggcccc ggcgcccagt aggctggcca ggctgaggtc     180
gtgtggagag cgcgcgcggc ggcaggagcc gctgcagaag cggaaacgca ccagctcgtc     240
ggagcggtgg cccaggccga gcgcgcgcac cggcaccagc tgcgagcgca ggcggcagcc     300
ccgcgccccc gctgcccgag cgcggctgcc cgggccccca gcccgcgccg cgcggccccc     360
gcggggaaga gcagatgggg gtgcaggcgg cggggcgcg gccgagaag ctgcggcgg        420 cgg                                                                   423
```

<210> SEQ ID NO 12
<211> LENGTH: 159
<212> TYPE: PRT
<213> ORGANISM: Homo sapiens

<400> SEQUENCE: 12

```
Leu Gly Leu Ile Pro Gly Gly Arg Thr Ala Arg Trp Cys Ser Gly Arg
  1               5                  10                  15

Ala Arg Arg Pro Pro Gln Pro Ser Arg Pro Ala Pro Pro Pro
             20                  25                  30

Ala Pro Pro Ser Ala Leu Pro Arg Gly Gly Arg Ala Ala Arg Ala Gly
         35                  40                  45

Gly Pro Gly Ser Arg Ala Arg Ala Ala Gly Ala Arg Gly Cys Arg Leu
     50                  55                  60

Arg Ser Gln Leu Val Pro Val Arg Ala Leu Gly Leu Gly His Arg Ser
 65                  70                  75                  80
```

```
Asp Glu Leu Val Arg Phe Arg Phe Cys Ser Gly Ser Cys Arg Arg Ala
                85                  90                  95

Arg Ser Pro His Asp Leu Ser Leu Ala Ser Leu Leu Gly Ala Gly Ala
            100                 105                 110

Leu Arg Pro Pro Pro Gly Ser Arg Pro Val Ser Gln Pro Cys Cys Arg
        115                 120                 125

Pro Thr Arg Tyr Glu Ala Val Ser Phe Met Asp Val Asn Ser Thr Trp
130                 135                 140

Arg Thr Val Asp Arg Leu Ser Ala Thr Ala Cys Gly Cys Leu Gly
145                 150                 155
```

```
<210> SEQ ID NO 13
<211> LENGTH: 134
<212> TYPE: PRT
<213> ORGANISM: Homo sapiens

<400> SEQUENCE: 13

Ser Pro Asp Lys Gln Met Ala Val Leu Pro Arg Arg Glu Arg Asn Arg
 1               5                  10                  15

Gln Ala Ala Ala Asn Pro Glu Asn Ser Arg Gly Lys Gly Arg Arg
             20                  25                  30

Gly Gln Arg Gly Lys Asn Arg Gly Cys Val Leu Thr Ala Ile His Leu
         35                  40                  45

Asn Val Thr Asp Leu Gly Leu Gly Tyr Glu Thr Lys Glu Glu Leu Ile
 50                  55                  60

Phe Arg Tyr Cys Ser Gly Ser Cys Asp Ala Ala Glu Thr Thr Tyr Asp
 65                  70                  75                  80

Lys Ile Leu Lys Asn Leu Ser Arg Asn Arg Arg Leu Val Ser Asp Lys
                 85                  90                  95

Val Gly Gln Ala Cys Cys Arg Pro Ile Ala Phe Asp Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
130
```

```
<210> SEQ ID NO 14
<211> LENGTH: 102
<212> TYPE: PRT
<213> ORGANISM: Homo sapiens

<400> SEQUENCE: 14

Ala Arg Leu Gly Ala Arg Pro Cys Gly Leu Arg Glu Leu Glu Val Arg
 1               5                  10                  15

Val Ser Glu Leu Gly Leu Gly Tyr Ala Ser Asp Glu Thr Val Leu Phe
             20                  25                  30

Arg Tyr Cys Ala Gly Ala Cys Glu Ala Ala Ala Arg Val Tyr Asp Leu
         35                  40                  45

Gly Leu Arg Arg Leu Arg Gln Arg Arg Arg Leu Arg Arg Glu Arg Val
     50                  55                  60

Arg Ala Gln Pro Cys Cys Arg Pro Thr Ala Tyr Glu Asp Glu Val Ser
 65                  70                  75                  80

Phe Leu Asp Ala His Ser Arg Tyr His Thr Val His Glu Leu Ser Ala
                 85                  90                  95

Arg Glu Cys Ala Cys Val
            100
```

```
<210> SEQ ID NO 15
<211> LENGTH: 96
<212> TYPE: PRT
<213> ORGANISM: Homo sapiens

<400> SEQUENCE: 15
```

Ala Leu Ser Gly Pro Cys Gln Leu Trp Ser Leu Thr Leu Ser Val Ala
 1               5                  10                  15

Glu Leu Gly Leu Gly Tyr Ala Ser Glu Lys Val Ile Phe Arg Tyr
            20                  25                  30

Cys Ala Gly Ser Cys Pro Arg Gly Ala Arg Thr Gln His Gly Leu Ala
            35                  40                  45

Leu Ala Arg Leu Gln Gly Gln Gly Arg Ala His Gly Gly Pro Cys Cys
        50                  55                  60

Arg Pro Thr Arg Tyr Thr Asp Val Ala Phe Leu Asp Asp Arg His Arg
 65                  70                  75                  80

Trp Gln Arg Leu Pro Gln Leu Ser Ala Ala Cys Gly Cys Gly Gly
                85                  90                  95

```
<210> SEQ ID NO 16
<211> LENGTH: 93
<212> TYPE: PRT
<213> ORGANISM: Homo sapiens

<400> SEQUENCE: 16
```

Cys Val Leu Thr Ala Ile His Leu Asn Val Thr Asp Leu Gly Leu Gly
 1               5                  10                  15

Tyr Glu Thr Lys Glu Glu Leu Ile Phe Arg Tyr Cys Ser Gly Ser Cys
            20                  25                  30

Asp Ala Ala Glu Thr Thr Tyr Asp Lys Ile Leu Lys Asn Leu Ser Arg
        35                  40                  45

Asn Arg Arg Leu Val Ser Asp Lys Val Gly Gln Ala Cys Cys Arg Pro
    50                  55                  60

Ile Ala Phe Asp Asp Asp Leu Ser Phe Leu Asp Asp Asn Leu Val Tyr
 65                  70                  75                  80

His Ile Leu Arg Lys His Ser Ala Lys Arg Cys Gly Cys
                85                  90

```
<210> SEQ ID NO 17
<211> LENGTH: 94
<212> TYPE: PRT
<213> ORGANISM: Homo sapiens

<400> SEQUENCE: 17
```

Cys Gly Leu Arg Glu Leu Glu Val Arg Val Ser Glu Leu Gly Leu Gly
 1               5                  10                  15

Tyr Ala Ser Asp Glu Thr Val Leu Phe Arg Tyr Cys Ala Gly Ala Cys
            20                  25                  30

Glu Ala Ala Ala Arg Val Tyr Asp Leu Gly Leu Arg Arg Leu Arg Gln
        35                  40                  45

Arg Arg Arg Leu Arg Arg Glu Arg Val Arg Ala Gln Pro Cys Cys Arg
    50                  55                  60

Pro Thr Ala Tyr Glu Asp Glu Val Ser Phe Leu Asp Ala His Ser Arg
 65                  70                  75                  80

Tyr His Thr Val His Glu Leu Ser Ala Arg Glu Cys Ala Cys
                85                  90

```
<210> SEQ ID NO 18
<211> LENGTH: 89
<212> TYPE: PRT
<213> ORGANISM: Homo sapiens

<400> SEQUENCE: 18

Cys Gln Leu Trp Ser Leu Thr Leu Ser Val Ala Glu Leu Gly Leu Gly
 1               5                  10                  15

Tyr Ala Ser Glu Glu Lys Val Ile Phe Arg Tyr Cys Ala Gly Ser Cys
            20                  25                  30

Pro Arg Gly Ala Arg Thr Gln His Gly Leu Ala Leu Ala Arg Leu Gln
        35                  40                  45

Gly Gln Gly Arg Ala His Gly Gly Pro Cys Cys Arg Pro Thr Arg Tyr
    50                  55                  60

Thr Asp Val Ala Phe Leu Asp Asp Arg His Arg Trp Gln Arg Leu Pro
65                  70                  75                  80

Gln Leu Ser Ala Ala Ala Cys Gly Cys
                85

<210> SEQ ID NO 19
<211> LENGTH: 96
<212> TYPE: PRT
<213> ORGANISM: Homo sapiens

<400> SEQUENCE: 19

Cys Arg Leu Arg Ser Gln Leu Val Pro Val Arg Ala Leu Gly Leu Gly
 1               5                  10                  15

His Arg Ser Asp Glu Leu Val Arg Phe Arg Phe Cys Ser Gly Ser Cys
            20                  25                  30

Arg Arg Ala Arg Ser Pro His Asp Leu Ser Leu Ala Ser Leu Leu Gly
        35                  40                  45

Ala Gly Ala Leu Arg Pro Pro Pro Gly Ser Arg Pro Val Ser Gln Pro
    50                  55                  60

Cys Cys Arg Pro Thr Arg Tyr Glu Ala Val Ser Phe Met Asp Val Asn
65                  70                  75                  80

Ser Thr Trp Arg Thr Val Asp Arg Leu Ser Ala Thr Ala Cys Gly Cys
                85                  90                  95

<210> SEQ ID NO 20
<211> LENGTH: 24
<212> TYPE: DNA
<213> ORGANISM: Homo sapiens

<400> SEQUENCE: 20
tggccgctct ggctctgctg agca                                        24

<210> SEQ ID NO 21
<211> LENGTH: 37
<212> TYPE: DNA
<213> ORGANISM: Homo sapiens

<400> SEQUENCE: 21
cgatcatcta gaccaccggt aagggtccag tctgcaa                          37

<210> SEQ ID NO 22
<211> LENGTH: 54
<212> TYPE: DNA
<213> ORGANISM: Homo sapiens

<400> SEQUENCE: 22
```

<210> SEQ ID NO 23
<211> LENGTH: 37
<212> TYPE: DNA
<213> ORGANISM: Homo sapiens

<400> SEQUENCE: 23

```
cgatcatcta gaccaccggt aagggtccag tctgcaa                        37
```

<210> SEQ ID NO 24
<211> LENGTH: 663
<212> TYPE: DNA
<213> ORGANISM: Homo sapiens

<400> SEQUENCE: 24

```
atggaacttg gacttggagg cctctccacg ctgtcccact gccctggcc taggcggcag    60
cctgccctgt ggcccaccct ggccgctctg gctctgctga gcagcgtcgc agaggcctcc  120
ctgggctccg cgccccgcag ccctgccccc cgcgaaggcc cccgcctgt cctgcgtcc   180
cccgccggcc acctgccggg gggacgcacg gcccgctggt gcagtggaag agcccggcgg  240
ccgccgccgc agccttctcg gcccgcgccc cgccgcctg caccccatc tgctcttccc   300
cgcgggggcc gcgcggcgcg ggctgggggc ccgggcagcc gcgctcgggc agcgggggcg  360
cggggctgcc gcctgcgctc gcagctgtg ccggtgcgcg cgctcggcct gggccaccgc   420
tccgacgagc tggtgcgttt ccgcttctgc agcggctcct gccgccgcgc gcgctctcca  480
cacgacctca gcctggccag cctactgggc gccggggccc tgcgaccgcc cccgggctcc  540
cggcccgtca gccagccctg ctgccgaccc acgcgctacg aagcggtctc cttcatggac  600
gtcaacagca cctggagaac cgtggaccgc ctctccgcca ccgcctgcgg ctgcctgggc  660
tga                                                               663
```

<210> SEQ ID NO 25
<211> LENGTH: 663
<212> TYPE: DNA
<213> ORGANISM: Homo sapiens

<400> SEQUENCE: 25

```
tcagcccagg cagccgcagg cggtggcgga gaggcggtcc acggttctcc aggtgctgtt    60
gacgtccatg aaggagaccg cttcgtagcg cgtgggtcgg cagcagggct ggctgacggg   120
ccgggagccc gggggcggtc gcagggcccc ggcgcccagt aggctggcca ggctgaggtc   180
gtgtggagag cgcgcgcggc ggcaggagcc gctgcagaag cggaaacgca ccagctcgtc   240
ggagcggtgg cccaggccga gcgcgcgcac cggcaccagc tgcgagcgca ggcggcagcc   300
ccgcgccccc gctgcccgag gcggctgccc gggccccca gccgcgccg cgcggccccc    360
gcggggaaga gcagatgggg gtgcaggcgg cggggcgcg ggccgagaag gctgcggcgg   420
cggccgccgg gctcttccac tgcaccagcg ggccgtgcgt cccccggca ggtggccggc   480
gggggacgcc aggacaggcg ggggccttc gcggggggca gggctgcggg gcgcggagcc   540
cagggaggcc tctgcgacgc tgctcagcag agccagagcg gccagggtgg gccacagggc   600
aggctgccgc ctaggccagg ggcagtggga cagcgtggag aggcctccaa gtccaagttc   660
cat                                                               663
```

<210> SEQ ID NO 26

<211> LENGTH: 220
<212> TYPE: PRT
<213> ORGANISM: Homo sapiens

<400> SEQUENCE: 26

```
Met Glu Leu Gly Leu Gly Gly Leu Ser Thr Leu Ser His Cys Pro Trp
 1               5                  10                  15
Pro Arg Arg Gln Pro Ala Leu Trp Pro Thr Leu Ala Ala Leu Ala Leu
             20                  25                  30
Leu Ser Ser Val Ala Glu Ala Ser Leu Gly Ser Ala Pro Arg Ser Pro
         35                  40                  45
Ala Pro Arg Glu Gly Pro Pro Val Leu Ala Ser Pro Ala Gly His
     50                  55                  60
Leu Pro Gly Gly Arg Thr Ala Arg Trp Cys Ser Gly Arg Ala Arg Arg
 65                  70                  75                  80
Pro Pro Pro Gln Pro Ser Arg Pro Ala Pro Pro Pro Ala Pro Pro
                 85                  90                  95
Ser Ala Leu Pro Arg Gly Gly Arg Ala Ala Arg Ala Gly Gly Pro Gly
                100                 105                 110
Ser Arg Ala Arg Ala Ala Gly Ala Arg Gly Cys Arg Leu Arg Ser Gln
            115                 120                 125
Leu Val Pro Val Arg Ala Leu Gly Leu Gly His Arg Ser Asp Glu Leu
        130                 135                 140
Val Arg Phe Arg Phe Cys Ser Gly Ser Cys Arg Arg Ala Arg Ser Pro
145                 150                 155                 160
His Asp Leu Ser Leu Ala Ser Leu Leu Gly Ala Gly Ala Leu Arg Pro
                165                 170                 175
Pro Pro Gly Ser Arg Pro Val Ser Gln Pro Cys Cys Arg Pro Thr Arg
            180                 185                 190
Tyr Glu Ala Val Ser Phe Met Asp Val Asn Ser Thr Trp Arg Thr Val
        195                 200                 205
Asp Arg Leu Ser Ala Thr Ala Cys Gly Cys Leu Gly
    210                 215                 220
```

<210> SEQ ID NO 27
<211> LENGTH: 675
<212> TYPE: DNA
<213> ORGANISM: MURINE

<400> SEQUENCE: 27

| | | |
|---|---|---|
| atggaactgg gacttgcaga gcctactgca ttgtcccact gcctccggcc taggtggcag | 60 |
| tcagcctggt ggccaaccct agctgttcta gccctgctga gctgcgtcac agaagcttcc | 120 |
| ctggacccaa tgtcccgcag ccccgccgct cgcgacggtc cctcaccggt cttggcgccc | 180 |
| cccacggacc acctgcctgg gggacacact gcgcatttgt gcagcgaaag aaccctgcga | 240 |
| cccccgcctc agtctcctca gcccgcaccc cgccgcctg gtcccgcgct ccagtctcct | 300 |
| cccgctgcgc tccgcggggc acgcgcggcg cgtgcaggaa cccggagcag ccgcgcacgg | 360 |
| accacagatg cgcgcggctg ccgcctgcgc tcgcagctgg tgccggtgag tgcgctcggc | 420 |
| ctaggccaca gctccgacga gctgatacgt ttccgcttct gcagcggctc gtgccgccga | 480 |
| gcacgctccc agcacgatct cagtctggcc agcctactgg gcgctggggc cctacggtcg | 540 |
| cctcccgggt ccggccgat cagccagccc tgctgccggc ccactcgcta tgaggccgtc | 600 |
| tccttcatgg acgtgaacag cacctggagg accgtggacc acctctccgc cactgcctgc | 660 |
| ggctgtctgg gctga | 675 |

```
<210> SEQ ID NO 28
<211> LENGTH: 675
<212> TYPE: DNA
<213> ORGANISM: MURINE

<400> SEQUENCE: 28
tcagcccaga cagccgcagg cagtggcgga gaggtggtcc acggtcctcc aggtgctgtt      60
cacgtccatg aaggagacgg cctcatagcg agtgggccgg cagcagggct ggctgatcgg     120
ccgggacccg ggaggcgacc gtagggcccc agcgcccagt aggctggcca gactgagatc     180
gtgctgggag cgtgctcggc ggcacgagcc gctgcagaag cggaaacgta tcagctcgtc     240
ggagctgtgg cctaggccga gcgcactcac cggcaccagc tgcagcgca ggcggcagcc     300 gcgcgcatct gtggtccgtg cgcggctgct ccgggttcct gcacgcgccg cgcgtgcccc     360
gcggagcgca gcgggaggag actggagcgc gggaccaggc ggcggggtg cgggctgagg      420 agactgaggc gggggtcgca gggttctttc gctgcacaaa tgcgcagtgt gtcccccagg     480
caggtggtcc gtggggggcg ccaagaccgg tgagggaccg tcgcgagcgg cggggctgcg     540
ggacattggg tccagggaag cttctgtgac gcagctcagc agggctagaa cagctagggt     600
tggccaccag gctgactgcc acctaggccg gaggcagtgg acaatgcag taggctctgc      660 aagtcccagt tccat                                                      675

<210> SEQ ID NO 29
<211> LENGTH: 224
<212> TYPE: PRT
<213> ORGANISM: MURINE

<400> SEQUENCE: 29

Met Glu Leu Gly Leu Ala Glu Pro Thr Ala Leu Ser His Cys Leu Arg
  1               5                  10                  15

Pro Arg Trp Gln Ser Ala Trp Trp Pro Thr Leu Ala Val Leu Ala Leu
                 20                  25                  30

Leu Ser Cys Val Thr Glu Ala Ser Leu Asp Pro Met Ser Arg Ser Pro
             35                  40                  45

Ala Ala Arg Asp Gly Pro Ser Pro Val Leu Ala Pro Thr Asp His
         50                  55                  60

Leu Pro Gly Gly His Thr Ala His Leu Cys Ser Glu Arg Thr Leu Arg
 65                  70                  75                  80

Pro Pro Pro Gln Ser Pro Gln Pro Ala Pro Pro Pro Gly Pro Ala
                 85                  90                  95

Leu Gln Ser Pro Pro Ala Ala Leu Arg Gly Ala Arg Ala Ala Arg Ala
                100                 105                 110

Gly Thr Arg Ser Ser Arg Ala Arg Thr Thr Asp Ala Arg Gly Cys Arg
            115                 120                 125

Leu Arg Ser Gln Leu Val Pro Val Ser Ala Leu Gly Leu Gly His Ser
        130                 135                 140

Ser Asp Glu Leu Ile Arg Phe Arg Phe Cys Ser Gly Ser Cys Arg Arg
145                 150                 155                 160

Ala Arg Ser Gln His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
        195                 200                 205
```

Trp Arg Thr Val Asp His Leu Ser Ala Thr Ala Cys Gly Cys Leu Gly
    210                 215                 220

<210> SEQ ID NO 30
<211> LENGTH: 714
<212> TYPE: DNA
<213> ORGANISM: Homo sapiens

<400> SEQUENCE: 30

```
atgcccggcc tgatctcagc ccgaggacag cccctccttg aggtccttcc tccccaagcc    60
cacctgggtg ccctctttct ccctgaggct ccacttggtc tctccgcgca gcctgccctg   120
tggcccaccc tggccgctct ggctctgctg agcagcgtcg cagaggcctc cctgggctcc   180
gcgcccgca gcctgcccc ccgcgaaggc ccccgcctg tcctggcgtc cccgccggc       240
cacctgccgg gggacgcac ggcccgctgg tgcagtggaa gagcccggcg ccgccgccg     300
cagccttctc ggcccgcgcc cccgccgcct gcaccccat ctgctcttcc ccgcggggc    360
cgcgcggcgc gggctggggg ccgggcagc gcgctcggg cagcggggc gcggggctgc     420
cgcctgcgct cgcagctggt gccggtgcgc gcgctcggcc tgggccaccg ctccgacgag   480
ctggtgcgtt ccgcttctg cagcggctcc tgccgccgcg cgcgctctcc acacgacctc   540
agcctggcca gcctactggg cgccggggcc ctgcgaccgc cccggggctc ccggcccgtc  600
agccagccct gctgccgacc cacgcgctac gaagcggtct ccttcatgga cgtcaacagc  660
acctggagaa ccgtggaccg cctctccgcc accgcctgcg gctgcctggg ctga         714
```

<210> SEQ ID NO 31
<211> LENGTH: 714
<212> TYPE: DNA
<213> ORGANISM: Homo sapiens

<400> SEQUENCE: 31

```
tcagcccagg cagccgcagg cggtggcgga gaggcggtcc acggttctcc aggtgctgtt    60
gacgtccatg aaggagaccg cttcgtagcg cgtgggtcgg cagcagggct ggctgacggg   120
ccgggagccc gggggcggtc gcagggcccc ggcgcccagt aggctggcca ggctgaggtc   180
gtgtggagag cgcgcgcggc ggcaggagcc gctgcagaag cggaaacgca ccagctcgtc   240
ggagcggtgg cccaggccga gcgcgcgcac cggcaccagc tgcgagcgca ggcggcagcc  300
ccgcgccccc gctgcccgag gcgggctgcc cgggccccca gccgcgccg cgcggccccc    360
gcggggaaga gcagatgggg gtgcaggcgg cggggcgcg ggccgagaag ctgcggcgg    420
cggccgccgg gctcttccac tgcaccagcg ggccgtgcgt cccccggca ggtggccggc    480
gggggacgcc aggacaggcg ggggccttc gcgggggca gggctgcggg gcgcggagcc    540
cagggaggcc tctgcgacgc tgctcagcag agccagagcg gccagggtgg ccacagggc   600
aggctgcgcg gagagaccaa gtggagcctc agggagaaag agggcaccca ggtgggcttg  660
gggaggaagg acctcaagga ggggctgtcc tcgggctgag atcaggccgg gcat         714
```

<210> SEQ ID NO 32
<211> LENGTH: 237
<212> TYPE: PRT
<213> ORGANISM: Homo sapiens

<400> SEQUENCE: 32

Met Pro Gly Leu Ile Ser Ala Arg Gly Gln Pro Leu Leu Glu Val Leu
  1               5                  10                  15

```
Pro Pro Gln Ala His Leu Gly Ala Leu Phe Leu Pro Glu Ala Pro Leu
            20                  25                  30

Gly Leu Ser Ala Gln Pro Ala Leu Trp Pro Thr Leu Ala Ala Leu Ala
        35                  40                  45

Leu Leu Ser Ser Val Ala Glu Ala Ser Leu Gly Ser Ala Pro Arg Ser
    50                  55                  60

Pro Ala Pro Arg Glu Gly Pro Pro Val Leu Ala Ser Pro Ala Gly
65                  70                  75                  80

His Leu Pro Gly Gly Arg Thr Ala Arg Trp Cys Ser Gly Arg Ala Arg
                85                  90                  95

Arg Pro Pro Pro Gln Pro Ser Arg Pro Ala Pro Pro Pro Pro Ala Pro
                100                 105                 110

Pro Ser Ala Leu Pro Arg Gly Arg Ala Ala Arg Ala Gly Gly Pro
            115                 120                 125

Gly Ser Arg Ala Arg Ala Ala Gly Ala Arg Gly Cys Arg Leu Arg Ser
    130                 135                 140

Gln Leu Val Pro Val Arg Ala Leu Gly Leu Gly His Arg Ser Asp Glu
145                 150                 155                 160

Leu Val Arg Phe Arg Phe Cys Ser Gly Ser Cys Arg Arg Ala Arg Ser
                165                 170                 175

Pro His Asp Leu Ser Leu Ala Ser Leu Leu Gly Ala Gly Ala Leu Arg
            180                 185                 190

Pro Pro Pro Gly Ser Arg Pro Val Ser Gln Pro Cys Cys Arg Pro Thr
            195                 200                 205

Arg Tyr Glu Ala Val Ser Phe Met Asp Val Asn Ser Thr Trp Arg Thr
210                 215                 220

Val Asp Arg Leu Ser Ala Thr Ala Cys Gly Cys Leu Gly
225                 230                 235

<210> SEQ ID NO 33
<211> LENGTH: 96
<212> TYPE: PRT
<213> ORGANISM: MURINE

<400> SEQUENCE: 33

Cys Arg Leu Arg Ser Gln Leu Val Pro Val Ala Leu Gly Leu Gly
  1               5                  10                  15

His Ser Ser Asp Glu Leu Ile Arg Phe Arg Phe Cys Ser Gly Ser Cys
                20                  25                  30

Arg Arg Ala Arg Ser Gln His Asp Leu Ser Leu Ala Ser Leu Leu Gly
            35                  40                  45

Ala Gly Ala Leu Arg Ser Pro Gly Ser Arg Pro Ile Ser Gln Pro
    50                  55                  60

Cys Cys Arg Pro Thr Arg Tyr Glu Ala Val Ser Phe Met Asp Val Asn
65                  70                  75                  80

Ser Thr Trp Arg Thr Val Asp His Leu Ser Ala Thr Ala Cys Gly Cys
                85                  90                  95

<210> SEQ ID NO 34
<211> LENGTH: 113
<212> TYPE: PRT
<213> ORGANISM: MURINE

<400> SEQUENCE: 34

Ala Gly Thr Arg Ser Ser Arg Ala Arg Thr Thr Asp Ala Arg Gly Cys
  1               5                  10                  15
```

-continued

```
Arg Leu Arg Ser Gln Leu Val Pro Val Ser Ala Leu Gly Leu Gly His
             20                  25                  30

Ser Ser Asp Glu Leu Ile Arg Phe Arg Phe Cys Ser Gly Ser Cys Arg
         35                  40                  45

Arg Ala Arg Ser Gln His Asp Leu Ser Leu Ala Ser Leu Leu Gly Ala
     50                  55                  60

Gly Ala Leu Arg Ser Pro Pro Gly Ser Arg Pro Ile Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp His Leu Ser Ala Thr Ala Cys Gly Cys Leu
             100                 105                 110

Gly
```

<210> SEQ ID NO 35
<211> LENGTH: 116
<212> TYPE: PRT
<213> ORGANISM: MURINE

<400> SEQUENCE: 35

```
Ala Ala Arg Ala Gly Thr Arg Ser Ser Arg Ala Arg Thr Thr Asp Ala
 1               5                  10                  15

Arg Gly Cys Arg Leu Arg Ser Gln Leu Val Pro Val Ser Ala Leu Gly
             20                  25                  30

Leu Gly His Ser Ser Asp Glu Leu Ile Arg Phe Arg Phe Cys Ser Gly
         35                  40                  45

Ser Cys Arg Arg Ala Arg Ser Gln His Asp Leu Ser Leu Ala Ser Leu
     50                  55                  60

Leu Gly Ala Gly Ala Leu Arg Ser Pro Pro Gly Ser Arg Pro Ile Ser
 65                  70                  75                  80

Gln Pro Cys Cys Arg Pro Thr Arg Tyr Glu Ala Val Ser Phe Met Asp
                 85                  90                  95

Val Asn Ser Thr Trp Arg Thr Val Asp His Leu Ser Ala Thr Ala Cys
             100                 105                 110

Gly Cys Leu Gly
         115
```

<210> SEQ ID NO 36
<211> LENGTH: 144
<212> TYPE: PRT
<213> ORGANISM: MURINE

<400> SEQUENCE: 36

```
Pro Pro Pro Gln Ser Pro Gln Pro Ala Pro Pro Pro Gly Pro Ala
 1               5                  10                  15

Leu Gln Ser Pro Pro Ala Ala Leu Arg Gly Ala Arg Ala Ala Arg Ala
             20                  25                  30

Gly Thr Arg Ser Ser Arg Ala Arg Thr Thr Asp Ala Arg Gly Cys Arg
         35                  40                  45

Leu Arg Ser Gln Leu Val Pro Val Ser Ala Leu Gly Leu Gly His Ser
     50                  55                  60

Ser Asp Glu Leu Ile Arg Phe Arg Phe Cys Ser Gly Ser Cys Arg Arg
 65                  70                  75                  80

Ala Arg Ser Gln His Asp Leu Ser Leu Ala Ser Leu Leu Gly Ala Gly
                 85                  90                  95

Ala Leu Arg Ser Pro Pro Gly Ser Arg Pro Ile Ser Gln Pro Cys Cys
```

```
           100                 105                 110
Arg Pro Thr Arg Tyr Glu Ala Val Ser Phe Met Asp Val Asn Ser Thr
        115                 120                 125

Trp Arg Thr Val Asp His Leu Ser Ala Thr Ala Cys Gly Cys Leu Gly
    130                 135                 140
```

<210> SEQ ID NO 37
<211> LENGTH: 342
<212> TYPE: DNA
<213> ORGANISM: MURINE

<400> SEQUENCE: 37

```
gcaggaaccc ggagcagccg cgcacggacc acagatgcgc gcggctgccg cctgcgctcg    60
cagctggtgc cggtgagtgc gctcggccta ggccacagct ccgacgagct gatacgtttc   120
cgcttctgca gcggctcgtg ccgccgagca cgctcccagc acgatctcag tctggccagc   180
ctactgggcg ctggggccct acggtcgcct cccgggtccc ggccgatcag ccagccctgc   240
tgccggccca ctcgctatga ggccgtctcc ttcatggacg tgaacagcac ctggaggacc   300
gtggaccacc tctccgccac tgcctgcggc tgtctgggct ga                       342
```

<210> SEQ ID NO 38
<211> LENGTH: 351
<212> TYPE: DNA
<213> ORGANISM: MURINE

<400> SEQUENCE: 38

```
gcggcgcgtg caggaacccg gagcagccgc gcacggacca cagatgcgcg cggctgccgc    60
ctgcgctcgc agctggtgcc ggtgagtgcg ctcggcctag gccacagctc cgacgagctg   120
atacgtttcc gcttctgcag cggctcgtgc cgccgagcac gctcccagca cgatctcagt   180
ctggccagcc tactgggcgc tggggcccta cggtcgcctc ccgggtcccg gccgatcagc   240
cagccctgct gccggcccac tcgctatgag gccgtctcct tcatggacgt gaacagcacc   300
tggaggaccg tggaccacct ctccgccact gcctgcggct gtctgggctg a             351
```

<210> SEQ ID NO 39
<211> LENGTH: 435
<212> TYPE: DNA
<213> ORGANISM: MURINE

<400> SEQUENCE: 39

```
cccccgcctc agtctcctca gcccgcaccc ccgccgcctg gtcccgcgct ccagtctcct    60
cccgctgcgc tccgcggggc acgcgcggcg cgtgcaggaa cccggagcag ccgcgcacgg   120
accacagatg cgcgcggctg ccgcctgcgc tcgcagctgg tgccggtgag tgcgctcggc   180
ctaggccaca gctccgacga gctgatacgt ttccgcttct gcagcggctc gtgccgccga   240
gcacgctccc agcacgatct cagtctggcc agcctactgg gcgctgggc cctacggtcg   300
cctcccgggt cccggccgat cagccagccc tgctgccggc ccactcgcta tgaggccgtc   360
tccttcatgg acgtgaacag cacctggagg accgtggacc acctctccgc cactgcctgc   420
ggctgtctgg gctga                                                     435
```

<210> SEQ ID NO 40
<211> LENGTH: 181
<212> TYPE: PRT
<213> ORGANISM: Homo sapiens

<400> SEQUENCE: 40

```
Ser Leu Gly Ser Ala Pro Arg Ser Pro Ala Pro Arg Glu Gly Pro Pro
 1               5                  10                  15

Pro Val Leu Ala Ser Pro Ala Gly His Leu Pro Gly Gly Arg Thr Ala
                20                  25                  30

Arg Trp Cys Ser Gly Arg Ala Arg Pro Pro Gln Pro Ser Arg
        35                  40                  45

Pro Ala Pro Pro Pro Ala Pro Ser Ala Leu Pro Arg Gly Gly
    50                  55                  60

Arg Ala Ala Arg Ala Gly Gly Pro Gly Ser Arg Ala Arg Ala Ala Gly
 65                  70                  75                  80

Ala Arg Gly Cys Arg Leu Arg Ser Gln Leu Val Pro Val Arg Ala Leu
                85                  90                  95

Gly Leu Gly His Arg Ser Asp Glu Leu Val Arg Phe Arg Phe Cys Ser
                100                 105                 110

Gly Ser Cys Arg Arg Ala Arg Ser Pro His Asp Leu Ser Leu Ala Ser
                115                 120                 125

Leu Leu Gly Ala Gly Ala Leu Arg Pro Pro Gly Ser Arg Pro Val
    130                 135                 140

Ser Gln Pro Cys Cys Arg Pro Thr Arg Tyr Glu Ala Val Ser Phe Met
145                 150                 155                 160

Asp Val Asn Ser Thr Trp Arg Thr Val Asp Arg Leu Ser Ala Thr Ala
                165                 170                 175

Cys Gly Cys Leu Gly
                180

<210> SEQ ID NO 41
<211> LENGTH: 185
<212> TYPE: PRT
<213> ORGANISM: MURINE

<400> SEQUENCE: 41

Ser Leu Asp Pro Met Ser Arg Ser Pro Ala Ala Arg Asp Gly Pro Ser
 1               5                  10                  15

Pro Val Leu Ala Pro Pro Thr Asp His Leu Pro Gly Gly His Thr Ala
                20                  25                  30

His Leu Cys Ser Glu Arg Thr Leu Arg Pro Pro Gln Ser Pro Gln
        35                  40                  45

Pro Ala Pro Pro Pro Gly Pro Ala Leu Gln Ser Pro Ala Ala
    50                  55                  60

Leu Arg Gly Ala Arg Ala Ala Arg Ala Gly Thr Arg Ser Ser Arg Ala
 65                  70                  75                  80

Arg Thr Thr Asp Ala Arg Gly Cys Arg Leu Arg Ser Gln Leu Val Pro
                85                  90                  95

Val Ser Ala Leu Gly Leu Gly His Ser Ser Asp Glu Leu Ile Arg Phe
                100                 105                 110

Arg Phe Cys Ser Gly Ser Cys Arg Arg Ala Arg Ser Gln His Asp Leu
                115                 120                 125

Ser Leu Ala Ser Leu Leu Gly Ala Gly Ala Leu Arg Ser Pro Pro Gly
    130                 135                 140

Ser Arg Pro Ile Ser Gln Pro Cys Cys Arg Pro Thr Arg Tyr Glu Ala
145                 150                 155                 160

Val Ser Phe Met Asp Val Asn Ser Thr Trp Arg Thr Val Asp His Leu
                165                 170                 175

Ser Ala Thr Ala Cys Gly Cys Leu Gly
```

<210> SEQ ID NO 42
<211> LENGTH: 546
<212> TYPE: DNA
<213> ORGANISM: Homo sapiens

<400> SEQUENCE: 42

```
tccctgggct ccgcgccccg cagccctgcc ccccgcgaag gccccccgcc tgtcctggcg     60
tccccgccg gccacctgcc gggggacgc acggcccgct ggtgcagtgg aagagcccgg      120
cggccgccgc cgcagccttc tcggcccgcg ccccgccgc ctgcaccccc atctgctctt     180
ccccgcgggg gccgcgcggc gcgggctggg ggcccgggca gccgcgctcg ggcagcgggg    240
gcgcggggct gccgcctgcg ctcgcagctg gtgccggtgc gcgcgctcgg cctgggccac    300
cgctccgacg agctggtgcg tttccgcttc tgcagcggct cctgccgccg cgcgcgctct    360
ccacacgacc tcagcctggc cagcctactg ggcgccgggg ccctgcgacc gccccggggc    420
tcccggcccg tcagccagcc ctgctgccga cccacgcgct acgaagcggt ctccttcatg    480
gacgtcaaca gcacctggag aaccgtggac cgcctctccg ccaccgcctg cggctgcctg    540
ggctga                                                               546
```

<210> SEQ ID NO 43
<211> LENGTH: 558
<212> TYPE: DNA
<213> ORGANISM: MURINE

<400> SEQUENCE: 43

```
tccctggacc caatgtcccg cagccccgcc gctcgcgacg gtccctcacc ggtcttggcg     60
cccccacgg accacctgcc tgggggacac actgcgcatt tgtgcagcga aagaaccctg     120
cgaccccgc ctcagtctcc tcagcccgca ccccgccgc ctggtcccgc gctccagtct     180
cctcccgctg cgctccgcgg ggcacgcgcg gcgcgtgcag gaacccggag cagccgcgca    240
cggaccacag atgcgcgcgg ctgccgcctg cgctcgcagc tggtgccggt gagtgcgctc    300
ggcctaggcc acagctccga cgagctgata cgtttccgct tctgcagcgg ctcgtgccgc    360
cgagcacgct cccagcacga tctcagtctg gccagcctac tgggcgctgg ggccctacgg    420
tcgcctcccg ggtcccggcc gatcagccag ccctgctgcc ggcccactcg ctatgaggcc    480
gtctccttca tggacgtgaa cagcacctgg aggaccgtgg accacctctc cgccactgcc    540
tgcggctgtc tgggctga                                                  558
```

<210> SEQ ID NO 44
<211> LENGTH: 663
<212> TYPE: DNA
<213> ORGANISM: Homo sapiens

<400> SEQUENCE: 44

```
atggaacttg gacttggagg cctctccacg ctgtcccact gccctggcc taggcggcag      60
cctgccctgt ggcccaccct ggccgctctg gctctgctga gcagcgtcgc agaggcctcc    120
ctgggctccg cgccccgcag ccctgccccc gcgaaggcc cccgcctgt cctggcgtcc    180
ccgccggcc acctgccggg gggacgcacg gcccgctggt gcagtggaag agcccggcgg    240
ccgccgccgc agccttctcg gcccgcgccc cgccgcctg cacccccatc tgctcttccc    300
cgcggggc gcgcggcgcg ggctgggggc cgggcagcc gcgctcgggc agcggggcg      360
cggggctgcc gcctgcgctc gcagctggtg ccggtgcgcg cgctcggcct gggccaccgc    420
```

```
tccgacgagc tggtgcgttt ccgcttctgc agcggctcct gccgccgcgc gcgctctcca    480
cacgacctca gcctggccag cctactgggc gccggggccc tgcgaccgcc cccgggctcc    540
cggcccgtca gccagccctg ctgccgaccc acgcgctacg aggcggtctc cttcatggac    600
gtcaacagca cctggagaac cgtggaccgc ctctccgcca ccgcctgcgg ctgcctgggc    660
tga                                                                  663
```

```
<210> SEQ ID NO 45
<211> LENGTH:
<212> TYPE:
<213> ORGANISM:

<400> SEQUENCE: 45

This Sequence is intentionally skipped

<210> SEQ ID NO 46
<211> LENGTH:
<212> TYPE:
<213> ORGANISM:

<400> SEQUENCE: 46

This Sequence is intentionally skipped

<210> SEQ ID NO 47
<211> LENGTH:
<212> TYPE:
<213> ORGANISM:

<400> SEQUENCE: 47

This Sequence is intentionally skipped

<210> SEQ ID NO 48
<211> LENGTH: 39
<212> TYPE: PRT
<213> ORGANISM: Homo sapiens

<400> SEQUENCE: 48

Met Glu Leu Gly Leu Gly Gly Leu Ser Thr Leu Ser His Cys Pro Trp
  1               5                  10                  15

Pro Arg Arg Gln Pro Ala Leu Trp Pro Thr Leu Ala Ala Leu Ala Leu
             20                  25                  30

Leu Ser Ser Val Ala Glu Ala
         35

<210> SEQ ID NO 49
<211> LENGTH: 39
<212> TYPE: PRT
<213> ORGANISM: MURINE

<400> SEQUENCE: 49

Met Glu Leu Gly Leu Ala Glu Pro Thr Ala Leu Ser His Cys Leu Arg
  1               5                  10                  15

Pro Arg Trp Gln Ser Ala Trp Trp Pro Thr Leu Ala Val Leu Ala Leu
             20                  25                  30

Leu Ser Cys Val Thr Glu Ala
         35

<210> SEQ ID NO 50
<211> LENGTH: 68
<212> TYPE: PRT
```

```
<213> ORGANISM: Homo sapiens

<400> SEQUENCE: 50

Ser Leu Gly Ser Ala Pro Arg Ser Pro Ala Pro Arg Glu Gly Pro Pro
 1               5                  10                  15

Pro Val Leu Ala Ser Pro Ala Gly His Leu Pro Gly Gly Arg Thr Ala
                20                  25                  30

Arg Trp Cys Ser Gly Arg Ala Arg Pro Pro Gln Pro Ser Arg
            35                  40                  45

Pro Ala Pro Pro Pro Ala Pro Pro Ser Ala Leu Pro Arg Gly Gly
        50                  55                  60

Arg Ala Ala Arg
 65

<210> SEQ ID NO 51
<211> LENGTH: 72
<212> TYPE: PRT
<213> ORGANISM: MURINE

<400> SEQUENCE: 51

Ser Leu Asp Pro Met Ser Arg Ser Pro Ala Ala Arg Asp Gly Pro Ser
 1               5                  10                  15

Pro Val Leu Ala Pro Pro Thr Asp His Leu Pro Gly Gly His Thr Ala
                20                  25                  30

His Leu Cys Ser Glu Arg Thr Leu Arg Pro Pro Gln Ser Pro Gln
            35                  40                  45

Pro Ala Pro Pro Pro Gly Pro Ala Leu Gln Ser Pro Pro Ala Ala
        50                  55                  60

Leu Arg Gly Ala Arg Ala Ala Arg
 65                  70

<210> SEQ ID NO 52
<211> LENGTH: 107
<212> TYPE: PRT
<213> ORGANISM: Homo sapiens

<400> SEQUENCE: 52

Met Glu Leu Gly Leu Gly Gly Leu Ser Thr Leu Ser His Cys Pro Trp
 1               5                  10                  15

Pro Arg Arg Gln Pro Ala Leu Trp Pro Thr Leu Ala Ala Leu Ala Leu
                20                  25                  30

Leu Ser Ser Val Ala Glu Ala Ser Leu Gly Ser Ala Pro Arg Ser Pro
            35                  40                  45

Ala Pro Arg Glu Gly Pro Pro Val Leu Ala Ser Pro Ala Gly His
        50                  55                  60

Leu Pro Gly Gly Arg Thr Ala Arg Trp Cys Ser Gly Arg Ala Arg Arg
 65              70                  75                  80

Pro Pro Gln Pro Ser Arg Pro Ala Pro Pro Pro Ala Pro Pro
                85                  90                  95

Ser Ala Leu Pro Arg Gly Gly Arg Ala Ala Arg
            100                 105

<210> SEQ ID NO 53
<211> LENGTH: 111
<212> TYPE: PRT
<213> ORGANISM: MURINE

<400> SEQUENCE: 53
```

```
Met Glu Leu Gly Leu Ala Glu Pro Thr Ala Leu Ser His Cys Leu Arg
 1               5                  10                  15

Pro Arg Trp Gln Ser Ala Trp Trp Pro Thr Leu Ala Val Leu Ala Leu
                20                  25                  30

Leu Ser Cys Val Thr Glu Ala Ser Leu Asp Pro Met Ser Arg Ser Pro
            35                  40                  45

Ala Ala Arg Asp Gly Pro Ser Pro Val Leu Ala Pro Pro Thr Asp His
        50                  55                  60

Leu Pro Gly Gly His Thr Ala His Leu Cys Ser Glu Arg Thr Leu Arg
65                  70                  75                  80

Pro Pro Pro Gln Ser Pro Gln Pro Ala Pro Pro Pro Gly Pro Ala
                85                  90                  95

Leu Gln Ser Pro Pro Ala Ala Leu Arg Gly Ala Arg Ala Ala Arg
            100                 105                 110
```

<210> SEQ ID NO 54
<211> LENGTH: 117
<212> TYPE: DNA
<213> ORGANISM: Homo sapiens

<400> SEQUENCE: 54

```
atggaacttg gacttggagg cctctccacg ctgtcccact gcccctggcc taggcggcag      60
cctgccctgt ggcccaccct ggccgctctg gctctgctga gcagcgtcgc agaggcc       117
```

<210> SEQ ID NO 55
<211> LENGTH: 117
<212> TYPE: DNA
<213> ORGANISM: MURINE

<400> SEQUENCE: 55

```
atggaactgg gacttgcaga gcctactgca ttgtcccact gcctccggcc taggtggcag      60
tcagcctggt ggccaaccct agctgttcta gccctgctga gctgcgtcac agaagct       117
```

<210> SEQ ID NO 56
<211> LENGTH: 204
<212> TYPE: DNA
<213> ORGANISM: Homo sapiens

<400> SEQUENCE: 56

```
tccctgggct ccgcgccccg cagccctgcc ccccgcgaag gccccccgcc tgtcctggcg      60 tccccgccg gccacctgcc gggggacgc acggcccgct ggtgcagtgg aagagcccgg     120
cggccgccgc cgcagccttc tcggcccgcg ccccgccgc ctgcaccccc atctgctctt     180
ccccgcgggg gccgcgcggc gcgg                                            204
```

<210> SEQ ID NO 57
<211> LENGTH: 216
<212> TYPE: DNA
<213> ORGANISM: MURINE

<400> SEQUENCE: 57

```
tccctggacc caatgtcccg cagccccgcc gctcgcgacg gtccctcacc ggtcttggcg      60 cccccacgg accacctgcc tgggggacac actgcgcatt tgtgcagcga aagaaccctg     120 cgaccccgc ctcagtctcc tcagcccgca ccccgccgc ctggtcccgc gctccagtct     180
cctcccgctg cgctccgcgg ggcacgcgcg gcgcgt                              216
```

<210> SEQ ID NO 58

```
<211> LENGTH: 321
<212> TYPE: DNA
<213> ORGANISM: Homo sapiens

<400> SEQUENCE: 58
atggaacttg gacttggagg cctctccacg ctgtcccact gcccctggcc taggcggcag      60
cctgccctgt ggcccaccct ggccgctctg gctctgctga gcagcgtcgc agaggcctcc     120
ctgggctccg cgcccgcag ccctgccccc gcgaaggcc cccgcctgt cctggcgtcc       180
cccgccggcc acctgccggg gggacgcacg gcccgctggt gcagtggaag agccggcgg     240
ccgccgccgc agccttctcg gcccgcgccc cgccgcctg cacccccatc tgctcttccc     300
cgcgggggcc gcgcggcgcg g                                              321

<210> SEQ ID NO 59
<211> LENGTH: 333
<212> TYPE: DNA
<213> ORGANISM: MURINE

<400> SEQUENCE: 59
gcaggaaccc ggagcagccg cgcacggacc acagatgcgc gcggctgccg cctgcgctcg      60
cagctggtgc cggtgagtgc gctcggccta ggccacagct ccgacgagct gatacgtttc     120
cgcttctgca gcggctcgtg ccgccagca cgctcccagc acgatctcag tctggccagc      180
ctactgggcg ctggggccct acgtcgcct cccgggtccc ggccgatcag ccagccctgc      240
tgccggccca ctcgctatga ggccgtctcc ttcatggacg tgaacagcac ctggaggacc     300
gtggaccacc tctccgccac tgcctgcggc tgt                                  333

<210> SEQ ID NO 60
<211> LENGTH: 342
<212> TYPE: DNA
<213> ORGANISM: MURINE

<400> SEQUENCE: 60
tcagcccaga cagccgcagg cagtggcgga gaggtggtcc acggtcctcc aggtgctgtt      60
cacgtccatg aaggagacgg cctcatagcg agtgggccgg cagcagggct ggctgatcgg     120
ccgggacccg ggaggcgacc gtagggcccc agcgcccagt aggctggcca gactgagatc     180
gtgctgggag cgtgctcggc ggcacgagcc gctgcagaag cggaaacgta tcagctcgtc     240
ggagctgtgg cctaggccga gcgcactcac cggcaccagc tgcgagcgca ggcggcagcc     300
gcgcgcatct gtggtccgtg cgcggctgct ccgggttcct gc                       342

<210> SEQ ID NO 61
<211> LENGTH: 351
<212> TYPE: DNA
<213> ORGANISM: MURINE

<400> SEQUENCE: 61
tcagcccaga cagccgcagg cagtggcgga gaggtggtcc acggtcctcc aggtgctgtt      60
cacgtccatg aaggagacgg cctcatagcg agtgggccgg cagcagggct ggctgatcgg     120
ccgggacccg ggaggcgacc gtagggcccc agcgcccagt aggctggcca gactgagatc     180
gtgctgggag cgtgctcggc ggcacgagcc gctgcagaag cggaaacgta tcagctcgtc     240
ggagctgtgg cctaggccga gcgcactcac cggcaccagc tgcgagcgca ggcggcagcc     300
gcgcgcatct gtggtccgtg cgcggctgct ccgggttcct gcacgcgccg c             351
```

```
<210> SEQ ID NO 62
<211> LENGTH: 435
<212> TYPE: DNA
<213> ORGANISM: MURINE

<400> SEQUENCE: 62
tcagcccaga cagccgcagg cagtggcgga gaggtggtcc acggtcctcc aggtgctgtt      60
cacgtccatg aaggagacgg cctcatagcg agtgggccgg cagcagggct ggctgatcgg     120
ccgggacccg ggaggcgacc gtagggcccc agcgcccagt aggctggcca gactgagatc     180
gtgctgggag cgtgctcggc ggcacgagcc gctgcagaag cggaaacgta tcagctcgtc     240
ggagctgtgg cctaggccga gcgcactcac cggcaccagc tgcgagcgca ggcggcagcc     300
gcgcgcatct gtggtccgtg cgcggctgct ccgggttcct gcacgcgccg cgcgtgcccc     360
gcggagcgca gcgggaggag actggagcgc gggaccaggc ggcgggggtg cgggctgagg     420
agactgaggc ggggg                                                     435

<210> SEQ ID NO 63
<211> LENGTH: 400
<212> TYPE: PRT
<213> ORGANISM: Homo sapiens

<400> SEQUENCE: 63
```

Met Val Arg Pro Leu Asn Pro Arg Pro Leu Pro Val Val Leu Met
1               5                   10                  15

Leu Leu Leu Leu Pro Pro Ser Pro Leu Pro Leu Ala Ala Gly Asp
            20                  25                  30

Pro Leu Pro Thr Glu Ser Arg Leu Met Asn Ser Cys Leu Gln Ala Arg
        35                  40                  45

Arg Lys Cys Gln Ala Asp Pro Thr Cys Ser Ala Ala Tyr His His Leu
    50                  55                  60

Asp Ser Cys Thr Ser Ser Ile Ser Thr Pro Leu Pro Ser Glu Glu Pro
65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Gly Asn
        115                 120                 125

Tyr Glu Leu Asp Val Ser Pro Tyr Glu Asp Thr Val Thr Ser Lys Pro
    130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175

Arg Leu Arg Lys Ala Tyr Gly Glu Ala Cys Ser Gly Pro His Cys Gln
            180                 185                 190

Arg His Val Cys Leu Arg Gln Leu Leu Thr Phe Phe Glu Lys Ala Ala
        195                 200                 205

Glu Pro His Ala Gln Gly Leu Leu Leu Cys Pro Cys Ala Pro Asn Asp
    210                 215                 220

Arg Gly Cys Gly Glu Arg Arg Arg Asn Thr Ile Ala Pro Asn Cys Ala
225                 230                 235                 240

Leu Pro Pro Val Ala Pro Asn Cys Leu Glu Leu Arg Arg Leu Cys Phe
                245                 250                 255

Ser Asp Pro Leu Cys Arg Ser Arg Leu Val Asp Phe Gln Thr His Cys
            260                 265                 270

His Pro Met Asp Ile Leu Gly Thr Cys Ala Thr Glu Gln Ser Arg Cys
            275                 280                 285

Leu Arg Ala Tyr Leu Gly Leu Ile Gly Thr Ala Met Thr Pro Asn Phe
            290                 295                 300

Val Ser Asn Val Asn Thr Ser Val Ala Leu Ser Cys Thr Cys Arg Gly
305                 310                 315                 320

Ser Gly Asn Leu Gln Glu Glu Cys Glu Met Leu Glu Gly Phe Phe Ser
            325                 330                 335

His Asn Pro Cys Leu Thr Glu Ala Ile Ala Ala Lys Met Arg Phe His
            340                 345                 350

Ser Gln Leu Phe Ser Gln Asp Trp Pro His Pro Thr Phe Ala Val Met
            355                 360                 365

Ala His Gln Asn Glu Asn Pro Ala Val Arg Pro Gln Pro Trp Val Pro
            370                 375                 380

Ser Leu Phe Ser Cys Thr Leu Pro Leu Ile Leu Leu Ser Leu Trp
385                 390                 395                 400

<210> SEQ ID NO 64
<211> LENGTH: 397
<212> TYPE: PRT
<213> ORGANISM: Murine

<400> SEQUENCE: 64

Met Gly Leu Ser Trp Ser Pro Arg Pro Pro Leu Leu Met Ile Leu Leu
  1               5                  10                  15

Leu Val Leu Ser Leu Trp Leu Pro Leu Gly Ala Gly Asn Ser Leu Ala
             20                  25                  30

Thr Glu Asn Arg Phe Val Asn Ser Cys Thr Gln Ala Arg Lys Lys Cys
            35                  40                  45

Glu Ala Asn Pro Ala Cys Lys Ala Ala Tyr Gln His Leu Gly Ser Cys
     50                  55                  60

Thr Ser Ser Leu Ser Arg Pro Leu Pro Leu Glu Ser Ala Met Ser
 65                  70                  75                  80

Ala Asp Cys Leu Glu Ala Ala Glu Gln Leu Arg Asn Ser Ser Leu Ile
             85                  90                  95

Asp Cys Arg Cys His Arg Arg Met Lys His Gln Ala Thr Cys Leu Asp
            100                 105                 110

Ile Tyr Trp Thr Val His Pro Ala Arg Ser Leu Gly Asp Tyr Glu Leu
            115                 120                 125

Asp Val Ser Pro Tyr Glu Asp Thr Val Thr Ser Lys Pro Trp Lys Met
     130                 135                 140

Asn Leu Ser Lys Leu Asn Met Leu Lys Pro Asp Ser Asp Leu Cys Leu
145                 150                 155                 160

Lys Phe Ala Met Leu Cys Thr Leu His Asp Lys Cys Asp Arg Leu Arg
            165                 170                 175

Lys Ala Tyr Gly Glu Ala Cys Ser Gly Ile Arg Cys Gln Arg His Leu
            180                 185                 190

Cys Leu Ala Gln Leu Arg Ser Phe Phe Glu Lys Ala Ala Glu Ser His
            195                 200                 205

Ala Gln Gly Leu Leu Leu Cys Pro Cys Ala Pro Glu Asp Ala Gly Cys
     210                 215                 220

Gly Glu Arg Arg Arg Asn Thr Ile Ala Pro Ser Cys Ala Leu Pro Ser
225                 230                 235                 240

```
Val Thr Pro Asn Cys Leu Asp Leu Arg Ser Phe Cys Arg Ala Asp Pro
            245                 250                 255
Leu Cys Arg Ser Arg Leu Met Asp Phe Gln Thr His Cys His Pro Met
            260                 265                 270
Asp Ile Leu Gly Thr Cys Ala Thr Glu Gln Ser Arg Cys Leu Arg Ala
            275                 280                 285
Tyr Leu Gly Leu Ile Gly Thr Ala Met Thr Pro Asn Phe Ile Ser Lys
            290                 295                 300
Val Asn Thr Thr Val Ala Leu Ser Cys Thr Cys Arg Gly Ser Gly Asn
305                 310                 315                 320
Leu Gln Asp Glu Cys Glu Gln Leu Glu Arg Ser Phe Ser Gln Asn Pro
            325                 330                 335
Cys Leu Val Glu Ala Ile Ala Ala Lys Met Arg Phe His Arg Gln Leu
            340                 345                 350
Phe Ser Gln Asp Trp Ala Asp Ser Thr Phe Ser Val Val Gln Gln Gln
            355                 360                 365
Asn Ser Asn Pro Ala Leu Arg Leu Gln Pro Arg Leu Pro Ile Leu Ser
            370                 375                 380
Phe Ser Ile Leu Pro Leu Ile Leu Leu Gln Thr Leu Trp
385                 390                 395

<210> SEQ ID NO 65
<211> LENGTH: 1203
<212> TYPE: DNA
<213> ORGANISM: Homo sapiens

<400> SEQUENCE: 65
atggtgcgcc ccctgaaccc gcgaccgctg ccgcccgtag tcctgatgtt gctgctgctg      60
ctgccgccgt cgccgctgcc tctcgcagcc ggagaccccc ttcccacaga aagccgactc     120
atgaacagct gtctccaggc caggaggaag tgccaggctg atcccacctg cagtgctgcc     180
taccaccacc tggattcctg cacctctagc ataagcaccc cactgccctc agaggagcct     240
tcggtccctg ctgactgcct ggaggcagca cagcaactca ggaacagctc tctgataggc     300
tgcatgtgcc accggcgcat gaagaaccag gttgcctgct ggacatctat tggaccgtt      360
caccgtgccc gcagccttgg taactatgag ctggatgtct cccccctatga agacacagtg     420
accagcaaac cctggaaaat gaatctcagc aaactgaaca tgctcaaacc agactcagac     480
ctctgcctca gtttgccat gctgtgtact ctcaatgaca agtgtgaccg gctgcgcaag     540
gcctacgggg aggcgtgctc cgggcccac tgccagcgcc acgtctgcct caggcagctg     600
ctcactttct tcgagaaggc cgccgagccc acgcgcagg gcctgctact gtgcccatgt     660
gcccccaacg accggggctg cggggagcgc cggcgcaaca ccatcgcccc caactgcgcg     720
ctgccgcctg tggcccccaa ctgcctggag ctgcggcgc tctgcttctc cgaccgcctt     780
tgcagatcac gcctggtgga tttccagacc cactgccatc ccatggacat cctaggaact     840
tgtgcaacag agcagtccag atgtctacga gcatacctgg ggctgattgg gactgccatg     900
acccccaact tgtcagcaa tgtcaacacc agtgttgcct taagctgcac ctgccgaggc     960
agtggcaacc tgcaggagga gtgtgaaatg ctggaagggt tcttctccca accccctgc    1020
ctcacggagg ccattgcagc taagatgcgt tttcacagcc aactcttctc ccaggactgg    1080
ccacacccta cctttgctgt gatggcacac cagaatgaaa accctgctgt gaggccacag    1140
ccctgggtgc cctctctttt ctcctgcacg cttcccttga ttctgctcct gagcctatgg    1200
``` tag                                                                          1203

<210> SEQ ID NO 66
<211> LENGTH: 24
<212> TYPE: DNA
<213> ORGANISM: RAT

<400> SEQUENCE: 66
tcgcgacggt ggctcaccgg tctt                                                   24

<210> SEQ ID NO 67
<211> LENGTH: 24
<212> TYPE: DNA
<213> ORGANISM: RAT

<400> SEQUENCE: 67
gcacgagccg ctgcagaagc ggaa                                                   24

<210> SEQ ID NO 68
<211> LENGTH: 1652
<212> TYPE: DNA
<213> ORGANISM: Homo sapiens

<400> SEQUENCE: 68
ctctgagctt ctctgagcct tgtttgctca tctggaaaaa ggggattaaa ccatttacct            60
catggagttg tgaaagaata gctgcaaagc acctaacaca tagtaaggtt cccagtgcag           120
ctacttctgc tgggttgagt ctagctgtgt aggccccttg ttcctcacct ggagaaactg           180
gggtggcagg ccgtccccc acaaaagata actcatctct taatttgcaa gctgcctcaa            240
caggagggtg ggggaacagc tcaacaatgg ctgatgggcg ctcctggtgt tgatagagat           300
ggaacttgga cttggaggcc tctccacgct gtcccactgc ccctggccta ggcggcaggt           360
gagtggttct cccagtgact cctacctggt actgaggaaa ggcggcttga ctggtgaggg           420
agagcagggc ttggcttggg cagcggttag gtgtgggagg gaaaatggtc agggagggac           480
caggtgaatg ggaggaggag cgggacttct ctgaatggtc ggtgcactca ggtgattcct           540
cccctgggct cccagaggca gcaaaccat tatactggaa cctaggccct tcctgagttt            600
cccctccaca cagctaggag cccatgcccg gcctgatctc agcccgagga cagcccctcc           660
ttgaggtcct tcctccccaa gcccacctgg gtgccctctt tctccctgag gctccacttg           720
gtctctccgc gcagcctgcc ctgtgggcca ccctggccgc tctggctctg ctgagcagcg           780
tcgcagaggc ctccctgggc tccgcgcccc gcagccctgc ccccgcgaa ggccccccgc            840
ctgtcctggc gtccccgcc ggccacctgc cgggtaggtg agaggcgag ggggcggggc             900
ggggctggcc cgggacaccg cgcgtgactg gtctcattc caggggacg cacggcccgc             960
tggtgcagtg gaagagcccg gcggccgccg ccgcagcctt ctcggcccgc gccccgccg           1020
cctgcacccc catctgctct tccccgcggg ggccgcgcgg cgcgggctgg gggcccgggc          1080
agccgcgctc gggcagcggg ggcgcgggc tgccgcctgc gctcgcagct ggtgccggtg           1140
cgcgcgctcg gcctgggcca ccgctccgac gagctggtgc gtttccgctt ctgcagcggc          1200
tcctgccgcc gcgcgcgctc tccacacgac ctcagcctgg ccagcctact gggcgccggg          1260
gccctgcgac cgccccggg ctccggccc gtcagccagc cctgctgccg acccacgcgc            1320
tacgaagcgg tctccttcat ggacgtcaac agcacctgga gaaccgtgga ccgcctctcc          1380
gccaccgcct gcggctgcct gggctgaggg ctcgctccag ggctttgcag actggaccct          1440
taccggtggc tcttcctgcc tgggaccctc ccgcagagtc ccactagcca gcggcctcag          1500

```
ccagggacga aggcctcaaa gctgagaggc cctgccggt gggtgatgga tatcatcccc    1560
gaacaggtga agggacaact gactagcagc cccagagccc tcaccctgcg gatcccagcc    1620
taaaagacac cagagacctc agctatggag cc                                 1652
```

<210> SEQ ID NO 69
<211> LENGTH: 1652
<212> TYPE: DNA
<213> ORGANISM: MURINE

<400> SEQUENCE: 69

```
ggctccatag ctgaggtctc tggtgtcttt taggctggga tccgcagggt gagggctctg     60
gggctgctag tcagttgtcc cttcacctgt tcggggatga tatccatcac ccaccggcag    120
gggcctctca gctttgaggc cttcgtccct ggctgaggcc gctggctagt gggactctgc    180
gggagggtcc caggcaggaa gagccaccgg taagggtcca gtctgcaaag ccctggagcg    240
agccctcagc ccaggcagcc gcaggcggtg gcggagaggc ggtccacggt tctccaggtg    300
ctgttgacgt ccatgaagga gaccgcttcg tagcgcgtgg gtcggcagca gggctggctg    360
acgggccggg agcccggggg cggtcgcagg gccccggcgc ccagtaggct ggccaggctg    420
aggtcgtgtg gagagcgcgc gcggcggcag gagccgctgc agaagcggaa acgcaccagc    480
tcgtcggagc ggtggcccag gccgagcgcg cgcaccggca ccagctgcga gcgcaggcgg    540
cagccccgcg ccccgctgc ccgagcgcgg ctgcccgggc cccagcccg cgccgcgcgg     600 cccccgcggg gaagagcaga tgggggtgca ggcggcgggg gcgcgggccg agaaggctgc    660
ggcggcggcc gccgggctct tccactgcac cagcgggccg tgcgtccccc tggaatgaga    720
cccagtcacg cgcggtgtcc cgggccagcc ccgccccgcc ccctcgccct ctcacctacc    780
cggcaggtgg ccggcggggg acgccaggac aggcggggg cttcgcggg gggcagggct      840 gcggggcgcg gagcccaggg aggcctctgc gacgctgctc agcagagcca gagcggccag    900
ggtgggccac agggcaggct gcgcggagag accaagtgga gcctcaggga gaaagagggc    960
acccaggtgg gcttggggag gaaggacctc aaggagggc tgtcctcggg ctgagatcag    1020
gccgggcatg ggctcctagc tgtgtggagg ggaaactcag gaagggccta ggttccagta    1080
taatgggttt gctgcctctg ggagcccagg ggaggaatca cctgagtgca ccgaccattc    1140
agagaagtcc cgctcctcct cccattcacc tggtccctcc ctgaccattt tccctcccac    1200
acctaaccgc tgcccaagcc aagccctgct ctccctcacc agtcaagccg cctttcctca    1260
gtaccaggta ggagtcactg ggagaaccac tcacctgccg cctaggccag gggcagtggg    1320
acagcgtgga gaggcctcca agtccaagtt ccatctctat caacaccagg agcgcccatc    1380
agccattgtt gagctgttcc cccaccctcc tgttgaggca gcttgcaaat taagagatga    1440
gttatctttt gtggggacc ggcctgccac cccagtttct ccaggtgagg aacaagggc     1500 ctacacagct agactcaacc cagcagaagt agctgcactg gaaccttac tatgtgttag    1560 gtgctttgca gctattcttt cacaactcca tgaggtaaat ggtttaatcc cctttttcca    1620
gatgagcaaa caaggctcag agaagctcag ag                                1652
```

<210> SEQ ID NO 70
<211> LENGTH: 24
<212> TYPE: PRT
<213> ORGANISM: Homo sapiens

<400> SEQUENCE: 70

```
Ala Ser Leu Ser Leu Val Cys Ser Ser Gly Lys Arg Gly Leu Asn His
 1               5                  10                  15
Leu Pro His Gly Val Val Lys Glu
            20
```

<210> SEQ ID NO 71
<211> LENGTH: 4
<212> TYPE: PRT
<213> ORGANISM: Homo sapiens

<400> SEQUENCE: 71

```
Leu Gln Ser Thr
 1
```

<210> SEQ ID NO 72
<211> LENGTH: 13
<212> TYPE: PRT
<213> ORGANISM: Homo sapiens

<400> SEQUENCE: 72

```
His Ile Val Arg Phe Pro Val Gln Leu Leu Leu Leu Gly
 1               5                  10
```

<210> SEQ ID NO 73
<211> LENGTH: 488
<212> TYPE: DNA
<213> ORGANISM: RAT

<400> SEQUENCE: 73

| | | | | | |
|---|---|---|---|---|---|
| ccggtgagcg | ctctcggcct | gggccacagc | tccgacgagc | tgatacgttt | ccgcttctgc | 60 |
| agcggttcgt | gccgccgagc | acgctccccg | cacgatctca | gcctggccag | cctgctgggc | 120 |
| gccggggccc | tgcggtcgcc | tcccgggtcc | cggccgatca | gccagccctg | ttgccggccc | 180 |
| actcgctatg | aggccgtctc | cttcatggat | gtgaacagca | cctggagaac | cgtggaccat | 240 |
| ctctccgcca | ccgcctgcgg | ctgtctgggc | tgaggatgat | cttcaagctt | ttgcacactg | 300 |
| gacccatatg | tcgccctacc | tggaacagcc | cacggggcc  | tcactagcta | ggagcctcaa | 360 |
| ctcaacagga | agctcaggcc | tcaggccgat | gagggacaga | cagagcctgg | aaagatgacc | 420 |
| gaaccactga | ccaacagtcc | caaggtgttc | atggatccca | gctctacaga | cagcagaaac | 480 |
| ctcagcta   |            |            |            |            |            | 488 |

<210> SEQ ID NO 74
<211> LENGTH: 488
<212> TYPE: DNA
<213> ORGANISM: RAT

<400> SEQUENCE: 74

| | | | | | |
|---|---|---|---|---|---|
| tagctgaggt | ttctgctgtc | tgtagagctg | ggatccatga | acaccttggg | actgttggtc | 60 |
| agtggttcgg | tcatctttcc | aggctctgtc | tgtccctcat | cggcctgagg | cctgagcttc | 120 |
| ctgttgagtt | gaggctccta | gctagtgagg | ccccgtgggg | ctgttccagg | tagggcgaca | 180 |
| tatgggtcca | gtgtgcaaaa | gcttgaagat | catcctcagc | ccagacagcc | gcaggcggtg | 240 |
| gcggagagat | ggtccacggt | tctccaggtc | ctgttcacat | ccatgaagga | gacgcctca  | 300 |
| tagcgagtgg | gccggcaaca | gggctggctg | atcggccggg | acccgggagg | cgaccgcagg | 360 |
| gccccggcgc | ccagcaggct | ggccaggctg | agatcgtgcg | gggagcgtgc | tcggcggcac | 420 |
| gaaccgctgc | agaagcggaa | acgtatcagc | tcgtcggagc | tgtggcccag | gccgagagcg | 480 |
| ctcaccgg   |            |            |            |            |            | 488 |

```
<210> SEQ ID NO 75
<211> LENGTH: 90
<212> TYPE: PRT
<213> ORGANISM: RAT

<400> SEQUENCE: 75

Pro Val Ser Ala Leu Gly Leu Gly His Ser Ser Asp Glu Leu Ile Arg
 1               5                  10                  15

Phe Arg Phe Cys Ser Gly Ser Cys Arg Arg Ala Arg Ser Pro His Asp
                20                  25                  30

Leu Ser Leu Ala Ser Leu Leu Gly Ala Gly Ala Leu Arg Ser Pro Pro
            35                  40                  45

Gly Ser Arg Pro Ile Ser Gln Pro Cys Cys Arg Pro Thr Arg Tyr Glu
50                  55                  60

Ala Val Ser Phe Met Asp Val Asn Ser Thr Trp Arg Thr Val Asp His
65                  70                  75                  80

Leu Ser Ala Thr Ala Cys Gly Cys Leu Gly
                85                  90

<210> SEQ ID NO 76
<211> LENGTH: 20
<212> TYPE: DNA
<213> ORGANISM: RAT

<400> SEQUENCE: 76
ccggtgagcg ctctcggcct                                          20

<210> SEQ ID NO 77
<211> LENGTH: 24
<212> TYPE: DNA
<213> ORGANISM: RAT

<400> SEQUENCE: 77
ttctggattc tcccagagga gttc                                     24

<210> SEQ ID NO 78
<211> LENGTH: 6
<212> TYPE: PRT
<213> ORGANISM: Homo sapiens

<400> SEQUENCE: 78

Trp Pro Leu Trp Leu Cys
 1               5

<210> SEQ ID NO 79
<211> LENGTH: 50
<212> TYPE: PRT
<213> ORGANISM: Homo sapiens

<400> SEQUENCE: 79

Ala Ala Ser Gln Arg Pro Pro Trp Ala Pro Arg Pro Ala Ala Leu Pro
 1               5                  10                  15

Pro Ala Lys Ala Pro Arg Leu Ser Trp Arg Pro Pro Ala Thr Cys
                20                  25                  30

Arg Val Gly Glu Arg Ala Arg Gly Arg Gly Ala Gly Pro Gly His
            35                  40                  45

Arg Ala
50
```

```
<210> SEQ ID NO 80
<211> LENGTH: 14
<212> TYPE: PRT
<213> ORGANISM: Homo sapiens

<400> SEQUENCE: 80

Gly Leu Ala Pro Gly Leu Cys Arg Leu Asp Pro Tyr Arg Trp
 1               5                  10

<210> SEQ ID NO 81
<211> LENGTH: 68
<212> TYPE: PRT
<213> ORGANISM: Homo sapiens

<400> SEQUENCE: 81

Leu Cys Arg Pro Leu Val Pro His Leu Glu Lys Leu Gly Trp Gln Ala
 1               5                  10                  15

Gly Pro Pro Gln Lys Ile Thr His Leu Leu Ile Cys Lys Leu Pro Gln
            20                  25                  30

Gln Glu Gly Gly Gly Thr Ala Gln Gln Trp Leu Met Gly Ala Pro Gly
        35                  40                  45

Val Asp Arg Asp Gly Thr Trp Thr Trp Arg Pro Leu His Ala Val Pro
    50                  55                  60

Leu Pro Leu Ala
 65

<210> SEQ ID NO 82
<211> LENGTH: 8
<212> TYPE: PRT
<213> ORGANISM: Homo sapiens

<400> SEQUENCE: 82

Ala Ala Gly Glu Trp Phe Ser Gln
 1               5

<210> SEQ ID NO 83
<211> LENGTH: 12
<212> TYPE: PRT
<213> ORGANISM: Homo sapiens

<400> SEQUENCE: 83

Leu Leu Pro Gly Thr Glu Glu Arg Arg Leu Asp Trp
 1               5                  10

<210> SEQ ID NO 84
<211> LENGTH: 10
<212> TYPE: PRT
<213> ORGANISM: Homo sapiens

<400> SEQUENCE: 84

Gly Arg Ala Gly Leu Gly Leu Gly Ser Gly
 1               5                  10

<210> SEQ ID NO 85
<211> LENGTH: 44
<212> TYPE: PRT
<213> ORGANISM: Homo sapiens

<400> SEQUENCE: 85

Val Trp Glu Gly Lys Trp Ser Gly Arg Asp Gln Val Asn Gly Arg Arg
 1               5                  10                  15

Ser Gly Thr Ser Leu Asn Gly Arg Cys Thr Gln Val Ile Pro Pro Leu
            20                  25                  30
```

Gly Ser Gln Arg Gln Gln Thr His Tyr Thr Gly Thr
            35                  40

<210> SEQ ID NO 86
<211> LENGTH: 16
<212> TYPE: PRT
<213> ORGANISM: Homo sapiens

<400> SEQUENCE: 86

Ala Leu Pro Glu Phe Pro Leu His Thr Ala Arg Ser Pro Cys Pro Ala
 1               5                  10                  15

<210> SEQ ID NO 87
<211> LENGTH: 45
<212> TYPE: PRT
<213> ORGANISM: Homo sapiens

<400> SEQUENCE: 87

Ser Gln Pro Glu Asp Ser Pro Ser Leu Arg Ser Phe Leu Pro Lys Pro
 1               5                  10                  15

Thr Trp Val Pro Ser Phe Ser Leu Arg Leu His Leu Val Ser Pro Arg
            20                  25                  30

Ser Leu Pro Cys Gly Pro Pro Trp Pro Leu Trp Leu Cys
        35                  40                  45

<210> SEQ ID NO 88
<211> LENGTH: 50
<212> TYPE: PRT
<213> ORGANISM: Homo sapiens

<400> SEQUENCE: 88

Ala Ala Ser Gln Arg Pro Pro Trp Ala Pro Arg Pro Ala Ala Leu Pro
 1               5                  10                  15

Pro Ala Lys Ala Pro Arg Leu Ser Trp Arg Pro Pro Ala Thr Cys
            20                  25                  30

Arg Val Gly Glu Arg Ala Arg Gly Arg Gly Ala Gly Pro Gly His
        35                  40                  45

Arg Ala
    50

<210> SEQ ID NO 89
<211> LENGTH: 159
<212> TYPE: PRT
<213> ORGANISM: Homo sapiens

<400> SEQUENCE: 89

Leu Gly Leu Ile Pro Gly Gly Arg Thr Ala Arg Trp Cys Ser Gly Arg
 1               5                  10                  15

Ala Arg Arg Pro Pro Pro Gln Pro Ser Arg Pro Ala Pro Pro Pro Pro
            20                  25                  30

Ala Pro Pro Ser Ala Leu Pro Arg Gly Gly Arg Ala Ala Arg Ala Gly
        35                  40                  45

Gly Pro Gly Ser Arg Ala Arg Ala Ala Gly Ala Arg Gly Cys Arg Leu
    50                  55                  60

Arg Ser Gln Leu Val Pro Val Arg Ala Leu Gly Leu Gly His Arg Ser
65                  70                  75                  80

Asp Glu Leu Val Arg Phe Arg Phe Cys Ser Gly Ser Cys Arg Arg Ala
                85                  90                  95

Arg Ser Pro His Asp Leu Ser Leu Ala Ser Leu Leu Gly Ala Gly Ala

```
                100                 105                 110
Leu Arg Pro Pro Gly Ser Arg Pro Val Ser Gln Pro Cys Cys Arg
        115                 120                 125

Pro Thr Arg Tyr Glu Ala Val Ser Phe Met Asp Val Asn Ser Thr Trp
        130                 135                 140

Arg Thr Val Asp Arg Leu Ser Ala Thr Ala Cys Gly Cys Leu Gly
145                 150                 155
```

<210> SEQ ID NO 90
<211> LENGTH: 71
<212> TYPE: PRT
<213> ORGANISM: Homo sapiens

<400> SEQUENCE: 90

```
Gly Leu Ala Pro Gly Leu Cys Arg Leu Asp Pro Tyr Arg Trp Leu Phe
1               5                   10                  15

Leu Pro Gly Thr Leu Pro Gln Ser Pro Thr Ser Gln Arg Pro Gln Pro
                20                  25                  30

Gly Thr Lys Ala Ser Lys Leu Arg Gly Pro Cys Arg Trp Val Met Asp
            35                  40                  45

Ile Ile Pro Glu Gln Val Lys Gly Gln Leu Thr Ser Ser Pro Arg Ala
        50                  55                  60

Leu Thr Leu Arg Ile Pro Ala
65                  70
```

<210> SEQ ID NO 91
<211> LENGTH: 10
<212> TYPE: PRT
<213> ORGANISM: Homo sapiens

<400> SEQUENCE: 91

```
Lys Thr Pro Glu Thr Ser Ala Met Glu Pro
1               5                   10
```

<210> SEQ ID NO 92
<211> LENGTH: 4
<212> TYPE: PRT
<213> ORGANISM: Homo sapiens

<400> SEQUENCE: 92

```
Ser Glu Leu Leu
1
```

<210> SEQ ID NO 93
<211> LENGTH: 10
<212> TYPE: PRT
<213> ORGANISM: Homo sapiens

<400> SEQUENCE: 93

```
Ala Leu Phe Ala His Leu Glu Lys Gly Asp
1               5                   10
```

<210> SEQ ID NO 94
<211> LENGTH: 7
<212> TYPE: PRT
<213> ORGANISM: Homo sapiens

<400> SEQUENCE: 94

```
Thr Ile Tyr Leu Met Glu Leu
1               5
```

-continued

```
<210> SEQ ID NO 95
<211> LENGTH: 9
<212> TYPE: PRT
<213> ORGANISM: Homo sapiens

<400> SEQUENCE: 95

Lys Asn Ser Cys Lys Ala Pro Asn Thr
 1               5

<210> SEQ ID NO 96
<211> LENGTH: 34
<212> TYPE: PRT
<213> ORGANISM: Homo sapiens

<400> SEQUENCE: 96

Gly Ser Gln Cys Ser Tyr Phe Cys Trp Val Glu Ser Cys Val Gly
 1               5                  10                  15

Pro Leu Phe Leu Thr Trp Arg Asn Trp Gly Arg Pro Val Pro His
                20                  25                  30

Lys Arg

<210> SEQ ID NO 97
<211> LENGTH: 16
<212> TYPE: PRT
<213> ORGANISM: Homo sapiens

<400> SEQUENCE: 97

Phe Ala Ser Cys Leu Asn Arg Arg Val Gly Glu Gln Leu Asn Asn Gly
 1               5                  10                  15

<210> SEQ ID NO 98
<211> LENGTH: 70
<212> TYPE: PRT
<213> ORGANISM: Homo sapiens

<400> SEQUENCE: 98

Trp Ala Leu Leu Val Leu Ile Glu Met Glu Leu Gly Leu Gly Gly Leu
 1               5                  10                  15

Ser Thr Leu Ser His Cys Pro Trp Pro Arg Arg Gln Val Ser Gly Ser
                20                  25                  30

Pro Ser Asp Ser Tyr Leu Val Leu Arg Lys Gly Gly Leu Thr Gly Glu
            35                  40                  45

Gly Glu Gln Gly Leu Ala Trp Ala Ala Val Arg Cys Gly Arg Glu Asn
        50                  55                  60

Gly Gln Gly Gly Thr Arg
    65                  70

<210> SEQ ID NO 99
<211> LENGTH: 8
<212> TYPE: PRT
<213> ORGANISM: Homo sapiens

<400> SEQUENCE: 99

Met Gly Gly Gly Ala Gly Leu Leu
 1               5

<210> SEQ ID NO 100
<211> LENGTH: 6
<212> TYPE: PRT
<213> ORGANISM: Homo sapiens

<400> SEQUENCE: 100
```

```
Met Val Gly Ala Leu Arg
  1               5
```

<210> SEQ ID NO 101
<211> LENGTH: 42
<212> TYPE: PRT
<213> ORGANISM: Homo sapiens

<400> SEQUENCE: 101

```
Phe Leu Pro Trp Ala Pro Arg Gly Ser Lys Pro Ile Ile Leu Glu Pro
  1               5                  10                  15

Arg Pro Phe Leu Ser Phe Pro Ser Thr Gln Leu Gly Ala His Ala Arg
                 20                  25                  30

Pro Asp Leu Ser Pro Arg Thr Ala Pro Pro
             35                  40
```

<210> SEQ ID NO 102
<211> LENGTH: 14
<212> TYPE: PRT
<213> ORGANISM: Homo sapiens

<400> SEQUENCE: 102

```
Gly Pro Ser Ser Pro Ser Pro Gly Cys Pro Leu Ser Pro
  1               5                  10
```

<210> SEQ ID NO 103
<211> LENGTH: 55
<212> TYPE: PRT
<213> ORGANISM: Homo sapiens

<400> SEQUENCE: 103

```
Gly Ser Thr Trp Ser Leu Arg Ala Ala Cys Pro Val Ala His Pro Gly
  1               5                  10                  15

Arg Ser Gly Ser Ala Glu Gln Arg Arg Arg Gly Leu Pro Gly Leu Arg
                 20                  25                  30

Ala Pro Gln Pro Cys Pro Pro Arg Arg Pro Ala Cys Pro Gly Val
             35                  40                  45

Pro Arg Arg Pro Pro Ala Gly
         50                  55
```

<210> SEQ ID NO 104
<211> LENGTH: 215
<212> TYPE: PRT
<213> ORGANISM: Homo sapiens

<400> SEQUENCE: 104

```
Val Arg Gly Arg Gly Gly Ala Gly Leu Ala Arg Asp Thr Ala Arg
  1               5                  10                  15

Asp Trp Val Ser Phe Gln Gly Asp Ala Arg Pro Ala Gly Ala Val Glu
                 20                  25                  30

Glu Pro Gly Gly Arg Arg Ser Leu Leu Gly Pro Arg Pro Arg Arg
             35                  40                  45

Leu His Pro His Leu Leu Phe Pro Ala Gly Ala Ala Arg Arg Gly Leu
         50                  55                  60

Gly Ala Arg Ala Ala Leu Gly Gln Arg Gly Arg Gly Ala Ala Ala
 65                  70                  75                  80

Cys Ala Arg Ser Trp Cys Arg Cys Ala Arg Ser Ala Trp Thr Ala
                 85                  90                  95

Pro Thr Ser Trp Cys Val Ser Ala Ser Ala Ala Pro Ala Ala Ala
            100                 105                 110
```

-continued

```
Arg Ala Leu His Thr Thr Ser Ala Trp Pro Ala Tyr Trp Ala Pro Gly
            115                 120                 125
Pro Cys Asp Arg Pro Arg Ala Pro Gly Pro Ser Ala Ser Pro Ala Ala
        130                 135                 140
Asp Pro Arg Ala Thr Lys Arg Ser Pro Ser Trp Thr Ser Thr Ala Pro
145                 150                 155                 160
Gly Glu Pro Trp Thr Ala Ser Pro Pro Pro Ala Ala Ala Trp Ala
                165                 170                 175
Glu Gly Ser Leu Gln Gly Phe Ala Asp Trp Thr Leu Thr Gly Gly Ser
            180                 185                 190
Ser Cys Leu Gly Pro Ser Arg Arg Val Pro Leu Ala Ser Gly Leu Ser
        195                 200                 205
Gln Gly Arg Arg Pro Gln Ser
    210                 215
```

<210> SEQ ID NO 105
<211> LENGTH: 6
<212> TYPE: PRT
<213> ORGANISM: Homo sapiens

<400> SEQUENCE: 105

```
Glu Ala Pro Ala Gly Gly
  1               5
```

<210> SEQ ID NO 106
<211> LENGTH: 7
<212> TYPE: PRT
<213> ORGANISM: Homo sapiens

<400> SEQUENCE: 106

```
Trp Ile Ser Ser Pro Asn Arg
  1               5
```

<210> SEQ ID NO 107
<211> LENGTH: 23
<212> TYPE: PRT
<213> ORGANISM: Homo sapiens

<400> SEQUENCE: 107

```
Leu Ala Ala Pro Glu Pro Ser Pro Cys Gly Ser Gln Pro Lys Arg His
  1               5                  10                  15
Gln Arg Pro Gln Leu Trp Ser
                20
```

<210> SEQ ID NO 108
<211> LENGTH: 50
<212> TYPE: PRT
<213> ORGANISM: Homo sapiens

<400> SEQUENCE: 108

```
Pro Leu Ser Phe Ser Glu Pro Cys Leu Leu Ile Trp Lys Lys Gly Ile
  1               5                  10                  15
Lys Pro Phe Thr Ser Trp Ser Cys Glu Arg Ile Ala Ala Lys His Leu
                20                  25                  30
Thr His Ser Lys Val Pro Ser Ala Ala Thr Ser Ala Gly Leu Ser Leu
            35                  40                  45
Ala Val
    50
```

```
<210> SEQ ID NO 109
<211> LENGTH: 46
<212> TYPE: PRT
<213> ORGANISM: Homo sapiens

<400> SEQUENCE: 109

Ala Pro Cys Ser Ser Pro Gly Glu Thr Gly Val Ala Gly Arg Ser Pro
 1               5                  10                  15

Thr Lys Asp Asn Ser Ser Leu Asn Leu Gln Ala Ala Ser Thr Gly Gly
                20                  25                  30

Trp Gly Asn Ser Ser Thr Met Ala Asp Gly Arg Ser Trp Cys
            35                  40                  45

<210> SEQ ID NO 110
<211> LENGTH: 21
<212> TYPE: PRT
<213> ORGANISM: Homo sapiens

<400> SEQUENCE: 110

Arg Trp Asn Leu Asp Leu Glu Ala Ser Pro Arg Cys Pro Thr Ala Pro
 1               5                  10                  15

Gly Leu Gly Gly Arg
                20

<210> SEQ ID NO 111
<211> LENGTH: 10
<212> TYPE: PRT
<213> ORGANISM: Homo sapiens

<400> SEQUENCE: 111

Val Val Leu Pro Val Thr Pro Thr Trp Tyr
 1               5                  10

<210> SEQ ID NO 112
<211> LENGTH: 4
<212> TYPE: PRT
<213> ORGANISM: Homo sapiens

<400> SEQUENCE: 112

Gly Lys Ala Ala
 1

<210> SEQ ID NO 113
<211> LENGTH: 61
<212> TYPE: PRT
<213> ORGANISM: Homo sapiens

<400> SEQUENCE: 113

Leu Val Arg Glu Ser Arg Ala Trp Leu Gly Gln Arg Leu Gly Val Gly
 1               5                  10                  15

Gly Lys Met Val Arg Glu Gly Pro Gly Glu Trp Glu Glu Arg Asp
                20                  25                  30

Phe Ser Glu Trp Ser Val His Ser Gly Asp Ser Ser Pro Gly Leu Pro
            35                  40                  45

Glu Ala Ala Asn Pro Leu Tyr Trp Asn Leu Gly Pro Ser
        50                  55                  60

<210> SEQ ID NO 114
<211> LENGTH: 6
<212> TYPE: PRT
<213> ORGANISM: Homo sapiens

<400> SEQUENCE: 114
```

```
Val Ser Pro Pro His Ser
 1               5
```

```
<210> SEQ ID NO 115
<211> LENGTH: 87
<212> TYPE: PRT
<213> ORGANISM: Homo sapiens

<400> SEQUENCE: 115
```

```
Glu Pro Met Pro Gly Leu Ile Ser Ala Arg Gly Gln Pro Leu Glu
 1               5                  10                  15

Val Leu Pro Pro Gln Ala His Leu Gly Ala Leu Phe Leu Pro Glu Ala
             20                  25                  30

Pro Leu Gly Leu Ser Ala Gln Pro Ala Leu Trp Pro Thr Leu Ala Ala
         35                  40                  45

Leu Ala Leu Leu Ser Ser Val Ala Glu Ala Ser Leu Gly Ser Ala Pro
     50                  55                  60

Arg Ser Pro Ala Pro Arg Glu Gly Pro Pro Val Leu Ala Ser Pro
 65                  70                  75                  80

Ala Gly His Leu Pro Gly Arg
                 85
```

```
<210> SEQ ID NO 116
<211> LENGTH: 201
<212> TYPE: PRT
<213> ORGANISM: Homo sapiens

<400> SEQUENCE: 116
```

```
Glu Gly Glu Gly Ala Gly Arg Gly Trp Pro Gly Thr Pro Arg Val Thr
 1               5                  10                  15

Gly Ser His Ser Arg Gly Thr His Gly Pro Leu Val Gln Trp Lys Ser
             20                  25                  30

Pro Ala Ala Ala Ala Ala Phe Ser Ala Arg Ala Pro Ala Ala Cys
         35                  40                  45

Thr Pro Ile Cys Ser Ser Pro Arg Gly Pro Arg Gly Ala Gly Trp Gly
     50                  55                  60

Pro Gly Gln Pro Arg Ser Gly Ser Gly Gly Ala Gly Leu Pro Pro Ala
 65                  70                  75                  80

Leu Ala Ala Gly Ala Gly Ala Arg Ala Arg Pro Gly Pro Pro Leu Arg
                 85                  90                  95

Arg Ala Gly Ala Phe Pro Leu Leu Gln Arg Leu Leu Pro Pro Arg Ala
            100                 105                 110

Leu Ser Thr Arg Pro Gln Pro Gly Gln Pro Thr Gly Arg Arg Gly Pro
            115                 120                 125

Ala Thr Ala Pro Gly Leu Pro Ala Arg Gln Pro Ala Leu Leu Pro Thr
        130                 135                 140

His Ala Leu Arg Ser Gly Leu Leu His Gly Arg Gln Gln His Leu Glu
145                 150                 155                 160

Asn Arg Gly Pro Pro Leu Arg His Arg Leu Arg Leu Pro Gly Leu Arg
                165                 170                 175

Ala Arg Ser Arg Ala Leu Gln Thr Gly Pro Leu Pro Val Ala Leu Pro
            180                 185                 190

Ala Trp Asp Pro Pro Ala Glu Ser His
        195                 200
```

```
<210> SEQ ID NO 117
```

```
<211> LENGTH: 32
<212> TYPE: PRT
<213> ORGANISM: Homo sapiens

<400> SEQUENCE: 117

Pro Ala Ala Ser Ala Arg Asp Glu Gly Leu Lys Ala Glu Arg Pro Leu
 1               5                  10                  15

Pro Val Gly Asp Gly Tyr His Pro Arg Thr Gly Glu Gly Thr Thr Asp
             20                  25                  30

<210> SEQ ID NO 118
<211> LENGTH: 22
<212> TYPE: PRT
<213> ORGANISM: Homo sapiens

<400> SEQUENCE: 118

Gln Pro Gln Ser Pro His Pro Ala Asp Pro Ser Leu Lys Asp Thr Arg
 1               5                  10                  15

Asp Leu Ser Tyr Gly Ala
             20

<210> SEQ ID NO 119
<211> LENGTH: 23
<212> TYPE: PRT
<213> ORGANISM: RAT

<400> SEQUENCE: 119

Ser Ser Ser Phe Cys Thr Leu Asp Pro Tyr Val Ala Leu Pro Gly Thr
 1               5                  10                  15

Ala Pro Arg Gly Leu Thr Ser
             20

<210> SEQ ID NO 120
<211> LENGTH: 46
<212> TYPE: PRT
<213> ORGANISM: RAT

<400> SEQUENCE: 120

Glu Pro Gln Leu Asn Arg Lys Leu Arg Pro Gln Ala Asp Glu Gly Gln
 1               5                  10                  15

Thr Glu Pro Gly Lys Met Thr Glu Pro Leu Thr Asn Ser Pro Lys Val
             20                  25                  30

Phe Met Asp Pro Ser Ser Thr Asp Ser Arg Asn Leu Ser Tyr
         35                  40                  45
```